United States Patent
Engel et al.

[11] Patent Number: 5,945,381
[45] Date of Patent: Aug. 31, 1999

[54] HERBICIDAL HETEROCYCLICALLY ANNULATED BENZOYLISOTHIAZOLES

[75] Inventors: Stefan Engel, Idstein; Wolfgang von Deyn, Neustadt; Regina Luise Hill, Speyer; Uwe Kardorff, Mannheim; Martina Otten, Ludwigshafen; Peter Plath, Frankenthal; Marcus Vossen, Mannheim; Ulf Misslitz, Neustadt; Helmut Walter, Obrigheim; Karl-Otto Westphalen, Speyer, all of Germany

[73] Assignee: BASF Aktiengesellschaft, Ludwigshafen, Germany

[21] Appl. No.: 09/171,195

[22] PCT Filed: Apr. 14, 1997

[86] PCT No.: PCT/EP97/01858

§ 371 Date: Oct. 15, 1998

§ 102(e) Date: Oct. 15, 1998

[87] PCT Pub. No.: WO97/38988

PCT Pub. Date: Oct. 23, 1997

[30] Foreign Application Priority Data

Apr. 16, 1996 [DE] Germany .......................... 196 14 856

[51] Int. Cl.⁶ .......................... A01N 43/80; C07D 417/06
[52] U.S. Cl. .......................... 504/269; 548/213; 548/214
[58] Field of Search ..................... 548/214, 213; 504/269

[56] References Cited

U.S. PATENT DOCUMENTS 4,187,099 2/1980 Franz et al. ................................ 71/90

FOREIGN PATENT DOCUMENTS

| | | |
|---|---|---|
| 418175 | 3/1991 | European Pat. Off. |
| 449223 | 10/1991 | European Pat. Off. |
| 524781 | 1/1993 | European Pat. Off. |
| 527036 | 2/1993 | European Pat. Off. |
| 527037 | 2/1993 | European Pat. Off. |
| 560482 | 9/1993 | European Pat. Off. |
| 580439 | 1/1994 | European Pat. Off. |
| 588357 | 3/1994 | European Pat. Off. |
| 609797 | 8/1994 | European Pat. Off. |
| 609798 | 8/1994 | European Pat. Off. |
| 617010 | 9/1994 | European Pat. Off. |
| 636622 | 2/1995 | European Pat. Off. |
| 4427998 | 8/1994 | Germany . |
| 2284600 | 6/1995 | United Kingdom . |
| 94/14782 | 7/1994 | WIPO . |
| 94/18179 | 8/1994 | WIPO . |
| 95/15691 | 6/1995 | WIPO . |
| 95/16678 | 6/1995 | WIPO . |
| 95/22903 | 8/1995 | WIPO . |
| 95/22904 | 8/1995 | WIPO . |
| 95/25105 | 9/1995 | WIPO . |
| 96/25413 | 8/1996 | WIPO . |

Primary Examiner—Robert Gerstl
Attorney, Agent, or Firm—Keil & Weinkauf

[57] ABSTRACT

4-Benzoylisothiazoles of the general formula 1

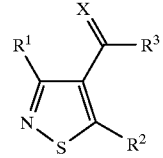

where the substituents have the following meanings:
X is oxygen or sulfur;
$R^3$ is a radical of the general formula 2a–d

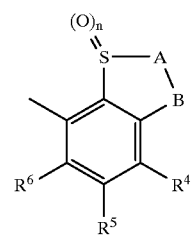

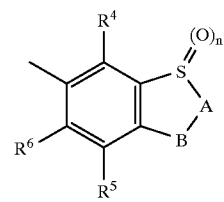

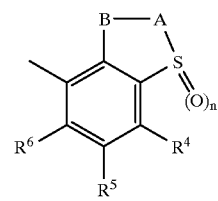

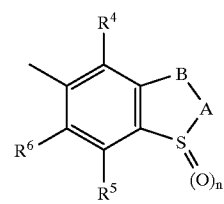

where n, A, B and the substituents $R^4$, $R^5$ and $R^6$ have the meanings given in claim 1,
salts of the 4-benzoylisothiazoles of the general formula 1 which are conventionally used in agriculture, processes for their preparation, and their use as herbicides.

18 Claims, No Drawings

HERBICIDAL HETEROCYCLICALLY ANNULATED BENZOYLISOTHIAZOLES

DESCRIPTION

The present invention relates to novel substituted benzoylisothiazoles, to processes for their preparation, and to their use as herbicides.

The patent literature (EP 0 527 036, EP 0 527 037, EP 0 560 482, EP 0 580 439, EP 0 588 357, EP 609 797, EP 0 609 798, EP 0 636 622, WO 94/14782, WO 94/ 18179, WO 95/15691 and WO 95/16678) discloses that substituted 4-benzoyl-5-cycloalkylisoxazoles represent a class of compounds with pronounced herbicidal activity pre-emergence. 4-(2-Sulfonylmethyl-4-trifluoromethylbenzoyl)-5-cyclopropylisoxazole, a representative of this class of compounds, is developed by Rhone-Poulenc as a herbicidal active ingredient against mono- and dicotyledon harmful plants used pre-emergence in maize (i.e. corn; RPA 201772, Technical Bulletin).

Moreover, the herbicidal and insecticidal activity of substituted 4-alkyl- or 4-cycloalkyl-5-aryl- or 5-hetaryl-isoxazoles has been disclosed (GB 2 284 600, Wo 95/22903, WO 95/22904 and WO 95/25105).

The herbicidal activity of the known compounds is not only deficient post-emergence, but also only partially satisfactorily pre-emergence and shows gaps with regard to its compatibility with crop plants.

To date, the prior art has not disclosed herbicidal or insecticidal 4-benzoylisothiazoles according to the invention.

With the view to their synthesis, 4-benzoylisothiazoles have only been of limited interest to date. While substituted isothiazoles and their carbocycle-fused derivatives have been the aim of basic investigations (for example: D. L. Pain, B. J. Peart, K. R. H. Wooldridge, Comprehensive Heterocyclic Chemistry, Vol. 6, Part 4B, p. 131, Ed. A. R. Katritzky, Pergamon Press, Oxford 1984), acylated and, in particular, benzoylated derivatives have only been described occasionally in the literature (for example: A. J. Layton, E. Lunt, J. Chem. Soc. (1968) 611, A. Alberola, F. Alonso, P. Cuadrado, C. M. Sanudo, Synth. Commun. 17 (1987) 1207, A. Alberola, F. Alonso, P. Cuadrado, C. M. Sanudo, J. Heterocycl. Chem. 25 (1988) 235).

Some hydroxypropylaminocarbonyl-substituted 4-benzoylisothiazoles have been examined in EP 0 524 781 and EP 0 617 010 as muscle-relaxing agents or suitable therapeutic amides in the case of incontinence. EP 0 449 223 claims that 3,5-di(tert-butyl)-4-hydroxybenzoylisothiazoles inhibit 5-lipoxygenase and cyclooxygenase and thus have an antiinflammatory activity.

It is an object of the present invention to provide novel herbicidally active ingredients which have an improved profile of is action and an improved crop plant compatibility.

Surprisingly, the benzoylisothiazoles of the general formula 1 according to the invention have a pronounced herbicidal activity against harmful plants combined with crop plant compatibility.

The present invention relates to 4-benzoylisothiazoles of the general formula 1

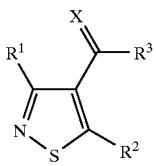

where the substituents have the following meanings:

X is oxygen or sulfur;

$R^1$ is hydrogen, alkyl, alkenyl, alkynyl; unsubstituted or substituted alkoxycarbonyl;

unsubstituted or substituted aryl, unsubstituted or substituted heterocyclyl or unsubstituted or substituted hetaryl;

$R^2$ is hydrogen, alkyl, alkenyl, alkynyl, cycloalkyl or cycloalkenyl, it being possible for these radicals to have attached to them one or more of the following groups: halogen, alkyl, alkenyl or alkynyl;

aryl, it being possible for this radical to have attached to it one or more of the following groups:
    alkyl, alkenyl, alkynyl, alkoxy, alkenyloxy, alkynyloxy, alkylthio or alkenylthio, it being possible for these radicals to be partially or fully halogenated or to have attached to them one or more of the following groups:
    alkoxy, alkenyloxy, aryloxy, alkylsulfonyl, alkenylsulfonyl or arylsulfonyl;
    alkylsulfonyl or alkoxycarbonyl; unsubstituted or substituted aryloxy or unsubstituted or substituted arylthio;
    unsubstituted or substituted mono- or dialkylamino, unsubstituted or substituted mono- or diarylamino or unsubstituted or substituted N-alkyl-N-arylamino, it being possible for alkyl and aryl to be identical or different;
    halogen, cyano or nitro;
  hetaryl or heterocyclyl, it being possible for these radicals to be partially or fully halogenated or to have attached to them one or more of the following groups:
    alkyl, alkoxy or aryl, and it being possible, in the case of heterocyclyl, for at least one of the nitrogens to have attached to it one of the following groups:
    alkyl, alkenyl, alkynyl, cycloalkyl, haloalkyl, alkoxy, alkenyloxy, alkynyloxy, cycloalkyloxy, haloalkoxy, unsubstituted or substituted aryl or unsubstituted or substituted aryloxy;

$R^3$ is a radical of the general formula 2a–d

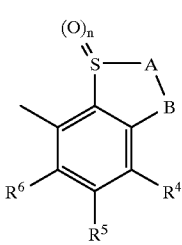

-continued

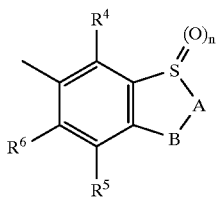

2b

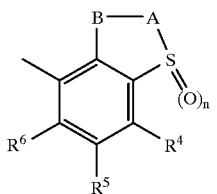

2c

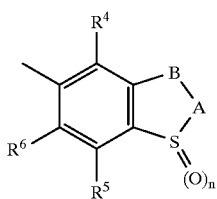

2d where n, A, B and the substituents $R^4$, $R^5$ and $R^6$ have the following meanings:

n is zero, one or two,

A is a chain (—$CR^7R^8$—), (—$CR^7R^8$—$CR^9R^{10}$—), (—$CR^7$=$CR^8$—), (—$CR^7R^8$—$CR^7$=$CR^8$—) or a nitrogen atom which, in turn, can be substituted by a substituent selected from the group consisting of hydrogen, alkyl, alkenyl, unsubstituted or substituted aryl or arylalkyl, alkoxy, halogen, haloalkyl or haloalkoxy;

B is a group consisting of C=O, C=$NR^{11}$, $CR^{12}$—$NR^{13}R^{14}$, $CR^{12}$—$OR^{15}$, $CR^{16}R^{17}$, $CR^{12}$—$SR^{15}$, or 1,3-dioxanyl or 1,3-dioxolanyl, each of which is substituted by hydrogen or alkyl, or a hetero atom selected from the group consisting of oxygen, sulfur or nitrogen, it being possible for the nitrogen, in turn, to be substituted by a substituent selected from the group consisting of hydrogen, alkyl, alkenyl, unsubstituted or substituted aryl or arylalkyl, alkoxy, halogen, haloalkyl or haloalkoxy, the bond between A and B can be saturated or unsaturated, $R^4$–$R^6$ can be identical or different and independently of one another are hydrogen, alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, alkynylamino, cycloalkylamino, cycloalkenylamino, sulfonyl, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, aminosulfonyl, unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different, alkoxyaminocarbonyl, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfoxyl, haloalkenylsulfoxyl, haloalkynylsulfoxyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; cyano or nitro; or one of the following groups:

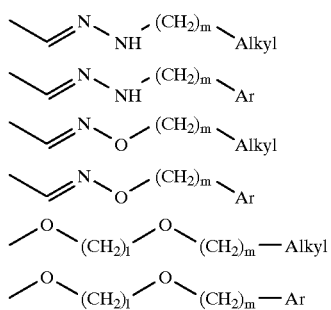

-continued

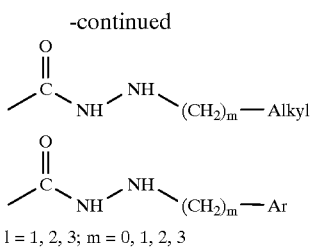

l = 1, 2, 3; m = 0, 1, 2, 3

$R^7$, $R^8$ independently of one another are hydrogen, alkyl, haloalkyl, alkoxy, haloalkoxy; unsubstituted or substituted phenyl, it being possible for the substituents to consist of alkyl, alkoxy, haloalkoxy, haloalkyl, halogen, cyano, nitro;

$R^9$ is hydrogen, alkyl, haloalkyl, alkoxy, haloalkoxy;
unsubstituted or substituted phenyl, it being possible for the substituents to consist of alkyl, alkoxy, haloalkoxy, haloalkyl, halogen, cyano, nitro;

$R^{10}$ is hydrogen, alkyl, haloalkyl, alkoxy, haloalkoxy;
unsubstituted or substituted phenyl, it being possible for the substituents to consist of alkyl, alkoxy, haloalkoxy, haloalkyl, halogen, cyano, nitro;

$R^{11}$ is hydrogen, —$NR^9R^4$; alkyl, haloalkyl, alkoxy, haloalkoxy, alkenyl, haloalkenyl, alkynyl;
unsubstituted or substituted phenyl, it being possible for the substituents to consist of alkyl, alkoxy, haloalkoxy, haloalkyl, halogen, cyano, nitro; unsubstituted or substituted benzyl, it being possible for the substituents to consist of alkyl, alkoxy, haloalkoxy, haloalkyl, halogen, cyano, nitro;
unsubstituted or substituted benzyloxy, it being possible for the substituents to consist of alkyl, alkoxy, haloalkoxy, haloalkyl, halogen, cyano, nitro;

$R^{12}$ is hydrogen, alkyl, alkoxy, haloalkyl, haloalkoxy;
unsubstituted or substituted phenyl, it being possible for the substituents to consist of one to three halogens, alkyl, alkoxy, haloalkoxy, nitro; $R^{12}$ and $R^7$ or $R^{12}$ and $R^9$ can form a bond;

$R^{13}$, $R^{14}$ independently of one another are hydrogen, alkyl, alkenyl, haloalkyl, haloalkenyl, alkoxy, haloalkoxy;
unsubstituted or substituted phenyl, it being possible for the substituents to consist of alkyl, alkoxy, haloalkoxy, haloalkyl, halogen, cyano, nitro;
unsubstituted or substituted benzyl, it being possible for the substituents to consist of alkyl, alkoxy, haloalkoxy, haloalkyl, halogen, cyano, nitro;

$R^{15}$ is hydrogen, alkyl, haloalkyl, unsubstituted or substituted phenyl, it being possible for the substituents to consist of alkyl, alkoxy, haloalkoxy, haloalkyl, halogen, cyano, nitro;
unsubstituted or substituted benzyl, it being possible for the substituents to consist of alkyl, alkoxy, haloalkoxy, haloalkyl, halogen, cyano, nitro;

$R^{16}$, $R^{17}$ independently of one another are hydrogen, alkyl;
unsubstituted or substituted phenyl, it being possible for the substituents to consist of one to three halogens, alkyl, alkoxy, haloalkoxy, nitro; $R^{16}$ and $R^7$ or $R^{16}$ and $R^9$ can form a bond;

and to salts of the 4-benzoylisothiazoles of the general formula 1 which are customary in agriculture.

In the definitions of the compounds I given at the outset, collective terms were used which generally represent the following groups:

Halogen: fluorine, chlorine, bromine and iodine;

Alkyl: straight-chain or branched alkyl groups having 1 to 6 or 10 carbon atoms, eg. $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylamino: an amino group which has attached to it a straight-chain or branched alkyl group having 1 to 6 carbon atoms as mentioned above;

Dialkylamino: an amino group which has attached to it two straight-chain or branched alkyl groups which are independent of one another and which have in each case 1 to 6 carbon atoms as mentioned above;

Alkylcarbonyl: straight-chain or branched alkyl groups having 1 to 10 carbon atoms which are bonded to the skeleton via a carbonyl group (—CO—);

Alkylsulfonyl: straight-chain or branched alkyl groups having 1 to 6 or 10 carbon atoms which are bonded to the skeleton via a sulfonyl group (—$SO_2$—);

Alkylsulfoxyl: straight-chain or branched alkyl groups having 1 to 6 carbon atoms which are bonded to the skeleton via a sulfoxyl group (—S(=O)—);

Alkylaminocarbonyl: alkylamino groups having 1 to 6 carbon atoms as mentioned above which are bonded to the skeleton via a carbonyl group (—CO—);

Dialkylaminocarbonyl: dialkylamino groups having in each case 1 to 6 carbon atoms per alkyl radical as mentioned above which are bonded to the skeleton via a carbonyl group (—CO—);

Alkylaminothiocarbonyl: alkylamino groups having 1 to 6 carbon atoms as mentioned above which are bonded to the skeleton via a thiocarbonyl group (—CS—);

Dialkylaminothiocarbonyl: dialkylamino groups having in each case 1 to 6 carbon atoms per alkyl radical as mentioned above which are bonded to the skeleton via a thiocarbonyl group (—CS—);

Haloalkyl: straight-chain or branched alkyl groups having 1 to 6 carbon atoms, it being possible for some or all of the hydrogen atoms in these groups to be replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2, 2-trichloroethyl and pentafluoroethyl;

Alkoxy: straight-chain or branched alkyl groups having 1 to 6 carbon atoms as mentioned above which are bonded to the skeleton via an oxygen atom (—O—) eg. $C_1$–$C_6$-alkoxy, such as methyloxy, ethyloxy, propyloxy, 1-methylethyloxy, butyloxy, 1-methyl-propyloxy, 2-methylpropyloxy, 1,1-dimethylethyloxy, pentyloxy, 1-methylbutyloxy, 2-methylbutyloxy, 3-methylbutyloxy, 2,2-di-methylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1, 2-dimethylbutyloxy, 1,3-dimethylbutyloxy, 2,2-dimethylbutyloxy, 2,3- dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

Alkoxycarbonyl: straight-chain or branched alkyl groups having 1 to 6 carbon atoms which are bonded to the skeleton via an oxycarbonyl group (—OC(=O)—);

Haloalkoxy: straight-chain or branched alkyl groups having 1 to 6 carbon atoms, it being possible for some or all of the hydrogen atoms in these groups to be replaced by halogen atoms as mentioned above and these groups being bonded to the skeleton via an oxygen atom;

Alkylthio: straight-chain or branched alkyl groups having 1 to 4 or 6 carbon atoms as mentioned above which are bonded to the skeleton via a sulfur atom (—S—), eg. $C_1$–$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

Cycloalkyl: monocyclic alkyl groups having 3 to 6 carbon ring members, eg. cyclopropyl, cyclobutyl, cyclopentyl and cyclohexyl;

Alkenyl: straight-chain or branched alkenyl groups having 2 to 6 or 10 carbon atoms and a double bond in any position, eg. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1, 1-dimethyl-3-butenyl, 1,2-dimethyl-1-butenyl, 1,2-dimethyl-2-butenyl, 1,2-dimethyl-3-butenyl, 1,3-dimethyl-1-butenyl, 1, 3-dimethyl-2-butenyl, 1, 3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: straight-chain or branched alkenyl groups have 2 to 6 carbon atoms and a double bond in any position which are bonded to the skeleton via an oxygen atom (—O—);

Alkenylthio or alkenylamino: straight-chain or branched alkenyl groups having 2 to 6 carbon atoms and a double bond in any position which are bonded to the skeleton via a sulfur atom (alkenylthio) or via a nitrogen atom (alkenylamino).

Alkenylcarbonyl: straight-chain or branched alkenyl groups having 2 to 10 carbon atoms and a double bond in any position which are bonded to the skeleton via a carbonyl group (—CO—);

Alkynyl: straight-chain or branched alkynyl groups having 2 to 10 carbon atoms and a triple bond in any position, eg. $C_2$–$C_6$-alkynyl, such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1.1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

Alkynyloxy or alkynylthio and alkynylamino: straight-chain or branched alkynyl groups having 2 to 6 carbon atoms and a triple bond in any position which are bonded to the skeleteon via an oxygen atom (alkynyloxy) or via a sulfur atom (alkynylthio) or via a nitrogen atom (alkynylamino).

Alkynylcarbonyl: straight-chain or branched alkynyl groups having 3 to 10 carbon atoms and a triple bond in any position which are bonded to the skeleton via a carbonyl group (—CO—);

Cycloalkenyl or cycloalkenyloxy, cycloalkenylthio and cycloalkenylamino: monocyclic alkenyl groups having 3 to 6 carbon ring members which are bonded to the skeleton directly or via an oxygen atom (cycloalkenyloxy) or a sulfur atom (cycloalkenylthio) or via a nitrogen atom (cycloalkenylamino), eg. cyclopropenyl, cyclobutenyl, cyclopentenyl or cyclohexenyl.

Cycloalkoxy or cycloalkylthio and cycloalkylamino: monocyclic alkyl groups having 3 to 6 carbon ring members which are bonded to the skeleton via an oxygen atom (cycloalkyloxy) or a sulfur atom (cycloalkylthio) or via a nitrogen atom (cycloalkylamino), eg. cyclopropyl, cyclobutyl, cyclopentyl or cyclohexyl;

Cycloalkylcarbonyl: cycloalkyl groups as defined above which are bonded to the skeleton via a carbonyl group (—CO—);

Cycloalkoxycarbonyl: cycloalkoxy groups as defined above which are bonded to the skeleton via a carbonyl group (—CO—);

Alkenloxycarbonyl: alkenyloxy groups as defined above which are bonded to the skeleton via a carbonyl group (—CO—);

Alkynyloxycarbonyl: alkynyloxy groups as defined above which are bonded to the skeleton via a carbonyl group (—CO—);

Heterocyclyl: three- to six-membered saturated or partially unsaturated mono- or polycyclic heterocycles which contain one to three hetero atoms selected from a group consisting of oxygen, nitrogen and sulfur and which are bonded to the skeleton directly via carbon, eg. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazoldinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydro-fur-4-yl, 2,3-dihydro-fur-5-yl, 2,5-dihydro-fur-2-yl, 2,5-dihydro-fur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-Tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, Aryl, or aryloxy, arylthio, arylcarbonyl, aryloxycarbonyl, arylsulfonyl and arylsulfoxyl: aromatic mono- or polycyclic hydrocarbon radicals which are bonded to the skeleton directly or (aryloxy) via an oxygen atom (—O—) or (arylthio) via a sulfur atom (—S—) or (arylcarbonyl) via a carbonyl group (—CO—), or aryloxycarbonyl via an oxycarbonyl group (—OCO—) or (arylsulfonyl) via a sulfonyl group (—SO$_2$—) or (arylsulfoxyl) via a sulfoxyl group (—SO—), eg. phenyl, naphthyl and phenylanthrenyl, or phenyloxy, naphthyloxy and phenanthrenyloxy and the corresponding carbonyl and sulfonyl radicals;

Arylamino: aromatic mono- or polycyclic hydrocarbon radicals which are bonded to the skeleton via a nitrogen atom.

Hetaryl: aromatic mono- or polycyclic radicals which, besides carbon ring members, can additionally contain one to four nitrogen atoms or one to three nitrogen atoms and one oxygen or one sulfur atom or one oxygen or one sulfur atom and which are bonded to the skeleton directly via carbon, eg.

5-membered hetaryl containing one to three nitrogen atoms: 5-membered hetaryl ring groups which, besides carbon atoms, can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl, containing one to four nitrogen atoms or one to three nitrogen atoms and one sulfur or oxygen atom or one oxygen or one sulfur atom: 5-membered hetaryl ring groups which, besides carbon atoms, can contain one to four nitrogen atoms or one to three nitrogen atoms and one sulfur or oxygen atom or one oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

carbocycle-fused 5-membered hetaryl, containing one to three nitrogen atoms or one nitrogen atom and/or one oxygen or sulfur atom: 5-membered hetaryl ring groups which, besides carbon atoms, can contain one to four nitrogen atoms or one to three nitrogen atoms and one sulfur or oxygen atom or one oxygen or one sulfur atom as ring members and in which two adjacent carbon ring members or one oxygen and an adjacent carbon ring member can be bridged by a buta-1,3-diene-1,4-diyl group;

6-membered hetaryl, containing one to three, or one to four, nitrogen atoms: 6-membered hetaryl ring groups which, besides carbon atoms, can contain one to three, or one to four, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl, containing one to four nitrogen atoms: 6-membered hetaryl ring groups in which two adjacent carbon ring members can be bridged by a buta-1,3-diene-1,4-diyl group, eg. quinoline, isoquinoline, quinazoline and quinoxaline, and the corresponding oxy, thio, carbonyl or sulfonyl groups.

The term "partially or fully halogenated" is intended to express that in thus characterized groups some or all of the hydrogen atoms can be replaced by identical or different halogen atoms as mentioned above.

"Unsubstituted or substituted" denotes that the organic group in question can be substituted as desired, suitable substituents being, in principle, all those listed in the present application.

Preferred substituents are hydrogen, alkyl, alkeny, alkynyl, preferably cycloalkyl, cycloalkylalkyl, cycloalkylalkenyl, aryl, arylalkyl, arylalkenyl, hydroxyl, alkoxy, alkenyloxy, cycloalkoxy, cycloalkylalkoxy, aryloxy, arylalkoxy, thio, alkylthio, alkenylthio, cycloalkylthio, cycloalkylalkylthio, arylthio, arylalkylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, cycloalkylamino, cycloalkenylamino, sulfonyl, alkylsulfonyl, alkenylsulfonyl, cycloalkylsulfonyl, cycloalkylalkylsulfonyl, arylsulfonyl, arylalkylsulfonyl, sulfoxyl, alkylsulfoxyl, alkenylsulfoxyl, cycloalkylsulfoxyl, cycloalkylalkylsulfoxyl, arylsulfoxyl, arylalkylsulfoxyl, alkylcarbonyl, alkenylcarbonyl, cycloalkylcarbonyl, cycloalkylalkylcarbonyl, arylcarbonyl, arylalkylcarbonyl, carboxyl, alkoxycarbonyl, alkenyloxycarbonyl, cycloalkoxycarbonyl, cycloalkylalkoxycarbonyl, aryloxycarbonyl, arylalkoxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, alkoxyaminocarbonyl, alkenyloxycarbonylamino, cycloalkoxycarbonylamino, aryloxycarbonylamino, arylalkoxycarbonylamino, halogen, haloalkyl, haloalkenyl, unsubstituted or substituted mono- or dialkylamino, haloalkoxy, haloalkenyloxy, haloalkylthio, haloalkenylthio, haloalkylamino, haloalkenylamino, haloalkylsulfonyl, haloalkenylsulfonyl, haloalkylsulfoxyl, haloalkenylsulfoxyl, haloalkylcarbonyl, haloalkenylcarbonyl, haloalkoxycarbonyl, haloalkenyloxycarbonyl, haloalkylaminocarbonyl, haloalkenylaminocarbonyl, haloalkoxycarbonylamino, haloalkenyloxycarbonylamino, cyano or nitro.

Especially preferred substituents are hydrogen, alkyl, alkenyl, cycloalkyl, cycloalkylalkyl, aryl, arylalkyl, hydroxyl, alkoxy, cycloalkoxy, aryloxy, thio, alkylthio, cycloalkylthio, arylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, cycloalkylamino, sulfonyl, alkylsulfonyl, cycloalkylsulfonyl, arylsulfonyl, sulfoxyl, alkylsulfoxyl, arylsulfoxyl, alkylcarbonyl, arylcarbonyl, carboxyl, alkoxycarbonyl, aryloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, alkoxyaminocarbonyl, aryloxycarbonylamino, halogen, haloalkyl, haloalkoxy, haloalkylthio, haloalkylamino, haloalkylsulfonyl, haloalkylsulfoxyl, haloalkylcarbonyl, haloalkoxycarbonyl, haloalkoxycarbonylamino, cyano or nitro.

Preferred with a view to their biological activity are compounds of the general formula 1 where X is oxygen.

Further preferred compounds of the general formula 1 are those where $R^1$ is hydrogen or unsubstituted or substituted alkoxycarbonyl.

Other preferred compounds of the general formula 1 are those where $R^1$ is hydrogen or alkoxycarbonyl having 1 to 6 carbon atoms which can be mono- or polysubstituted by fluorine, chlorine or bromine.

Especially preferred compounds of the formula 1 are those where $R^1$ is hydrogen, methoxycarbonyl or ethoxycarbonyl.

Preferred compounds of the general formula 1 are, moreover, those where $R^2$ is alkyl having 1 to 6 carbon atoms, especially preferably methyl, ethyl, isopropyl or tertiary butyl; or cycloalkyl having 3 to 6 carbon atoms, especially preferably cyclopropyl or 1-methylcyclopropyl; or aryl, it being possible for this radical to have attached to it one or more of the following groups:

alkyl, alkoxy, alkylthio, it being possible for these radicals to be partially or fully halogenated, or halogen, especially preferably 3-trifluoromethylaryl, 2,4-difluoroaryl; hetaryl or heterocyclyl, it being possible for these radicals to be partially or fully halogenated or to have attached to them one or more of the following groups: alkyl, alkoxy or aryl, especially preferably 1,3-benzodioxole, 2,2-difluoro-1,3-benzodioxole, 1,3-benzoxathiole, 3,3-dioxo-1,3-benzoxathiole, benzoxazole, pyrazolyl or thienyl.

In addition, preferred compounds of the general formula 1 are those where $R^3$ is a radical of the general formula 2b or 2d,

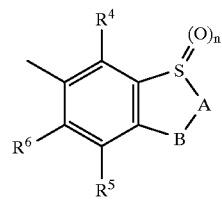

2b

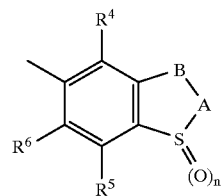

2d where n, A, B and the substituents $R^4$, $R^5$ and $R^6$ have the following meanings:

n is zero, one or two, preferably one or two, especially preferably two,

A is a chain ($-CR^7R^8-$), ($-CR^7R^8-CR^9R^{10}-$), ($-CR^7=CR^8-$), ($-CR^7R^8-CR^7=CR^8-$) or a nitrogen atom which, in turn, can be substituted by hydrogen, $C_1-C_6$-alkyl, preferably methyl, ethyl, propyl, 1-methylethyl, butyl, 2-methylpropyl, pentyl or hexyl; $C_2-C_6$-alkenyl, preferably ethenyl, 2-propenyl, 2-butenyl or 3-butenyl; unsubstituted or substituted aryl, preferably phenyl or naphthyl or aryl-$C_1-C_6$-alkyl; $C_1-C_6$-alkoxy, preferably methyloxy, ethyloxy, propyloxy, 1-methylethyloxy, butyloxy, 2-methylpropyloxy, pentyloxy or hexyloxy; halogen, preferably fluorine, chlorine, bromine or iodine; haloalkyl, preferably chloromethyl, dichloromethyl, trichloromethyl, fluoromethyl, difluoromethyl, trifluoromethyl, chlorofluoromethyl, dichlorofluoromethy, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl; or haloalkoxy, preferably chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,-trichloroethyloxy.

B is a group consisting of C=O, C=NR$^{11}$, CR$^{12}-$NR$^{13}$R$^{14}$, CR$^{12}-$OR$^{15}$, CR$^{16}$R$^{17}$, CR$^{12}-$SR$^{15}$, or is 1,3-dioxanyl or 1,3-dioxolanyl, each of which is substituted by hydrogen or $C_1-C_6$-alkyl, or is a hetero atom selected from the group consisting of oxygen, sulfur or nitrogen, it being possible for the nitrogen, in turn, to be substituted by hydrogen, $C_1$–$C_6$-alkyl, preferably methyl, ethyl, propyl, 1-methylethyl, butyl, 2-methylpropyl, pentyl or hexyl; $C_2$–$C_6$-alkenyl, preferably ethenyl, 2-propenyl, 2-butenyl or 3-butenyl; unsubstituted or substituted aryl, preferably phenyl or naphthyl or aryl-$C_1$–$C_6$-alkyl; $C_1$–$C_6$-alkoxy, preferably methyloxy, ethyloxy, propyloxy, 1-methylethyloxy, butyloxy, 2-methylpropyloxy, pentyloxy or hexyloxy; halogen, preferably fluorine, chlorine, bromine or iodine; $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2,2-trichloroethyl or pentafluoroethyl; or $C_1$–$C_6$-haloalkoxy, preferably chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy;

$R^4$–$R^6$ can be identical or different and independently of one another are hydrogen, $C_1$–$C_6$-alkyl, preferably methyl, ethyl, propyl, 1-methylethyl, butyl, 2-methylpropyl, pentyl or hexyl; $C_2$–$C_6$-alkenyl, preferably ethenyl, 2-propenyl, 2-butenyl or 3-butenyl; $C_2$–$C_6$-alkynyl, preferably ethynyl, 2-propynyl, 2-butynyl or 3-butynyl; $C_3$–$C_6$-cycloalkyl, preferably cyclopropyl, cyclobutyl, cyclopentyl or cyclohexyl, $C_3$–$C_6$-cycloalkyl-$C_1$–$C_6$-alkyl, $C_3$–$C_6$-cycloalkyl-$C_2$–$C_6$-alkenyl, $C_3$–$C_6$-cycloalkyl-$C_2$–$C_6$-alkynyl, aryl, preferably phenyl or naphthyl, aryl-$C_1$–$C_6$-alkyl, aryl-$C_2$–$C_6$-alkenyl, aryl-$C_2$–$C_6$-alkynyl; hydroxyl, $C_1$–$C_6$-alkoxy, preferably methyloxy, ethyloxy, propyloxy, 1-methylethyloxy, butyloxy, pentyloxy or hexyloxy, $C_2$–$C_6$-alkenyloxy, preferably ethenyloxy, 2-propenyloxy, 2-butenyloxy or 3-butenyloxy; $C_2$–$C_6$-alkynyloxy, preferably ethynyloxy, 2-propynyloxy, 2-butynyloxy or 3-butynyloxy; $C_3$–$C_6$-cycloalkoxy, preferably cyclopropyloxy, cyclobutyloxy, cyclopentyloxy or cyclohexyloxy, $C_3$–$C_6$-cycloalkyl-$C_1$–$C_6$-alkoxy, $C_3$–$C_6$-cycloalkyl-$C_2$–$C_6$-alkynyloxy; aryloxy, preferably phenoxy or naphthyloxy, aryl-$C_1$–$C_6$-alkoxy, aryl-$C_2$–$C_6$-alkenyloxy, aryl-$C_2$–$C_6$-alkynyloxy; thio; $C_1$–$C_6$-alkylthio, preferably methylthio, ethylthio, propylthio, 1-methylethylthio, butylthio, pentylthio or hexylthio; $C_2$–$C_6$-alkenylthio, preferably ethenylthio, 2-propenylthio, 2-butenylthio or 3-butenylthio; $C_2$–$C_6$-alkynylthio, preferably ethynylthio, 2-propinyltio, 2-butynylthio or 3-butynylthio; $C_3$–$C_6$-cycloalkylthio, preferably cyclopropylthio, cyclobutylthio, cyclopentylthio or cyclohexylthio, $C_3$–$C_6$-cycloalkyl-$C_1$–$C_6$-alkylthio, $C_3$–$C_6$-cycloalkyl-$C_2$–$C_6$-alkenylthio, $C_3$–$C_6$-cycloalkyl-$C_2$–$C_6$-alkynylthio; arylthio, preferably phenylthio or naphthylthio, aryl-$C_1$–$C_6$-alkylthio, aryl-$C_2$–$C_6$-alkenylthio, aryl-$C_2$–$C_6$-alkynylthio; amino, unsubstituted or substituted mono- or di-$C_1$–$C_6$-alkylamino, unsubstituted or substituted mono- or diarylamino, unsubstituted or substituted N—$C_1$–$C_6$-alkyl-N-arylamino, it being possible for alkyl and aryl to be identical or different; sulfonyl; $C_1$–$C_6$-alkylsulfonyl, preferably methylsulfonyl, ethylsulfonyl, propylsulfonyl, 1-methylethylsulfonyl, butylsulfonyl, 2-methylpropylsulfonyl, pentylsulfonyl or hexylsulfonyl; $C_3$–$C_6$-cycloalkylsulfonyl, preferably cyclopropylsulfonyl, cyclobutylsulfonyl, cyclopentylsulfonyl or cyclohexylsulfonyl, $C_3$–$C_6$-cycloalkyl-$C_1$–$C_6$-alkylsulfonyl, $C_3$–$C_6$-cycloalkyl-$C_2$–$C_6$-alkenylsulfonyl, $C_3$–$C_6$-cycloalkyl-$C_2$–$C_6$-alkynylsulfonyl; arylsulfonyl, preferably phenylsulfonyl or naphthylsulfonyl, aryl-$C_1$–$C_6$-alkylsulfonyl, aryl-$C_2$–$C_6$-alkenylsulfonyl, aryl-$C_2$–$C_6$-alkynylsulfonyl; aminosulfonyl, unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, sulfoxyl; $C_1$–$C_6$-alkylsulfoxyl, preferably methylsulfoxyl, ethylsulfoxyl, propylsulfoxyl, 1-methylethylsulfoxyl, butylsulfoxyl, 2-methylpropylsulfoxyl, pentylsulfoxyl or hexylsulfoxyl; $C_3$–$C_6$-cycloalkylsulfoxyl, preferably cyclopropylsulfoxyl, cyclobutylsulfoxyl, cyclopentylsulfoxyl or cyclohexylsulfoxyl, $C_3$–$C_6$-cycloalkyl-$C_1$–$C_6$-alkylsulfoxyl, $C_3$–$C_6$-cycloalkyl-$C_2$–$C_6$-alkenylsulfoxyl, $C_3$–$C_6$-cycloalkyl-$C_2$–$C_6$-alkynylsulfoxyl; arylsulfoxyl, preferably phenylsulfoxyl or naphthylsulfoxyl, aryl-$C_1$–$C_6$-alkylsulfoxyl, aryl-$C_2$–$C_6$-alkenylsulfoxyl, aryl-$C_2$–$C_6$-alkynylsulfoxyl; $C_1$–$C_6$-alkylcarbonyl, preferably methylcarbonyl, ethylcarbonyl, propylcarbonyl, 1-methylethylcarbonyl, butylcarbonyl, 2-methylpropylcarbonyl, pentylcarbonyl or hexylcarbonyl; $C_2$–$C_6$-alkenylcarbonyl, preferably ethenylcarbonyl, 2-propenylcarbonyl, 2-butenylcarbonyl or 3-butenylcarbonyl; $C_2$–$C_6$-alkynylcarbonyl, preferably ethynylcarbonyl, 2-propynylcarbonyl, 2-butynylcarbonyl or 3-butynylcarbonyl; $C_3$–$C_6$-cycloalkylcarbonyl, preferably cyclopropylcarbonyl, cyclobutylcarbonyl, cyclopentylcarbonyl or cyclohexylcarbonyl, $C_3$–$C_6$-cycloalkyl-$C_1$–$C_6$-alkylcarbonyl, $C_3$–$C_6$-cycloalkyl-$C_2$–$C_6$-alkenylcarbonyl, $C_3$–$C_6$-cycloalkyl-$C_2$–$C_6$-alkynylcarbonyl; arylcarbonyl, preferably phenylcarbonyl or naphthylcarbonyl, aryl-$C_1$–$C_6$-alkylcarbonyl, aryl-$C_2$–$C_6$-alkenylcarbonyl, aryl-$C_2$–$C_6$-alkynylcarbonyl; carboxyl; $C_1$–$C_6$-alkoxycarbonyl, methyloxycarbonyl, ethyloxycarbonyl, propyloxycarbonyl, 1-methylethyloxycarbonyl, butyloxycarbonyl, pentyloxycarbonyl or hexyloxycarbonyl, $C_2$–$C_6$-alkenyloxycarbonyl, $C_2$–$C_6$-alkynyloxycarbonyl, $C_3$–$C_6$-cycloalkoxycarbonyl, cyclopropyloxycarbonyl, cyclobutyloxycarbonyl, cyclopentyloxycarbonyl or cyclohexyloxycarbonyl, $C_3$–$C_6$-cycloalkyl-$C_1$–$C_6$-alkoxycarbonyl, $C_3$–$C_6$-cycloalkyl-$C_2$–$C_6$-alkenyloxycarbonyl, $C_3$–$C_6$-cycloalkyl-$C_2$–$C_6$-alkynyloxycarbonyl; aryloxycarbonyl, preferably phenyloxycarbonyl or naphthyloxycarbonyl, aryl-$C_1$–$C_6$-alkoxycarbonyl, aryl-$C_2$–$C_6$-alkenyloxycarbonyl, aryl-$C_2$–$C_6$-alkynyloxycarbonyl; aminocarbonyl; unsubstituted or substituted mono- or di-$C_1$–$C_6$-alkylaminocarbonyl, unsubstituted or substituted mono- or diarylaminocarbonyl, unsubstituted or substituted N—$C_1$–$C_6$-alkyl-N-arylaminocarbonyl, it being possible for alkyl and aryl to be identical or different, unsubstituted or substituted mono- or di-$C_1$–$C_6$-alkylcarbonylamino, unsubstituted or substituted mono- or diarylcarbonylamino, unsubstituted or substituted N—$C_1$–$C_6$-alkyl-N-arylcarbonylamino, it being possible for alkyl and aryl to be identical or different, $C_1$–$C_6$-alkoxyaminocarbonyl, preferably methyloxyaminocarbonyl, ethyloxyaminocarbonyl, propyloxyaminocarbonyl, 1-methylethyloxyaminocarbonyl, butyloxyaminocarbonyl, 2-methylpropyloxyaminocarbonyl, pentyloxyaminocarbonyl or hexyloxyaminocarbonyl; $C_2$–$C_6$-alkenyloxycarbonylamino, preferably ethylenoxyaminocarbonyl, 2-propenyloxyaminocarbonyl, 2-butenyloxyaminocarbonyl or 3-butenyloxyaminocarbonyl; $C_2$–$C_6$-alkynyloxycarbonylamino, preferably ethynyloxyaminocarbonyl, 2-propynyloxyaminocarbonyl, 2-butynyloxyaminocarbonyl or 3-butynyloxyaminocarbonyl; $C_3$–$C_6$-cycloalkoxyaminocarbonyl, preferably cyclopropyloxyaminocarbonyl, cyclobutyloxyaminocarbonyl, cyclopentyloxyaminocarbonyl or cyclohexyloxyaminocarbonyl, $C_3$–$C_6$-cycloalkyl-$C_1$–$C_6$-alkoxyaminocarbonyl, $C_3$–$C_6$-cycloalkyl-$C_2$–$C_6$-alkenyloxyaminocarbonyl, $C_3$–$C_6$-cycloalkyl-$C_1$–$C_6$-alkynyloxyaminocarbonyl; aryloxyaminocarbonyl, preferably phenyloxyaminocarbonyl or naphthyloxyaminocarbonyl, aryl-$C_1$–$C_6$-alkoxyaminocarbonylamino, aryl-$C_2$–$C_6$-alkenyloxyaminocarbonyl, aryl-$C_2$–$C_6$-alkynyloxyaminocarbonyl; halogen, preferably fluorine, chlorine, bromine or iodine; $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_2$–$C_6$-haloalkenyl, $C_2$–$C_6$-haloalkynyl; $C_1$–$C_6$-haloalkoxy, preferably chloromethyl, dichloromethyl, trichloromethyl, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy or pentafluoroethyloxy, $C_2$–$C_6$-haloalkenyloxy, $C_2$–$C_6$-haloalkynyloxy; $C_1$–$C_6$-haloalkylthio, preferably chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, $C_2$–$C_6$-haloalkenylthio, $C_2$–$C_6$-haloalkynylthio; $C_1$–$C_6$-haloalkylamino, preferably chloromethylamino, dichloromethylamino, trichloromethylamino, fluoromethylamino, difluoromethylamino, trifluoromethylamino, chlorofluoromethylamino, dichlorofluoromethylamino, chlorodifluoromethylamino, 1-fluoroethylamino, 2-fluoroethylamino, 2,2-difluoroethylamino, 2,2,2-trifluoroethylamino, 2-chloro-2-fluoroethylamino, 2-chloro-2,2-difluoroethylamino, 2,2-dichloro-2-fluoroethylamino, 2,2,2-trichloroethylamino or pentafluoroethylamino, $C_2$–$C_6$-haloalkenylamino, $C_2$–$C_6$-haloalkynylamino, $C_1$–$C_6$-haloalkylsulfonyl, preferably chloromethylsulfonyl, dichloromethylsulfonyl, trichloromethylsulfonyl, fluoromethylsulfonyl, difluoromethylsulfonyl, trifluoromethylsulfonyl, chlorofluoromethylsulfonyl, dichlorofluoromethylsulfonyl, chlorodifluoromethylsulfonyl, 1-fluoroethylsulfonyl, 2-fluoroethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or pentafluoroethylsulfonyl, $C_2$–$C_6$-haloalkenylsulfonyl, $C_2$–$C_6$-haloalkynylsulfonyl; $C_1$–$C_6$-haloalkylcarbonyl, preferably chloromethylcarbonyl, dichloromethylcarbonyl, trichloromethylcarbonyl, fluoromethylcarbonyl, difluoromethylcarbonyl, trifluoromethylcarbonyl, chlorofluoromethylcarbonyl, dichlorofluoromethylcarbonyl, chlorodifluoromethylcarbonyl, 1-fluoroethylcarbonyl, 2-fluoroethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2-2-2-trichloroethylcarbonyl or pentafluoroethylcarbonyl, $C_2$–$C_6$-haloalkenylcarbonyl, $C_2$–$C_6$-haloalkynylcarbonyl; $C_1$–$C_6$-haloalkoxycarbonyl, preferably chloromethyloxycarbonyl, dichloromethyloxycarbonyl, trichloromethyloxycarbonyl, fluoromethyloxycarbonyl, difluoromethyloxycarbonyl, trifluoromethyloxycarbonyl, chlorofluoromethyloxycarbonyl, dichlorofluoromethyloxycarbonyl, chlorodifluoromethyloxycarbonyl, 1-fluoroethyloxycarbonyl, 2-fluoroethyloxycarbonyl, 2,2-difluoroethyloxycarbonyl, 2,2,2-trifluoroethyloxycarbonyl, 2-chloro-2-fluoroethyloxycarbonyl, 2-chloro-2,2-difluoroethyloxycarbonyl, 2,2-dichloro-2-fluoroethyloxycarbonyl, 2,2,2-trichloroethyloxycarbonyl or pentafluoroethyloxycarbonyl, $C_2$–$C_6$-haloalkenyloxycarbonyl, $C_2$–$C_6$-haloalkynyloxycarbonyl; $C_1$–$C_6$-haloalkylaminocarbonyl, preferably chloromethylaminocarbonyl, dichloromethylaminocarbonyl, trichloromethylaminocarbonyl, fluoromethylaminocarbonyl, difluoromethylaminocarbonyl, trifluoromethylaminocarbonyl, chlorofluoromethylaminocarbonyl, dichlorofluoromethylaminocarbonyl, chlorodifluoromethylaminocarbonyl, 1-fluoroethylaminocarbonyl, 2-fluoroethylaminocarbonyl, 2,2-difluoroethylaminocarbonyl, 2,2,2-trifluoroethylaminocarbonyl, 2-chloro-2-fluoroethylaminocarbonyl, 2-chloro-2,2-difluoroethylaminocarbonyl, 2,2-dichloro-2-fluoroethylaminocarbonyl, 2,2,2-trichloroethylaminocarbonyl or pentafluoroethylaminocarbonyl, $C_2$–$C_6$-haloalkenylaminocarbonyl, $C_2$–$C_6$-haloalkynylaminocarbonyl; $C_1$–$C_6$-haloalkoxycarbonylamino, chloromethyloxyaminocarbonyl, dichloromethyloxycarbonyl, trichloromethyloxyaminocarbonyl, fluoromethyloxyaminocarbonyl, difluoromethyloxyaminocarbonyl, trifluoromethyloxyaminocarbonyl, chlorofluoromethyloxyaminocarbonyl, dichlorofluoromethyloxyaminocarbonyl, chlorodifluoromethyloxyaminocarbonyl, 1-fluoroethyloxyaminocarbonyl, 2-fluoroethyloxyaminocarbonyl, 2,2-difluoroethyloxyaminocarbonyl, 2,2,2-trifluoroethyloxyaminocarbonyl, 2-chloro-2-fluoroethyloxyaminocarbonyl, 2-chloro-2,2-difluoroethyloxyaminocarbonyl, 2,2-dichloro-2-fluoroethyloxyaminocarbonyl, 2,2,2-trichloroethyloxyaminocarbonyl or pentafluoroethyloxyaminocarbonyl, $C_2$–$C_6$-haloalkenyloxycarbonylamino, $C_2$–$C_6$-haloalkynyloxycarbonylamino, cyano or nitro;

$R^7$, $R^8$ independently of one another are hydrogen, $C_1$–$C_6$-alkyl, preferably methyl, ethyl, propyl, 1-methylethyl, butyl, 2-methylpropyl, pentyl or hexyl; $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2,-difluoroethyl, 2,2-dichloro-2-fluoroethyl, 2,2,2-trichloroethyl or pentafluoroethyl; $C_1$–$C_6$-alkoxy, preferably methyloxy, ethyloxy, propyloxy, 1-methylethyloxy, butyloxy, pentyloxy or hexyloxy: $C_1$–$C_6$-haloalkoxy, preferably chloromethyl, dichloromethyl, trichloromethyl, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy or pentafluoroethyloxy; unsubstituted or substituted aryl, preferably phenyl or naphthyl, it being possible for the substituents to consist of $C_1$–$C_4$-alkyl, $C_2$–$C_6$-alkenyl, $C_2$–$C_6$-alkynyl, $C_1$–$C_4$-alkoxy, $C_1$–$C_4$-haloalkoxy, $C_1$–$C_4$-haloalkyl, halogen, cyano, nitro;

$R^9$ is hydrogen, $C_1$–$C_6$-alkyl, preferably methyl, ethyl, propyl, 1-methylethyl, butyl, 2-methylpropyl, pentyl or hexyl; $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chlorofluoroethyl, 2-chloro-2,2-difluoroethyl, 2,2-dichloro-2-fluoroethyl, 2,2,2-trichloroethyl or pentafluoroethyl; $C_1$–$C_6$-alkoxy, preferably methyloxy, ethyloxy, propyloxy, 1-methylethyloxy, butyloxy, pentyloxy or hexyloxy; $C_1$–$C_6$-haloalkoxy, preferably chloromethyl, dichloromethyl, trichloromethyl, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-fluoroethyloxy, 2-chloro-2,2-difluoroethyloxy, 2,2-dichloro-2-fluoroethyloxy, 2,2,2-trichloroethyloxy or pentafluoroethyloxy; unsubstituted or substituted aryl, preferably phenyl or naphthyl, it being possible for the substituents to consist of $C_1$–$C_4$-alkyl, $C_2$–$C_6$-alkenyl, $C_2$–$C_6$-alkynyl, $C_1$–$C_4$-alkoxy, $C_1$–$C_4$-haloalkoxy, $C_1$–$C_4$-haloalkyl, halogen, cyano, nitro;

$R^{10}$ is hydrogen, $C_1$–$C_6$ alkyl, preferably methyl, ethyl, propyl, 1-methylethyl, butyl, 2-methylpropyl, pentyl or hexyl; $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2,-difluoroethyl, 2,2-dichloro-2-fluoroethyl, 2,2,2-trichloroethyl or pentafluoroethyl; $C_1$–$C_6$-alkoxy, preferably methyloxy, ethyloxy, propyloxy, 1-methylethyloxy, butyloxy, pentyloxy or hexyloxy: $C_1$–$C_6$-haloalkoxy, preferably chloromethyl, dichloromethyl, trichloromethyl, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy or pentafluoroethyloxy; unsubstituted or substituted aryl, preferably phenyl or naphthyl, it being possible for the substituents to consist of $C_1$–$C_4$-alkyl, $C_2$–$C_6$-alkenyl, $C_2$–$C_6$-alkynyl, $C_1$–$C_4$-alkoxy, $C_1$–$C_4$-haloalkoxy, $C_1$–$C_4$-haloalkyl, halogen, cyano, nitro;

$R^{11}$ is hydrogen, unsubstituted or substituted mono- or di-$C_1$–$C_6$-alkylamino, unsubstituted or substituted mono- or diarylamino or unsubstituted or substituted N—$C_1$–$C_6$-alkyl-N-arylamino, it being possible for alkyl and aryl to be identical or different; $C_1$–$C_6$-alkyl, preferably methyl, ethyl, propyl, 1-methylethyl, butyl, 2-methylpropyl, pentyl or hexyl; $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2,-difluoroethyl, 2,2-dichloro-2-fluoroethyl, 2,2,2-trichloroethyl or pentafluoroethyl; $C_1$–$C_6$-alkoxy, preferably methyloxy, ethyloxy, propyloxy, 1-methylethyloxy, butyloxy, pentyloxy or hexyloxy: $C_1$–$C_6$-haloalkoxy, preferably chloromethyl, dichloromethyl, trichloromethyl, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy or pentafluoroethyloxy; $C_2$–$C_6$-alkenyl, preferably ethenyl, 2-propenyl, 2-butenyl or 3-butenyl; $C_2$–$C_6$-alkynyl, ethynyl, 2-propynyl, 2-butynyl or 3-butynyl; $C_2$–$C_6$-haloalkenyl; unsubstituted or substituted aryl, preferably phenyl or naphthyl, it being possible for the substituents to consist of $C_1$–$C_4$-alkyl, $C_2$–$C_6$-alkynyl, $C_1$–$C_4$-alkoxy, $C_1$–$C_4$-haloalkoxy, $C_1$–$C_4$-haloalkyl, halogen, cyano, nitro; unsubstituted or substituted benzyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro; unsubstituted or substituted benzyloxy, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{12}$ is hydrogen, $C_1$–$C_6$-alkyl, preferably methyl, ethyl, propyl, 1-methylethyl, butyl, 2-methylpropyl, pentyl or hexyl; $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2- trifluoroethyl, 2-chlorofluoroethyl, 2-chloro-2,2-difluoroethyl, 2,2-dichloro-2-fluoroethyl, 2,2,2-trichloroethyl or pentafluoroethyl; $C_1$–$C_6$-alkoxy, preferably methyloxy, ethyloxy, propyloxy, 1-methylethyloxy, butyloxy, pentyloxy or hexyloxy; $C_1$–$C_6$-haloalkoxy, preferably chloromethyl, dichloromethyl, trichloromethyl, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-fluoroethyloxy, 2-chloro-2,2-difluoroethyloxy, 2,2-dichloro-2-fluoroethyloxy, 2,2,2-trichloroethyloxy or pentafluoroethyloxy; unsubstituted or substituted aryl, preferably phenyl or naphthyl, it being possible for the substituents to consist of $C_1$–$C_4$-alkyl, $C_2$–$C_6$-alkenyl, $C_2$–$C_6$-alkynyl, $C_1$–$C_4$-alkoxy, $C_1$–$C_4$-haloalkoxy, $C_1$–$C_4$-haloalkyl, halogen, cyano, nitro;

$R^{13}$, $R^{14}$ independently of one another are hydrogen, $C_1$–$C_6$-alkyl, preferably methyl, ethyl, propyl, 1-methylethyl, butyl, 2-methylpropyl, pentyl or hexyl; $C_2$–$C_6$-alkenyl, preferably ethenyl, 2-propenyl, 2-butenyl or 3-butenyl, $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2,-difluoroethyl, 2,2-dichloro-2-fluoroethyl, 2,2,2-trichloroethyl or pentafluoroethyl; $C_2$–$C_6$-haloalkenyl, $C_1$–$C_6$-alkoxy, preferably methyloxy, ethyloxy, propyloxy, 1-methylethyloxy, butyloxy, pentyloxy or hexyloxy; $C_1$–$C_6$-haloalkoxy, preferably chloromethyl, dichloromethyl, trichloromethyl, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy or pentafluoroethyloxy; unsubstituted or substituted aryl, preferably phenyl or naphthyl, it being possible for the substituents to consist of $C_1$–$C_4$-alkyl, $C_2$–$C_6$-alkenyl, $C_2$–$C_6$-alkynyl, $C_1$–$C_4$-alkoxy, $C_1$–$C_4$-haloalkoxy, $C_1$–$C_4$-haloalkyl, halogen, cyano, nitro; and unsubstituted or substituted benzyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{15}$ is hydrogen, $C_1$–$C_6$-alkyl, preferably methyl, ethyl, propyl, 1-methylethyl, butyl, 2-methylpropyl, pentyl or hexyl; $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2,-difluoroethyl, 2,2-dichloro-2-fluoroethyl, 2,2,2-trichloroethyl or pentafluoroethyl; unsubstituted or substituted aryl, preferably phenyl or naphthyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro; unsubstituted or substituted benzyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^6$, $R^{17}$ independently of one another are hydrogen, $C_1$–$C_6$-alkyl; preferably methyl, ethyl, propyl, 1-methylethyl, butyl, 2-methylpropyl, pentyl or hexyl; unsubstituted or substituted aryl, preferably phenyl or naphthyl, it being possible for the substituents to consist of one to three halogens, $C_1$–$C_4$-alkyl, $C_1$–$C_4$-alkoxy, $C_1$–$C_4$-haloalkoxy, nitro.

Other especially preferred compounds of the general formula 1 are those where $R^3$ is a radical of the general formula 2b or 2d,

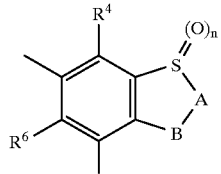

2b

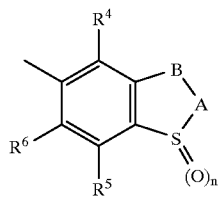

2d where n, A and B have the abovementioned meanings and $R^4$–$R^6$ have the following meanings:

$R^4$–$R^6$ can be identical or different and independently of one another are hydrogen, alkyl, cycloalkyl, aryl, hydroxyl, alkoxy, cycloalkoxy, aryloxy, thio, alkylthio, cycloalkylthio, arylthio, amino, unsubstituted or substituted mono- or dialkylamino or mono- or diarylamino or N-alkyl-N-arylamino, it being possible for alkyl and aryl to be identical or different, cycloalkylamino, sulfonyl, alkylsulfonyl, cycloalkylsulfonyl, arylsulfonyl, sulfoxyl, alkylsulfoxyl, cycloalkylsulfoxyl, arylsulfoxyl, alkylcarbonyl, cycloalkylcarbonyl, arylcarbonyl, carboxyl, alkoxycarbonyl, cycloalkoxycarbonyl, aryloxycarbonyl, aminocarbonyl, unsubstituted or substituted mono- or dialkylaminocarbonyl or mono- or diarylaminocarbonyl or N-alkyl-N-arylaminocarbonyl, it being possible for alkyl and aryl to be identical or different, alkoxyaminocarbonyl, cycloalkoxycarbonylamino, aryloxycarbonylamino, halogen, haloalkyl, haloalkoxy, haloalkylthio, haloalkylamino, haloalkylsulfonyl, haloalkylsulfoxyl, haloalkylcarbonyl, haloalkoxycarbonyl, haloalkylaminocarbonyl, haloalkoxycarbonylamino, cyano or nitro.

Preferred are also compounds of the general formula 1 where $R^3$ is a radical of the general formula 2b or 2d

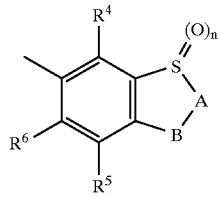

2b

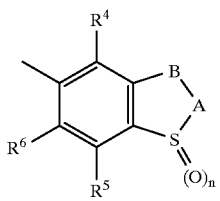

2d

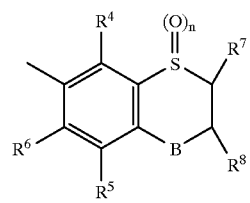

2g where n, A and B have the abovementioned meanings and $R^4$–$R^6$ have the following meanings:

$R^4$–$R^6$ can be identical or different and independently of one another are hydrogen, alkyl, hydroxyl, alkoxy, sulfonyl, sulfonylalkyl, halogen, haloalkyl, cyano or nitro.

Furthermore, preferred compounds of the general formula 1 are also those where $R^3$ is a radical of the formula 2e,

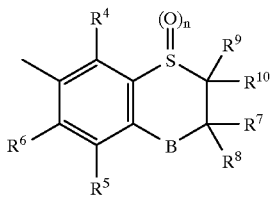

2e where $R^5$ and $R^6$ are hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and $R^4$ is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and n, B, $R^7$, RB, $R^9$ and $R^{10}$ have the meanings given in claim 1.

Further preferred compounds of the general formula 1 are also those where $R^3$ is a radical of the formula 2f

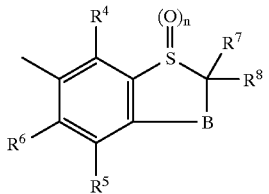

2f where $R^5$ and $R^6$ are hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and $R^4$ is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and n, B, $R^7$ and $R^8$ have the meanings given in claim 1.

Furthermore, the preferred compounds of the general formula 1 are also those where $R^3$ is a radical of the formula 2g where $R^4$ and $R^5$ are hydrogen, $C_1$–$C_6$-alkyl, $C_2$–$C_6$-alkenyl, $C_2$–$C^6$-alkynyl, $C_1$–$C_4$-alkoxy, $C_1$–$C_4$-haloalkyl, $C_1$–$C_4$-haloalkoxy, halogen, nitro or cyano and $R^4$ is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and n, B, $R^7$ and $R^8$ have the meanings given in claim 1.

Furthermore, other preferred compounds of the general formula 1 are those where $R^3$ is a radical of the formula 2a–d

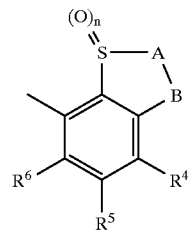

2a

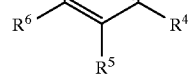

2b

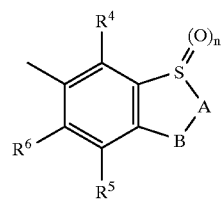

2c

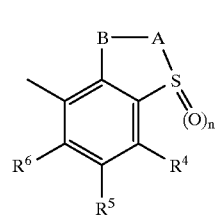

2d where n is one or two and B is $CR^{12}$—$OR^{15}$, $R^{12}$ and $R^{15}$ have the meanings given in claim 1.

Furthermore, other preferred compounds of the general formula 1 are those where $R^3$ is a radical of the formula 2b or 2d

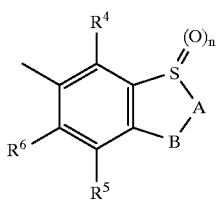

2b

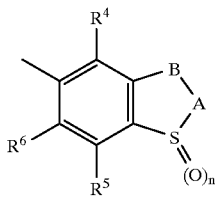

2d where n, B, $R^4$, $R^5$ and $R^6$ have the meanings given in claim 1 and A is a nitrogen atom which, in turn, can be substituted by hydrogen, $C_2$–$C_6$-alkyl, $C_2$–$C_6$-alkenyl, unsubstituted or substituted aryl or aryl-$C_1$–$C_6$-alkyl, $C_1$–$C_6$-alkoxy, halogen, $C_1$–$C_6$-haloalkyl or $C_1$–$C_6$-haloalkoxy.

Furthermore, other preferred compounds of the general formula 1 are those where $R^3$ is a radical of the formulae 2b or 2d

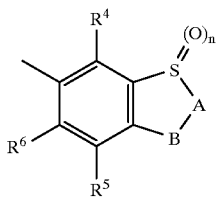

2b

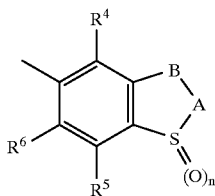

2d where n, $R^4$, $R^5$ and $R^6$ have the meanings given in claim 1 and A is a nitrogen atom which, in turn, can be substituted by hydrogen, $C_1$–$C_6$-alkyl, $C_2$–$C_6$-alkenyl, unsubstituted or substituted aryl or aryl-$C_1$–$C_6$-alkyl, $C_1$–$C_6$-alkoxy, halogen, $C_1$–$C_6$-haloalkyl or $C_1$–$C_6$-haloalkoxy and B is C=O.

Other preferred compounds of the general formula 1 are those where the substituents are selected from among a combination of the preferred substituents mentioned above.

4-Benzoylisothiazoles of the general formula 1 can be obtained a) by reacting the haloisothiazole compounds 3

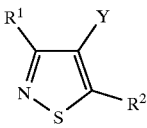

3 where $R^1$ and $R^2$ have the abovementioned meanings and Y is halogen, preferably chlorine, bromine or iodine, with elemental magnesium, an organomagnesium or an organolithium compound and with a carboxylic acid derivative of the general formula 4

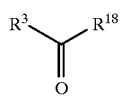

4 where $R^3$ has the abovementioned meaning and $R^{18}$ is halogen, preferably chlorine, bromine or iodine, or N-alkoxy-N-alkylamino, preferably N-methoxy-N-methylamino or cyano, in a temperature range of from −78° C. to 111° C., preferably in a temperature range of from −20° C. to 111° C., in the presence of an inert solvent (A. Alberola, F. Alonso, P. Cuadrado, M. C. Sanudo, Synth. Commun. 17 (1987)1207), or b) by reacting a halobenzene of the general formula 5 5

5 where $R^3$ has the abovementioned meaning and Y is halogen, preferably chlorine, bromine or iodine, with elemental magnesium, an organomagnesium or an organolithium compound and with an isothiazolecarboxylic acid derivative of the general formula 6a or 6b,

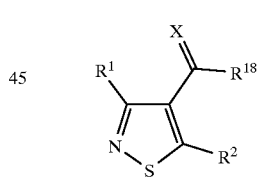

6a

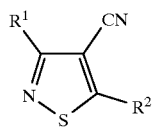

6b where X, $R^1$ and $R^2$ have the abovementioned meanings and $R^{18}$ is halogen, preferably chlorine, bromine or iodine, or N-alkoxy-N-alkylamino, preferably N-methoxy-N-methylamino, in a temperature range of from −78° C. to 111° C., preferably in a temperature range of from −20° C. to 111° C., in the presence of an inert solvent (A. Alberola, F. Alonso, P. Cuadrado, M. C. Sanudo, J. Heterocyclic Chem. 25 (1988) 235).

The haloisothiazole compounds 3 are synthesized by halogenating isothiazole compounds of the general formula 7

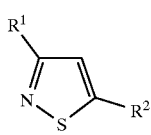

where $R^1$ and $R^2$ have the abovementioned meanings by processes known from the literature (of which the following may be mentioned as representatives: a. A. Alberola, F. Alonso, P. Cuadrado, M. C. Sanudo, Synth. Commun. 17 (1987) 1207; b. Vasilevskii, Izv. Akad. Nauk. SSSR Ser. Khim. (1975) 616).

Isothiazole compounds of the general formula 7 are known and are similarly synthesized by methods known from the literature (of which the following may be mentioned as representatives: a. D. N. McGregor. U. Corbin, J. E. Swigor, I. C. Cheney, Tetrahedron 25 (1968) 389; b. F. Lucchesini, N. Picci, M. Pocci, Heterocycles 29 (1989) 97).

The isothiazolecarboxylic acid derivatives of the general formula 6b are synthesized by reacting the haloisothiazole compounds 3 with inorganic cyanides, for example copper (I) cyanide, by processes known from the literature (of which the following may be mentioned as representatives: A. Alberola, F. Alonso, P. Cuadrado, M. C. Sanudo, J. Heterocyclic Chem. 25 (1988) 235). The corresponding isothiazolecarboxylic acid derivatives of the general formula 6a can be prepared by methods known from the literature starting from isothiazolecarboxylic acid derivatives of the general formula 6b.

Preferred organomagnesium compounds are alkylmagnesium halides, such as, for example, methylmagnesium bromide, ethylmagnesium bromide, methylmagnesium chloride or ethylmagnesium chloride. Suitable organolithium compounds are preferably aliphatic lithium compounds, such as lithium diisopropylamide, n-butyl- or sec-butyllithium.

The selection of the organic solvent depends on the starting materials employed. In general, any inert solvent is suitable. Preferred inert solvents are aliphatic, cyclic or acyclic ethers, such as, for example, diethyl ether, tetrahydrofuran, dioxane or 1,2-dimethoxyethane. In addition, inert aromatic solvents such as benzene or toluene are also used.

The starting materials are normally reacted with each other in stoichiometric amounts. However, it may be advantageous to employ one of the starting materials in an excess of from 0.1 to 10 mol equivalents, for example to improve the yield.

Benzoic acids of the formula 4 can be prepared as follows:

Benzoyl halides such as, for example, benzoyl chlorides of the formula 4

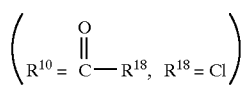

are prepared in a manner known per se by reacting the benzoic acids of the formula 4

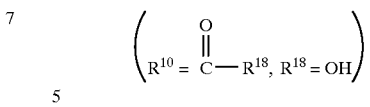

with thionyl chloride.

The benzoic acids of the formula 4

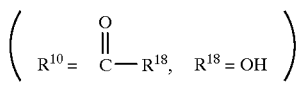

can be prepared in a known manner from the corresponding esters of the formula 4

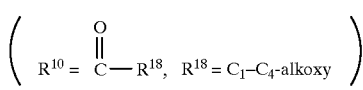

by means of acidic or basic hydrolysis.

The intermediates of the formula 4 which are not already known can be prepared by processes known from the literature.

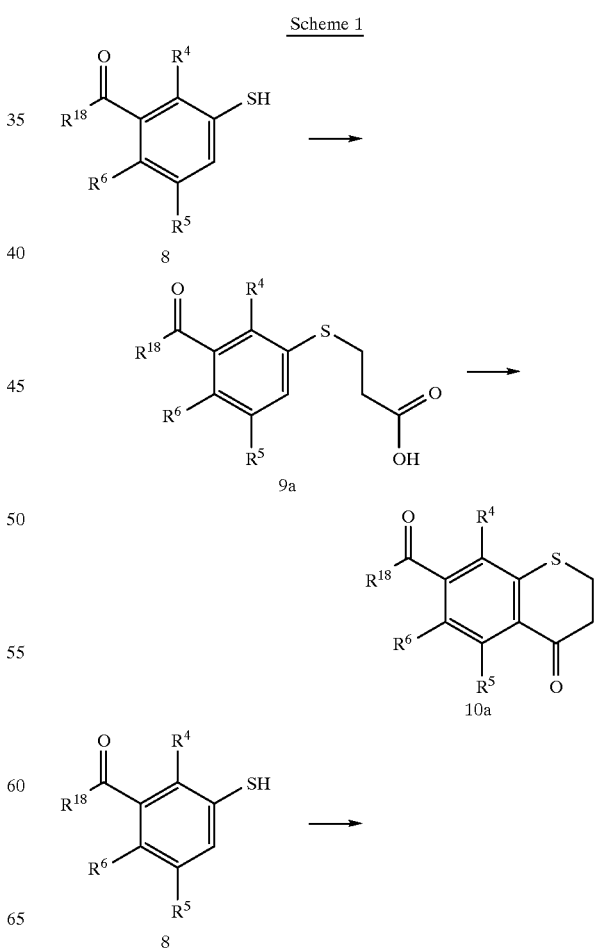

Scheme 1

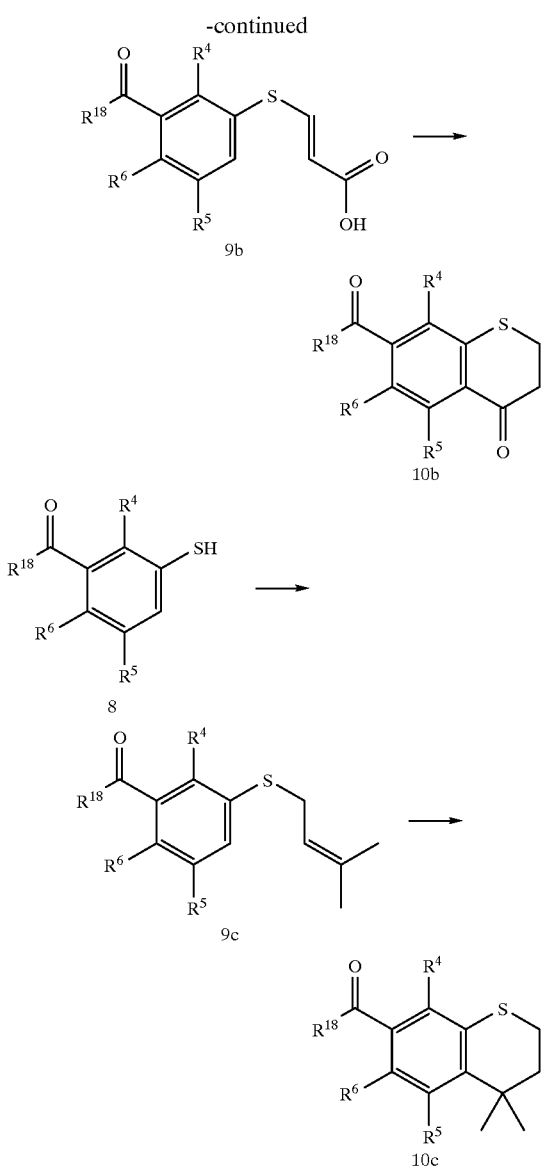

Thus, for example, arylthio compounds 8 can be reacted with substituted haloalkenyl as described in J. Med. Chem. 1984, 27, 1516, with substituted alkynylcarboxylic acids as described in J. Org. Chem. 1980, 45, 4611 or J. Am. Chem. Soc. 1983, 105, 883, substituted haloalkylcarboxylic acids as described in Chem. Ber. 1925, 58, 1612 in the presence of a base such as alkali metal hydroxide, alkali metal hydride or alkali metal carbonate, as shown in Scheme 1. The resulting compounds 9 are cyclized to give 10 under Friedel-Crafts conditions with an addition of a Lewis acid or a protonic acid. Preferred Lewis acids are $AlCl_3$ or $SnCl_4$, and preferred protonic acids are polyphosphoric acids and sulfuric acids, as described in J. Chem. 1981, 59, 199; Chem. Ber. 1925, 58, 1625; Chem. Ber. 1926, 59, 1074; Phosph. and Sulf. 1984, 19, 31.

Thiochromenone acids can furthermore be prepared for example by eliminating hydrogen halide from 3-halothiochromanone acids, or, for example, by reacting substituted thiophenol acids with substituted a-alkylacetoacetates in the presence of phosphorus pentoxide as describedin Ann. Chem. 1964, 680, 40.

The arylthio compounds 8 can be obtained, for example, via a Sandmeyer reaction from the corresponding anilines which, in turn, are synthesized by reducing suitable nitro compounds as described in Organikum 19th Edition, 1992, 552 et seq.

In the event that, for example, A is ($—CR^7R^8—$) or ($—CR^7R^8CR^9R^{10}—$), B is C=O and $R^{18}$ is $C_1$–$C_4$-alkoxy, the thiochromanone ester, or dihydrobenzothiophene ester, can be prepared as described in Scheme 1 by alkylating the arylthio compound 8 with halopropionic acid or haloacetic acid in solvent or water in the presence of one of the abovementioned bases and cyclizing the product to give 10.

The reactants and the base are expediently employed in equimolar amounts. The reaction mixture is stirred at preferably 20–100° C., in particular at 20–40° C. Working-up is carried out, for example, in such a manner that the reaction mixture is poured into water, the aqueous phase is acidified with mineral acids such as hydrochloric acid or sulfuric acid, and the product of interest is filtered off with suction or extracted with methylene chloride or ethyl acetate, dried and freed from the solvent. The ester can be reacted without further purification.

Stirring of 9 in, for example, polyphosphoric acid at 40°–140° C., in particular at 70–100° C., or activation of the carboxylic acid by converting it into the acid chloride and stirring with 2–6, in particular 3.5 to 4.5, mol equivalent of a Lewis acid such as, for example, $AlCl_3$ or $SnCl_4$ in a solvent or stirring with or in sulfuric acid gives, after known work-up, ie. addition of ice-water and filtration of the product of interest with suction or extraction of the aqueous phase with ethyl acetate or methylene chloride, drying and removing the solvent, an intermediate of the formula 4.

In the event that, for example, A is an ethylene group(— $CR^7$=$CR^{8-}$), B is C=O and $R^{18}$ is $C_1$–$C_4$-alkoxy, the thiochromenone ester can be prepared for example by reacting an arylthio compound with an acetylenecarboxylic acid derivative in water or solvent at 0–140° C. Working-up is carried out in a known manner by adding water and dilute mineral acid such as, for example, hydrochloric acid. The product of interest is either filtered off with suction or obtained by extraction with ethylene chloride or ethyl acetate, followed by drying and removing the solvent.

The intermediates of the formula 4 can be functionalized further by reactions known from the literature, such as reduction as described by Jerry March, Advanced Organic Chemistry, Fourth Ed., eg. p.910 et seq., oximation as described by Jerry March, "Advanced Organic Chemistry, Fourth Ed., eg. p. 934, 935, 1039, 1226, 405 et seq., conversion into imines and amines as described by Jerry March, Advanced Organic Chemistry, Fourth Ed., ketalization, alkylation, halogenation, elimination and oxidation as described by Jerry March, Advanced Organic Chemistry, Fourth Ed.

The acids of the 3-alkoxy-1,2-benzisothiazole 1,1-dioxides or 3-alkoxy-1,2-benzisothiazoles can be obtained starting from corresponding saccharin derivatives or 1,2-benzisothiazoles for example by reacting them with $PCl_5$, $POCl_3$ or chlorine and alcohol, if appropriate in the presence of an auxiliary base such as, for example, triethylamine, this process being described, for example, in U.S. Pat. No. 4,571,429, Arch. Pharm. 1984, 317, 807, U.S. Pat. No. 4461901, U.S. Pat. No. 450916, J. Med. Chem. 1986, 29, 359. Saccharincarboxylic acids can be obtained by processes known from the literature as described in Ann. Chem. 427, 231, 1922, Chem. Ber. 13, 1980, 1554, Chem. Ber. 25, 1892, 1740, German Laid-Open Application DE-A 3607343, German Patent Application P 44 27 995.7.

The derivatives of the benzo-1,4-oxathine acids which are not already known, for example from J. Org. Chem. 1968, 33, 456, can be synthesized for example by reacting the corresponding phenol derivatives as described in Chem. Comm., 1975, 451, J. Org. Chem. 1974, 39, 1811, J. Am. Chem. Soc. 1954, 76, 1068 or by combination of, for example, substitution reaction on halogen-substituted thiophenol derivatives and subsequent reactions such as, for example, oxidation, reduction or addition as described in J. Het. Chem. 1983, 20, 867.

The benzoic acids of the formula 4 can also be obtained by reacting the corresponding bromine- or iodine-substituted compound of the formula 11

Scheme 2

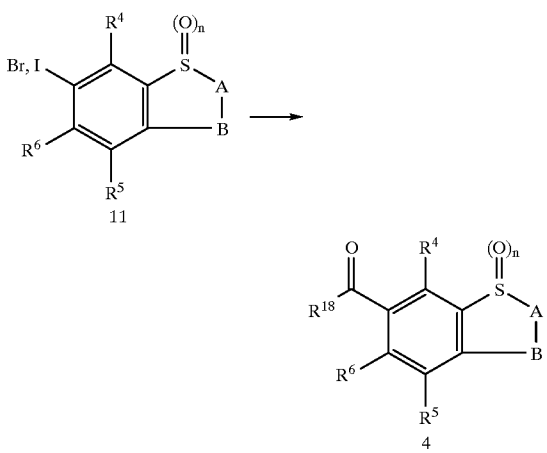

11

4 where $R^{18}$ is OH, $C_1$–$C_4$-alkoxy and
A, B, $R^4$, $R^5$ and $R^6$ have the abovementioned meanings with carbon monoxide and water under elevated pressure in the presence of palladium, nickel, cobalt or rhodium transition metal catalysts and a base.

The catalysts nickel, cobalt, rhodium and, in particular, palladium can exist in the form of metals or in the form of customary salts, such as in the form of halogen compounds, eg. $PdCl_2$, $RhCl_3.H_2O$, acetates, eg. $Pd(OAc)_2$, cyanides and the like, in the known valence states. They may also be present as metal complexes with tertiary phosphines, metal alkylcarbonyls, metal carbonyls, eg. $CO_2(CO)8$, $Ni(CO)_4$, metal carbonyl complexes with tertiary phosphines, eg. $(PPh_3)_2Ni(CO)_2$, or transition metal salts complexed with tertiary phosphines. The last-mentioned embodiment is particularly preferred in the case of palladium as the catalyst. The nature of the phosphine ligands can be varied within broad limits. For example, they may be represented by the following formulae:

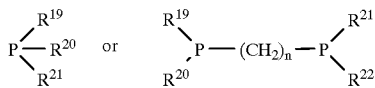

where n is a number 1, 2, 3 or 4 and the radicals from $R^{19}$ to $R^{22}$ are lower alkyl, eg. $C_1$–$C_6$-alkyl, aryl, $C_1$–$C_4$-alkylaryl, eg. benzyl, phenethyl or aryloxy. Aryl is, for example, naphthyl, anthryl and, preferably, unsubstituted or substituted phenyl; while care must be taken that the substituents are inert toward the carboxylation reaction, they can be varied within a broad range and embrace all inert C-organic radicals such as $C_1$–$C_6$-alkyl radicals, eg. methyl, carboxyl radicals such as COOH, COOM (M being, for example, an alkali metal, alkaline earth metal or ammonium salt), or C-organic radicals which are bonded via oxygen, such as $C_1$–$C_6$-alkoxy radicals.

The phosphine complexes can be prepared in a known manner, for example as described in the documents mentioned at the outset. For example, the starting material is a customary commercially available metal salt such as $PdCl_2$ or $Pd(OCOCH_3)_2$, and the phosphine, eg. $P(C_6H_5)_3$, $P(n-C_4H_9)_3$, $PCH_3(C_6H_5)_2$, 1,2-bis(diphenylphosphino)ethane, is added.

The amount of phosphine based on the transition metal is normally 0 to 20, in particular 0.1 to 10, mol equivalents, especially preferably 1 to 5 mol equivalents.

The amount of transition metal is not critical. Of course, a smaller amount, eg. from 0.1 to 10 mol %, in particular 1 to 5 mol %, based on the starting material 3 or 4, will preferably be used in order to save costs.

To prepare the benzoic acids 4

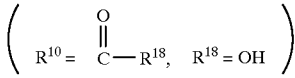

$$\left( R^{10} = \overset{O}{\underset{\|}{C}} - R^{18}, \quad R^{18} = OH \right)$$

the reaction is carried out with carbon monoxide and at least equimolar amounts of water, based on the starting materials 10. The reactant water may simultaneously also act as the solvent, ie. the maximum amount is not critical.

However, depending on the nature of the starting materials and on the catalysts used, it may be advantageous to use, as solvent, not the reactant but a different inert solvent or the base used for the carboxylation.

Suitable inert solvents are solvents which are customary for carboxylation reactions, such as hydrocarbons, eg. toluene, xylene, hexane, pentane, cyclohexane, ethers, eg. methyl tert-butyl ether, tetrahydrofuran, dioxane, dimethoxyethane, substituted amides such as dimethylformamide, persubstituted ureas such as tetra-$C_1$–$C_4$-alkylureas, or nitriles such as benzonitrile or acetonitrile.

In a preferred embodiment of the process, one of the reactants, in particular the base, is used in an excess, thus dispensing with additional solvent.

Bases which are suitable for the process are all inert bases which are capable of binding the hydrogen iodide or hydrogen bromide which is liberated during the reaction. Examples are tertiary amines such as tert-alkylamines, eg. trialkylamines such as triethylamine, cyclic amines such as N-methylpyridine or N,N'-dimethylpiperazine, pyridine, alkali metal carbonates or alkali metal hydrogen carbonates, or tetralkyl-substituted urea derivatives such as tetra-$C_1$–$C_4$-alkylurea, eg. tetramethylurea.

The amount of base is not critical, 1 to 10, in particular 1 to 5, mol normally being used. When using the base simultaneously as the solvent, the amount is generally selected so that the reactants are dissolved while avoiding unnecessarily high excesses for practical reasons, to save costs, to be able to use small reaction vessels and to allow maximum contact between the reactants.

The carbon monoxide pressure during the reaction is adjusted so that there is always an excess of CO over 10. The carbon monoxide pressure at room temperature is preferably from 1 to 250 bar, in particular 5 to 150 bar, of CO.

The carbonylation is generally carried out at from 20 to 250° C., in particular at from 30 to 150° C., either continuously or batchwise. In the case of batchwise preparation, it is expedient continuously to inject carbon monoxide onto the reaction mixture so as to maintain a constant pressure.

Those arylhalogen compounds 11 used as starting compounds which are not already known can be prepared simply by a suitable combination of known syntheses and following above-described reaction sequences.

Examples of especially preferred compounds of the general formula 1 are compiled in the Tables which follow. The definitions of the radicals are not only especially preferred in the specific combination of radicals, but in each case also in isolation.

TABLE 1

[Structure: Compound 12 — benzothiophene with (O)n on sulfur, R4, OCH3, R5 substituents; linked via carbonyl to isothiazole bearing cyclopropyl]

| No. | n | R⁴ | R⁵ |
|---|---|---|---|
| 12.1 | 0 | H | H |
| 12.2 | 0 | Cl | F |
| 12.3 | 0 | Cl | Cl |
| 12.4 | 0 | Cl | Br |
| 12.5 | 0 | Cl | CH₃ |
| 12.6 | 0 | Cl | C₂H₅ |
| 12.7 | 0 | Cl | nC₃H₇ |
| 12.8 | 0 | Cl | iC₃H₇ |
| 12.9 | 0 | Cl | nC₄H₉ |
| 12.10 | 0 | Cl | tC₄H₉ |
| 12.11 | 0 | Cl | Ph |
| 12.12 | 0 | Cl | OH |
| 12.13 | 0 | Cl | OCH₃ |
| 12.14 | 0 | Cl | OC₂H₅ |
| 12.15 | 0 | Cl | O(nC₃H₇) |
| 12.16 | 0 | Cl | O(iC₃H₇) |
| 12.17 | 0 | Cl | O(nC₄H₉) |
| 12.18 | 0 | Cl | O(tC₄H₉) |
| 12.19 | 0 | Cl | OPh |
| 12.20 | 0 | Cl | SH |
| 12.21 | 0 | Cl | SCH₃ |
| 12.22 | 0 | Cl | SC₂H₅ |
| 12.23 | 0 | Cl | S(nC₃H₇) |
| 12.24 | 0 | Cl | S(iC₃H₇) |
| 12.25 | 0 | Cl | S(nC₄H₉) |
| 12.26 | 0 | Cl | S(tC₄H₉) |
| 12.27 | 0 | Cl | SPh |
| 12.28 | 0 | Cl | CCl₃ |
| 12.29 | 0 | Cl | CH₂F |
| 12.30 | 0 | Cl | CHF₂ |
| 12.31 | 0 | Cl | CF₃ |
| 12.32 | 0 | Cl | CF₂CHF₂ |
| 12.33 | 0 | Cl | SO₃H |
| 12.34 | 0 | Cl | SO₂CH₃ |
| 12.35 | 0 | Cl | SO₂C₂H₅ |
| 12.36 | 0 | Cl | SO₂(nC₃H₇) |
| 12.37 | 0 | Cl | SO₂(iC₃H₇) |
| 12.38 | 0 | Cl | SO₂(nC₄H₉) |
| 12.39 | 0 | Cl | SO₂(tC₄H₉) |
| 12.40 | 0 | Cl | SO₂Ph |
| 12.41 | 0 | Cl | NH₂ |
| 12.42 | 0 | Cl | NHCH₃ |
| 12.43 | 0 | Cl | NCH₃Ph |
| 12.44 | 0 | Cl | N(CH₃)₂ |
| 12.45 | 0 | Cl | NPh₂ |
| 12.46 | 0 | Cl | CN |
| 12.47 | 0 | Cl | NO₂ |
| 12.48 | 0 | CH₃ | F |
| 12.49 | 0 | CH₃ | Cl |
| 12.50 | 0 | CH₃ | Br |
| 12.51 | 0 | CH₃ | CH₃ |
| 12.52 | 0 | CH₃ | C₂H₅ |
| 12.53 | 0 | CH₃ | nC₃H₇ |
| 12.54 | 0 | CH₃ | iC₃H₇ |
| 12.55 | 0 | CH₃ | nC₄H₉ |
| 12.56 | 0 | CH₃ | tC₄H₉ |
| 12.57 | 0 | CH₃ | Ph |
| 12.58 | 0 | CH₃ | OH |
| 12.59 | 0 | CH₃ | OCH₃ |
| 12.60 | 0 | CH₃ | OC₂H₅ |
| 12.61 | 0 | CH₃ | O(nC₃H₇) |
| 12.62 | 0 | CH₃ | O(iC₃H₇) |
| 12.63 | 0 | CH₃ | O(nC₄H₉) |
| 12.64 | 0 | CH₃ | O(tC₄H₉) |
| 12.65 | 0 | CH₃ | OPh |
| 12.66 | 0 | CH₃ | SH |
| 12.67 | 0 | CH₃ | SCH₃ |
| 12.68 | 0 | CH₃ | SC₂H₅ |
| 12.69 | 0 | CH₃ | S(nC₃H₇) |
| 12.70 | 0 | CH₃ | S(iC₃H₇) |
| 12.71 | 0 | CH₃ | S(nC₄H₉) |
| 12.72 | 0 | CH₃ | S(tC₄H₉) |
| 12.73 | 0 | CH₃ | SPh |
| 12.74 | 0 | CH₃ | CCl₃ |
| 12.75 | 0 | CH₃ | CH₂F |
| 12.76 | 0 | CH₃ | CHF₂ |
| 12.77 | 0 | CH₃ | CF₃ |
| 12.78 | 0 | CH₃ | CF₂CHF₂ |
| 12.79 | 0 | CH₃ | SO₃H |
| 12.80 | 0 | CH₃ | SO₂CH₃ |
| 12.81 | 0 | CH₃ | SO₂C₂H₅ |
| 12.82 | 0 | CH₃ | SO₂(nC₃H₇) |
| 12.83 | 0 | CH₃ | SO₂(iC₃H₇) |
| 12.84 | 0 | CH₃ | SO₂(nC₄H₉) |
| 12.85 | 0 | CH₃ | SO₂(tC₄H₉) |
| 12.86 | 0 | CH₃ | SO₂Ph |
| 12.87 | 0 | CH₃ | NH₂ |
| 12.88 | 0 | CH₃ | NHCH₃ |
| 12.89 | 0 | CH₃ | NCH₃Ph |
| 12.90 | 0 | CH₃ | N(CH₃)₂ |
| 12.91 | 0 | CH₃ | NPh₂ |
| 12.92 | 0 | CH₃ | CN |
| 12.93 | 0 | CH₃ | NO₂ |
| 12.94 | 2 | Cl | F |
| 12.95 | 2 | Cl | Cl |
| 12.96 | 2 | Cl | Br |
| 12.97 | 2 | Cl | CH₃ |
| 12.98 | 2 | Cl | C₂H₅ |
| 12.99 | 2 | Cl | nC₃H₇ |
| 12.100 | 2 | Cl | iC₃H₇ |
| 12.101 | 2 | Cl | nC₄H₉ |
| 12.102 | 2 | Cl | tC₄H₉ |
| 12.103 | 2 | Cl | Ph |
| 12.104 | 2 | Cl | OH |
| 12.105 | 2 | Cl | OCH₃ |
| 12.106 | 2 | Cl | OC₂H₅ |
| 12.107 | 2 | Cl | O(nC₃H₇) |
| 12.108 | 2 | Cl | O(iC₃H₇) |
| 12.109 | 2 | Cl | O(nC₄H₉) |
| 12.110 | 2 | Cl | O(tC₄H₉) |
| 12.111 | 2 | Cl | OPh |
| 12.112 | 2 | Cl | SH |
| 12.113 | 2 | Cl | SCH₃ |
| 12.114 | 2 | Cl | SC₂H₅ |
| 12.115 | 2 | Cl | S(nC₃H₇) |
| 12.116 | 2 | Cl | S(iC₃H₇) |
| 12.117 | 2 | Cl | S(nC₄H₉) |
| 12.118 | 2 | Cl | S(tC₄H₉) |
| 12.119 | 2 | Cl | SPh |
| 12.120 | 2 | Cl | CCl₃ |
| 12.121 | 2 | Cl | CH₂F |
| 12.122 | 2 | Cl | CHF₂ |
| 12.123 | 2 | Cl | CF₃ |
| 12.124 | 2 | Cl | CF₂CHF₂ |

TABLE 1-continued

Structure 12: isoxazole-cyclopropyl group connected via C=O to a benzothiophene ring system with R⁴, (O)ₙ on S, OCH₃, and R⁵ substituents.

| No. | n | R⁴ | R⁵ |
|---|---|---|---|
| 12.125 | 2 | Cl | SO₃H |
| 12.126 | 2 | Cl | SO₂CH₃ |
| 12.127 | 2 | Cl | SO₂C₂H₅ |
| 12.128 | 2 | Cl | SO₂(nC₃H₇) |
| 12.129 | 2 | Cl | SO₂(iC₃H₇) |
| 12.130 | 2 | Cl | SO₂(nC₄H₉) |
| 12.131 | 2 | Cl | SO₂(tC₄H₉) |
| 12.132 | 2 | Cl | SO₂Ph |
| 12.133 | 2 | Cl | NH₂ |
| 12.134 | 2 | Cl | NHCH₃ |
| 12.135 | 2 | Cl | NCH₃Ph |
| 12.136 | 2 | Cl | N(CH₃)₂ |
| 12.137 | 2 | Cl | NPh₂ |
| 12.138 | 2 | Cl | CN |
| 12.139 | 2 | Cl | NO₂ |
| 12.140 | 2 | CH₃ | F |
| 12.141 | 2 | CH₃ | Cl |
| 12.142 | 2 | CH₃ | Br |
| 12.143 | 2 | CH₃ | CH₃ |
| 12.144 | 2 | CH₃ | C₂H₅ |
| 12.145 | 2 | CH₃ | nC₃H₇ |
| 12.146 | 2 | CH₃ | iC₃H₇ |
| 12.147 | 2 | CH₃ | nC₄H₉ |
| 12.148 | 2 | CH₃ | tC₄H₉ |
| 12.149 | 2 | CH₃ | Ph |
| 12.150 | 2 | CH₃ | OH |
| 12.151 | 2 | CH₃ | OCH₃ |
| 12.152 | 2 | CH₃ | OC₂H₅ |
| 12.153 | 2 | CH₃ | O(nC₃H₇) |
| 12.154 | 2 | CH₃ | O(iC₃H₇) |
| 12.155 | 2 | CH₃ | O(nC₄H₉) |
| 12.156 | 2 | CH₃ | O(tC₄H₉) |
| 12.157 | 2 | CH₃ | OPh |
| 12.158 | 2 | CH₃ | SH |
| 12.159 | 2 | CH₃ | SCH₃ |
| 12.160 | 2 | CH₃ | SC₂H₅ |
| 12.161 | 2 | CH₃ | S(nC₃H₇) |
| 12.162 | 2 | CH₃ | S(iC₃H₇) |
| 12.163 | 2 | CH₃ | S(nC₄H₉) |
| 12.164 | 2 | CH₃ | S(tC₄H₉) |
| 12.165 | 2 | CH₃ | SPh |
| 12.166 | 2 | CH₃ | CCl₃ |
| 12.167 | 2 | CH₃ | CH₂F |
| 12.168 | 2 | CH₃ | CHF₂ |
| 12.169 | 2 | CH₃ | CF₃ |
| 12.170 | 2 | CH₃ | CF₂CHF₂ |
| 12.171 | 2 | CH₃ | SO₃H |
| 12.172 | 2 | CH₃ | SO₂CH₃ |
| 12.173 | 2 | CH₃ | SO₂C₂H₅ |
| 12.174 | 2 | CH₃ | SO₂(nC₃H₇) |
| 12.175 | 2 | CH₃ | SO₂(iC₃H₇) |
| 12.176 | 2 | CH₃ | SO₂(nC₄H₉) |
| 12.177 | 2 | CH₃ | SO₂(tC₄H₉) |
| 12.178 | 2 | CH₃ | SO₂Ph |
| 12.179 | 2 | CH₃ | NH₂ |
| 12.180 | 2 | CH₃ | NHCH₃ |
| 12.181 | 2 | CH₃ | NCH₃Ph |
| 12.182 | 2 | CH₃ | N(CH₃)₂ |
| 12.183 | 2 | CH₃ | NPh₂ |
| 12.184 | 2 | CH₃ | CN |
| 12.185 | 2 | CH₃ | NO₂ |

TABLE 2

Structure 13: isoxazole-cyclopropyl group connected via C=O to a benzisothiazolone ring system (N-CH₃, SO₂) with R⁴ and R⁵ substituents.

| No. | R⁴ | R⁵ |
|---|---|---|
| 13.1 | H | H |
| 13.2 | Cl | F |
| 13.3 | Cl | Cl |
| 13.4 | Cl | Br |
| 13.5 | Cl | CH₃ |
| 13.6 | Cl | C₂H₅ |
| 13.7 | Cl | nC₃H₇ |
| 13.8 | Cl | iC₃H₇ |
| 13.9 | Cl | nC₄H₉ |
| 13.10 | Cl | tC₄H₉ |
| 13.11 | Cl | Ph |
| 13.12 | Cl | OH |
| 13.13 | Cl | OCH₃ |
| 13.14 | Cl | OC₂H₅ |
| 13.15 | Cl | O(nC₃H₇) |
| 13.16 | Cl | O(iC₃H₇) |
| 13.17 | Cl | O(nC₄H₉) |
| 13.18 | Cl | O(tC₄H₉) |
| 13.19 | Cl | OPh |
| 13.20 | Cl | SH |
| 13.21 | Cl | SCH₃ |
| 13.22 | Cl | SC₂H₅ |
| 13.23 | Cl | S(nC₃H₇) |
| 13.24 | Cl | S(iC₃H₇) |
| 13.25 | Cl | S(nC₄H₉) |
| 13.26 | Cl | S(tC₄H₉) |
| 13.27 | Cl | SPh |
| 13.28 | Cl | CCl₃ |
| 13.29 | Cl | CH₂F |
| 13.30 | Cl | CHF₂ |
| 13.31 | Cl | CF₃ |
| 13.32 | Cl | CF₂CHF₂ |
| 13.33 | Cl | SO₃H |
| 13.34 | Cl | SO₂CH₃ |
| 13.35 | Cl | SO₂C₂H₅ |
| 13.36 | Cl | SO₂(nC₃H₇) |
| 13.37 | Cl | SO₂(iC₃H₇) |
| 13.38 | Cl | SO₂(nC₄H₉) |
| 13.39 | Cl | SO₂(tC₄H₉) |
| 13.40 | Cl | SO₂Ph |
| 13.41 | Cl | NH₂ |
| 13.42 | Cl | NHCH₃ |
| 13.43 | Cl | NCH₃Ph |
| 13.44 | Cl | N(CH₃)₂ |
| 13.45 | Cl | NPh₂ |
| 13.46 | Cl | CN |
| 13.47 | Cl | NO₂ |
| 13.48 | CH₃ | F |
| 13.49 | CH₃ | Cl |
| 13.50 | CH₃ | Br |
| 13.51 | CH₃ | CH₃ |
| 13.52 | CH₃ | C₂H₅ |
| 13.53 | CH₃ | nC₃H₇ |
| 13.54 | CH₃ | iC₃H₇ |
| 13.55 | CH₃ | nC₄H₉ |
| 13.56 | CH₃ | tC₄H₉ |
| 13.57 | CH₃ | Ph |
| 13.58 | CH₃ | OH |
| 13.59 | CH₃ | OCH₃ |
| 13.60 | CH₃ | OC₂H₅ |
| 13.61 | CH₃ | O(nC₃H₇) |
| 13.62 | CH₃ | O(iC₃H₇) |

TABLE 2-continued

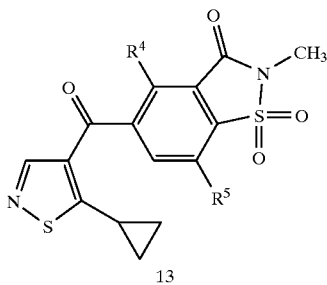

13

| No. | R⁴ | R⁵ |
|---|---|---|
| 13.63 | $CH_3$ | $O(nC_4H_9)$ |
| 13.64 | $CH_3$ | $O(tC_4H_9)$ |
| 13.65 | $CH_3$ | OPh |
| 13.66 | $CH_3$ | SH |
| 13.67 | $CH_3$ | $SCH_3$ |
| 13.68 | $CH_3$ | $SC_2H_5$ |
| 13.69 | $CH_3$ | $S(nC_3H_7)$ |
| 13.70 | $CH_3$ | $S(iC_3H_7)$ |
| 13.71 | $CH_3$ | $S(nC_4H_9)$ |
| 13.72 | $CH_3$ | $S(tC_4H_9)$ |
| 13.73 | $CH_3$ | SPh |
| 13.74 | $CH_3$ | $CCl_3$ |
| 13.75 | $CH_3$ | $CH_2F$ |
| 13.76 | $CH_3$ | $CHF_2$ |
| 13.77 | $CH_3$ | $CF_3$ |
| 13.78 | $CH_3$ | $CF_2CHF_2$ |
| 13.79 | $CH_3$ | $SO_3H$ |
| 13.80 | $CH_3$ | $SO_2CH_3$ |
| 13.81 | $CH_3$ | $SO_2C_2H_5$ |
| 13.82 | $CH_3$ | $SO_2(nC_3H_7)$ |
| 13.83 | $CH_3$ | $SO_2(iC_3H_7)$ |
| 13.84 | $CH_3$ | $SO_2(nC_4H_9)$ |
| 13.85 | $CH_3$ | $SO_2(tC_4H_9)$ |
| 13.86 | $CH_3$ | $SO_2Ph$ |
| 13.87 | $CH_3$ | $NH_2$ |
| 13.88 | $CH_3$ | $NHCH_3$ |
| 13.89 | $CH_3$ | $NCH_3Ph$ |
| 13.90 | $CH_3$ | $N(CH_3)_2$ |
| 13.91 | $CH_3$ | $NPh_2$ |
| 13.92 | $CH_3$ | CN |
| 13.93 | $CH_3$ | $NO_2$ |

TABLE 3

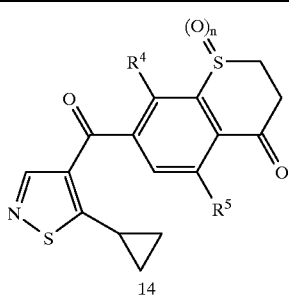

14

| No. | n | R⁴ | R⁵ |
|---|---|---|---|
| 14.1 | 0 | H | H |
| 14.2 | 0 | Cl | F |
| 14.3 | 0 | Cl | Cl |
| 14.4 | 0 | Cl | Br |
| 14.5 | 0 | Cl | $CH_3$ |
| 14.6 | 0 | Cl | $C_2H_5$ |
| 14.7 | 0 | Cl | $nC_3H_7$ |
| 14.8 | 0 | Cl | $iC_3H_7$ |
| 14.9 | 0 | Cl | $nC_4H_9$ |

TABLE 3-continued

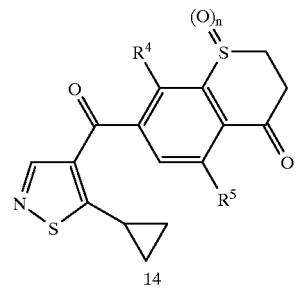

14

| No. | n | R⁴ | R⁵ |
|---|---|---|---|
| 14.10 | 0 | Cl | $tC_4H_9$ |
| 14.11 | 0 | Cl | Ph |
| 14.12 | 0 | Cl | OH |
| 14.13 | 0 | Cl | $OCH_3$ |
| 14.14 | 0 | Cl | $OC_2H_5$ |
| 14.15 | 0 | Cl | $O(nC_3H_7)$ |
| 14.16 | 0 | Cl | $O(iC_3H_7)$ |
| 14.17 | 0 | Cl | $O(nC_4H_9)$ |
| 14.18 | 0 | Cl | $O(tC_4H_9)$ |
| 14.19 | 0 | Cl | OPh |
| 14.20 | 0 | Cl | SH |
| 14.21 | 0 | Cl | $SCH_3$ |
| 14.22 | 0 | Cl | $SC_2H_5$ |
| 14.23 | 0 | Cl | $S(nC_3H_7)$ |
| 14.24 | 0 | Cl | $S(iC_3H_7)$ |
| 14.25 | 0 | Cl | $S(nC_4H_9)$ |
| 14.26 | 0 | Cl | $S(tC_4H_9)$ |
| 14.27 | 0 | Cl | SPh |
| 14.28 | 0 | Cl | $CCl_3$ |
| 14.29 | 0 | Cl | $CH_2F$ |
| 14.30 | 0 | Cl | $CHF_2$ |
| 14.31 | 0 | Cl | $CF_3$ |
| 14.32 | 0 | Cl | $CF_2CHF_2$ |
| 14.33 | 0 | Cl | $SO_3H$ |
| 14.34 | 0 | Cl | $SO_2CH_3$ |
| 14.35 | 0 | Cl | $SO_2C_2H_5$ |
| 14.36 | 0 | Cl | $SO_2(nC_3H_7)$ |
| 14.37 | 0 | Cl | $SO_2(iC_3H_7)$ |
| 14.38 | 0 | Cl | $SO_2(nC_4H_9)$ |
| 14.39 | 0 | Cl | $SO_2(tC_4H_9)$ |
| 14.40 | 0 | Cl | $SO_2Ph$ |
| 14.41 | 0 | Cl | $NH_2$ |
| 14.42 | 0 | Cl | $NHCH_3$ |
| 14.43 | 0 | Cl | $NCH_3Ph$ |
| 14.44 | 0 | Cl | $N(CH_3)_2$ |
| 14.45 | 0 | Cl | $NPh_2$ |
| 14.46 | 0 | Cl | CN |
| 14.47 | 0 | Cl | $NO_2$ |
| 14.48 | 0 | $CH_3$ | F |
| 14.49 | 0 | $CH_3$ | Cl |
| 14.50 | 0 | $CH_3$ | Br |
| 14.51 | 0 | $CH_3$ | $CH_3$ |
| 14.52 | 0 | $CH_3$ | $C_2H_5$ |
| 14.53 | 0 | $CH_3$ | $nC_3H_7$ |
| 14.54 | 0 | $CH_3$ | $iC_3H_7$ |
| 14.55 | 0 | $CH_3$ | $nC_4H_9$ |
| 14.56 | 0 | $CH_3$ | $tC_4H_9$ |
| 14.57 | 0 | $CH_3$ | Ph |
| 14.58 | 0 | $CH_3$ | OH |
| 14.59 | 0 | $CH_3$ | $OCH_3$ |
| 14.60 | 0 | $CH_3$ | $OC_2H_5$ |
| 14.61 | 0 | $CH_3$ | $O(nC_3H_7)$ |
| 14.62 | 0 | $CH_3$ | $O(iC_3H_7)$ |
| 14.63 | 0 | $CH_3$ | $O(nC_4H_9)$ |
| 14.64 | 0 | $CH_3$ | $O(tC_4H_9)$ |
| 14.65 | 0 | $CH_3$ | OPh |
| 14.66 | 0 | $CH_3$ | SH |
| 14.67 | 0 | $CH_3$ | $SCH_3$ |
| 14.68 | 0 | $CH_3$ | $SC_2H_5$ |
| 14.69 | 0 | $CH_3$ | $S(nC_3H_7)$ |
| 14.70 | 0 | $CH_3$ | $S(iC_3H_7)$ |
| 14.71 | 0 | $CH_3$ | $S(nC_4H_9)$ |

TABLE 3-continued

| No. | n | R⁴ | R⁵ |
|---|---|---|---|
| 14.72 | 0 | CH₃ | S(tC₄H₉) |
| 14.73 | 0 | CH₃ | SPh |
| 14.74 | 0 | CH₃ | CCl₃ |
| 14.75 | 0 | CH₃ | CH₂F |
| 14.76 | 0 | CH₃ | CHF₂ |
| 14.77 | 0 | CH₃ | CF₃ |
| 14.78 | 0 | CH₃ | CF₂CHF₂ |
| 14.79 | 0 | CH₃ | SO₃H |
| 14.80 | 0 | CH₃ | SO₂CH₃ |
| 14.81 | 0 | CH₃ | SO₂C₂H₅ |
| 14.82 | 0 | CH₃ | SO₂(nC₃H₇) |
| 14.83 | 0 | CH₃ | SO₂(iC₃H₇) |
| 14.84 | 0 | CH₃ | SO₂(nC₄H₉) |
| 14.85 | 0 | CH₃ | SO₂(tC₄H₉) |
| 14.86 | 0 | CH₃ | SO₂Ph |
| 14.87 | 0 | CH₃ | NH₂ |
| 14.88 | 0 | CH₃ | NHCH₃ |
| 14.89 | 0 | CH₃ | NCH₃Ph |
| 14.90 | 0 | CH₃ | N(CH₃)₂ |
| 14.91 | 0 | CH₃ | NPh₂ |
| 14.92 | 0 | CH₃ | CN |
| 14.93 | 0 | CH₃ | NO₂ |
| 14.94 | 2 | Cl | F |
| 14.95 | 2 | Cl | Cl |
| 14.96 | 2 | Cl | Br |
| 14.97 | 2 | Cl | CH₃ |
| 14.98 | 2 | Cl | C₂H₅ |
| 14.99 | 2 | Cl | nC₃H₇ |
| 14.100 | 2 | Cl | iC₃H₇ |
| 14.101 | 2 | Cl | nC₄H₉ |
| 14.102 | 2 | Cl | tC₄H₉ |
| 14.103 | 2 | Cl | Ph |
| 14.104 | 2 | Cl | OH |
| 14.105 | 2 | Cl | OCH₃ |
| 14.106 | 2 | Cl | OC₂H₅ |
| 14.107 | 2 | Cl | O(nC₃H₇) |
| 14.108 | 2 | Cl | O(iC₃H₇) |
| 14.109 | 2 | Cl | O(nC₄H₉) |
| 14.110 | 2 | Cl | O(tC₄H₉) |
| 14.111 | 2 | Cl | OPh |
| 14.112 | 2 | Cl | SH |
| 14.113 | 2 | Cl | SCH₃ |
| 14.114 | 2 | Cl | SC₂H₅ |
| 14.115 | 2 | Cl | S(nC₃H₇) |
| 14.116 | 2 | Cl | S(iC₃H₇) |
| 14.117 | 2 | Cl | S(nC₄H₉) |
| 14.118 | 2 | Cl | S(tC₄H₉) |
| 14.119 | 2 | Cl | SPh |
| 14.120 | 2 | Cl | CCl₃ |
| 14.121 | 2 | Cl | CH₂F |
| 14.122 | 2 | Cl | CHF₂ |
| 14.123 | 2 | Cl | CF₃ |
| 14.124 | 2 | Cl | CF₂CHF₂ |
| 14.125 | 2 | Cl | SO₃H |
| 14.126 | 2 | Cl | SO₂CH₃ |
| 14.127 | 2 | Cl | SO₂C₂H₅ |
| 14.128 | 2 | Cl | SO₂(nC₃H₇) |
| 14.129 | 2 | Cl | SO₂(iC₃H₇) |
| 14.130 | 2 | Cl | SO₂(nC₄H₉) |
| 14.131 | 2 | Cl | SO₂(tC₄H₉) |
| 14.132 | 2 | Cl | SO₂Ph |
| 14.133 | 2 | Cl | NH₂ |
| 14.134 | 2 | Cl | NHCH₃ |
| 14.135 | 2 | Cl | NCH₃Ph |
| 14.136 | 2 | Cl | N(CH₃)₂ |
| 14.137 | 2 | Cl | NPh₂ |
| 14.138 | 2 | Cl | CN |
| 14.139 | 2 | Cl | NO₂ |
| 14.140 | 2 | CH₃ | F |
| 14.141 | 2 | CH₃ | Cl |
| 14.142 | 2 | CH₃ | Br |
| 14.143 | 2 | CH₃ | CH₃ |
| 14.144 | 2 | CH₃ | C₂H₅ |
| 14.145 | 2 | CH₃ | nC₃H₇ |
| 14.146 | 2 | CH₃ | iC₃H₇ |
| 14.147 | 2 | CH₃ | nC₄H₉ |
| 14.148 | 2 | CH₃ | tC₄H₉ |
| 14.149 | 2 | CH₃ | Ph |
| 14.150 | 2 | CH₃ | OH |
| 14.151 | 2 | CH₃ | OCH₃ |
| 14.152 | 2 | CH₃ | OC₂H₅ |
| 14.153 | 2 | CH₃ | O(nC₃H₇) |
| 14.154 | 2 | CH₃ | O(iC₃H₇) |
| 14.155 | 2 | CH₃ | O(nC₄H₉) |
| 14.156 | 2 | CH₃ | O(tC₄H₉) |
| 14.157 | 2 | CH₃ | OPh |
| 14.158 | 2 | CH₃ | SH |
| 14.159 | 2 | CH₃ | SCH₃ |
| 14.160 | 2 | CH₃ | SC₂H₅ |
| 14.161 | 2 | CH₃ | S(nC₃H₇) |
| 14.162 | 2 | CH₃ | S(iC₃H₇) |
| 14.163 | 2 | CH₃ | S(nC₄H₉) |
| 14.164 | 2 | CH₃ | S(tC₄H₉) |
| 14.165 | 2 | CH₃ | SPh |
| 14.166 | 2 | CH₃ | CCl₃ |
| 14.167 | 2 | CH₃ | CH₂F |
| 14.168 | 2 | CH₃ | CHF₂ |
| 14.169 | 2 | CH₃ | CF₃ |
| 14.170 | 2 | CH₃ | CF₂CHF₂ |
| 14.171 | 2 | CH₃ | SO₃H |
| 14.172 | 2 | CH₃ | SO₂CH₃ |
| 14.173 | 2 | CH₃ | SO₂C₂H₅ |
| 14.174 | 2 | CH₃ | SO₂(nC₃H₇) |
| 14.175 | 2 | CH₃ | SO₂(iC₃H₇) |
| 14.176 | 2 | CH₃ | SO₂(nC₄H₉) |
| 14.177 | 2 | CH₃ | SO₂(tC₄H₉) |
| 14.178 | 2 | CH₃ | SO₂Ph |
| 14.179 | 2 | CH₃ | NH₂ |
| 14.180 | 2 | CH₃ | NHCH₃ |
| 14.181 | 2 | CH₃ | NCH₃Ph |
| 14.182 | 2 | CH₃ | N(CH₃)₂ |
| 14.183 | 2 | CH₃ | NPh₂ |
| 14.184 | 2 | CH₃ | CN |
| 14.185 | 2 | CH₃ | NO₂ |

TABLE 4

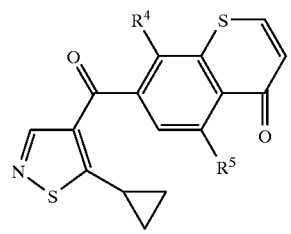

| No. | R⁴ | R⁵ |
|---|---|---|
| 15.1 | H | H |
| 15.2 | Cl | F |
| 15.3 | Cl | Cl |
| 15.4 | Cl | Br |
| 15.5 | Cl | $CH_3$ |
| 15.6 | Cl | $C_2H_5$ |
| 15.7 | Cl | $nC_3H_7$ |
| 15.8 | Cl | $iC_3H_7$ |
| 15.9 | Cl | $nC_4H_9$ |
| 15.10 | Cl | $tC_4H_9$ |
| 15.11 | Cl | Ph |
| 15.12 | Cl | OH |
| 15.13 | Cl | $OCH_3$ |
| 15.14 | Cl | $OC_2H_5$ |
| 15.15 | Cl | $O(nC_3H_7)$ |
| 15.16 | Cl | $O(iC_3H_7)$ |
| 15.17 | Cl | $O(nC_4H_9)$ |
| 15.18 | Cl | $O(tC_4H_9)$ |
| 15.19 | Cl | OPh |
| 15.20 | Cl | SH |
| 15.21 | Cl | $SCH_3$ |
| 15.22 | Cl | $SC_2H_5$ |
| 15.23 | Cl | $S(nC_3H_7)$ |
| 15.24 | Cl | $S(iC_3H_7)$ |
| 15.25 | Cl | $S(nC_4H_9)$ |
| 15.26 | Cl | $S(tC_4H_9)$ |
| 15.27 | Cl | SPh |
| 15.28 | Cl | $CCl_3$ |
| 15.29 | Cl | $CH_2F$ |
| 15.30 | Cl | $CHF_2$ |
| 15.31 | Cl | $CF_3$ |
| 15.32 | Cl | $CF_2CHF_2$ |
| 15.33 | Cl | $SO_3H$ |
| 15.34 | Cl | $SO_2CH_3$ |
| 15.35 | Cl | $SO_2C_2H_5$ |
| 15.36 | Cl | $SO_2(nC_3H_7)$ |
| 15.37 | Cl | $SO_2(iC_3H_7)$ |
| 15.38 | Cl | $SO_2(nC_4H_9)$ |
| 15.39 | Cl | $SO_2(tC_4H_9)$ |
| 15.40 | Cl | $SO_2Ph$ |
| 15.41 | Cl | $NH_2$ |
| 15.42 | Cl | $NHCH_3$ |
| 15.43 | Cl | $NCH_3Ph$ |
| 15.44 | Cl | $N(CH_3)_2$ |
| 15.45 | Cl | $NPh_2$ |
| 15.46 | Cl | CN |
| 15.47 | Cl | $NO_2$ |
| 15.48 | $CH_3$ | F |
| 15.49 | $CH_3$ | Cl |
| 15.50 | $CH_3$ | Br |
| 15.51 | $CH_3$ | $CH_3$ |
| 15.52 | $CH_3$ | $C_2H_5$ |
| 15.53 | $CH_3$ | $nC_3H_7$ |
| 15.54 | $CH_3$ | $iC_3H_7$ |
| 15.55 | $CH_3$ | $nC_4H_9$ |
| 15.56 | $CH_3$ | $tC_4H_9$ |
| 15.57 | $CH_3$ | Ph |
| 15.58 | $CH_3$ | OH |
| 15.59 | $CH_3$ | $OCH_3$ |
| 15.60 | $CH_3$ | $OC_2H_5$ |
| 15.61 | $CH_3$ | $O(nC_3H_7)$ |
| 15.62 | $CH_3$ | $O(iC_3H_7)$ |
| 15.63 | $CH_3$ | $O(nC_4H_9)$ |
| 15.64 | $CH_3$ | $O(tC_4H_9)$ |

TABLE 4-continued

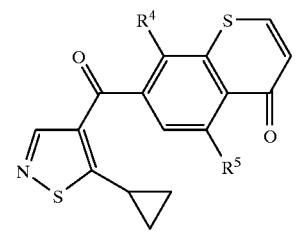

| No. | R⁴ | R⁵ |
|---|---|---|
| 15.65 | $CH_3$ | OPh |
| 15.66 | $CH_3$ | SH |
| 15.67 | $CH_3$ | $SCH_3$ |
| 15.68 | $CH_3$ | $SC_2H_5$ |
| 15.69 | $CH_3$ | $S(nC_3H_7)$ |
| 15.70 | $CH_3$ | $S(iC_3H_7)$ |
| 15.71 | $CH_3$ | $S(nC_4H_9)$ |
| 15.72 | $CH_3$ | $S(tC_4H_9)$ |
| 15.73 | $CH_3$ | SPh |
| 15.74 | $CH_3$ | $CCl_3$ |
| 15.75 | $CH_3$ | $CH_2F$ |
| 15.76 | $CH_3$ | $CHF_2$ |
| 15.77 | $CH_3$ | $CF_3$ |
| 15.78 | $CH_3$ | $CF_2CHF_2$ |
| 15.79 | $CH_3$ | $SO_3H$ |
| 15.80 | $CH_3$ | $SO_2CH_3$ |
| 15.81 | $CH_3$ | $SO_2C_2H_5$ |
| 15.82 | $CH_3$ | $SO_2(nC_3H_7)$ |
| 15.83 | $CH_3$ | $SO_2(iC_3H_7)$ |
| 15.84 | $CH_3$ | $SO_2(nC_4H_7)$ |
| 15.85 | $CH_3$ | $SO_2(tC_4H_9)$ |
| 15.86 | $CH_3$ | $SO_2Ph$ |
| 15.87 | $CH_3$ | $NH_2$ |
| 15.88 | $CH_3$ | $NHCH_3$ |
| 15.89 | $CH_3$ | $NCH_3Ph$ |
| 15.90 | $CH_3$ | $N(CH_3)_2$ |
| 15.91 | $CH_3$ | $NPh_2$ |
| 15.92 | $CH_3$ | CN |
| 15.93 | $CH_3$ | $NO_2$ |

TABLE 5

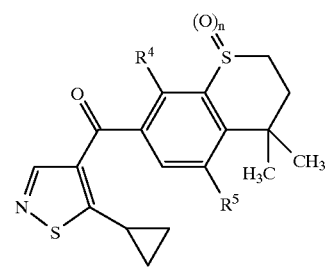

| No. | n | R⁴ | R⁵ |
|---|---|---|---|
| 16.1 | 0 | H | H |
| 16.2 | 0 | Cl | F |
| 16.3 | 0 | Cl | Cl |
| 16.4 | 0 | Cl | Br |
| 16.5 | 0 | Cl | $CH_3$ |
| 16.6 | 0 | Cl | $C_2H_5$ |
| 16.7 | 0 | Cl | $nC_3H_7$ |
| 16.8 | 0 | Cl | $iC_3H_7$ |
| 16.9 | 0 | Cl | $nC_4H_9$ |
| 16.10 | 0 | Cl | $tC_4H_9$ |
| 16.11 | 0 | Cl | Ph |
| 16.12 | 0 | Cl | OH |
| 16.13 | 0 | Cl | $OCH_3$ |
| 16.14 | 0 | Cl | $OC_2H_5$ |

TABLE 5-continued

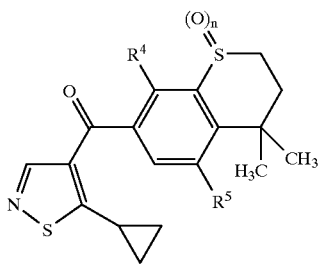

| No. | n | R⁴ | R⁵ |
|---|---|---|---|
| 16.15 | 0 | Cl | $O(nC_3H_7)$ |
| 16.16 | 0 | Cl | $O(iC_3H_7)$ |
| 16.17 | 0 | Cl | $O(nC_4H_9)$ |
| 16.18 | 0 | Cl | $O(tC_4H_9)$ |
| 16.19 | 0 | Cl | OPh |
| 16.20 | 0 | Cl | SH |
| 16.21 | 0 | Cl | $SCH_3$ |
| 16.22 | 0 | Cl | $SC_2H_5$ |
| 16.23 | 0 | Cl | $S(nC_3H_7)$ |
| 16.24 | 0 | Cl | $S(iC_3H_7)$ |
| 16.25 | 0 | Cl | $S(nC_4H_9)$ |
| 16.26 | 0 | Cl | $S(tC_4H_9)$ |
| 16.27 | 0 | Cl | SPh |
| 16.28 | 0 | Cl | $CCl_3$ |
| 16.29 | 0 | Cl | $CH_2F$ |
| 16.30 | 0 | Cl | $CHF_2$ |
| 16.31 | 0 | Cl | $CF_3$ |
| 16.32 | 0 | Cl | $CF_2CHF_2$ |
| 16.33 | 0 | Cl | $SO_3H$ |
| 16.34 | 0 | Cl | $SO_2CH_3$ |
| 16.35 | 0 | Cl | $SO_2C_2H_5$ |
| 16.36 | 0 | Cl | $SO_2(nC_3H_7)$ |
| 16.37 | 0 | Cl | $SO_2(iC_3H_7)$ |
| 16.38 | 0 | Cl | $SO_2(nC_4H_9)$ |
| 16.39 | 0 | Cl | $SO_2(tC_4H_9)$ |
| 16.40 | 0 | Cl | $SO_2Ph$ |
| 16.41 | 0 | Cl | $NH_2$ |
| 16.42 | 0 | Cl | $NHCH_3$ |
| 16.43 | 0 | Cl | $NCH_3Ph$ |
| 16.44 | 0 | Cl | $N(CH_3)_2$ |
| 16.45 | 0 | Cl | $NPh_2$ |
| 16.46 | 0 | Cl | CN |
| 16.47 | 0 | Cl | $NO_2$ |
| 16.48 | 0 | $CH_3$ | F |
| 16.49 | 0 | $CH_3$ | Cl |
| 16.50 | 0 | $CH_3$ | Br |
| 16.51 | 0 | $CH_3$ | $CH_3$ |
| 16.52 | 0 | $CH_3$ | $C_2H_5$ |
| 16.53 | 0 | $CH_3$ | $nC_3H_7$ |
| 16.54 | 0 | $CH_3$ | $iC_3H_7$ |
| 16.55 | 0 | $CH_3$ | $nC_4H_9$ |
| 16.56 | 0 | $CH_3$ | $tC_4H_9$ |
| 16.57 | 0 | $CH_3$ | Ph |
| 16.58 | 0 | $CH_3$ | OH |
| 16.59 | 0 | $CH_3$ | $OCH_3$ |
| 16.60 | 0 | $CH_3$ | $OC_2H_5$ |
| 16.61 | 0 | $CH_3$ | $O(nC_3H_7)$ |
| 16.62 | 0 | $CH_3$ | $O(iC_3H_7)$ |
| 16.63 | 0 | $CH_3$ | $O(nC_4H_9)$ |
| 16.64 | 0 | $CH_3$ | $O(tC_4H_9)$ |
| 16.65 | 0 | $CH_3$ | OPh |
| 16.66 | 0 | $CH_3$ | SH |
| 16.67 | 0 | $CH_3$ | $SCH_3$ |
| 16.68 | 0 | $CH_3$ | $SC_2H_5$ |
| 16.69 | 0 | $CH_3$ | $S(nC_3H_7)$ |
| 16.70 | 0 | $CH_3$ | $S(iC_3H_7)$ |
| 16.71 | 0 | $CH_3$ | $S(nC_4H_9)$ |
| 16.72 | 0 | $CH_3$ | $S(tC_4H_9)$ |
| 16.73 | 0 | $CH_3$ | SPh |
| 16.74 | 0 | $CH_3$ | $CCl_3$ |
| 16.75 | 0 | $CH_3$ | $CH_2F$ |
| 16.76 | 0 | $CH_3$ | $CHF_2$ |
| 16.77 | 0 | $CH_3$ | $CF_3$ |
| 16.78 | 0 | $CH_3$ | $CF_2CHF_2$ |
| 16.79 | 0 | $CH_3$ | $SO_3H$ |
| 16.80 | 0 | $CH_3$ | $SO_2CH_3$ |
| 16.81 | 0 | $CH_3$ | $SO_2C_2H_5$ |
| 16.82 | 0 | $CH_3$ | $SO_2(nC_3H_7)$ |
| 16.83 | 0 | $CH_3$ | $SO_2(iC_3H_7)$ |
| 16.84 | 0 | $CH_3$ | $SO_2(nC_4H_9)$ |
| 16.85 | 0 | $CH_3$ | $SO_2(tC_4H_9)$ |
| 16.86 | 0 | $CH_3$ | $SO_2Ph$ |
| 16.87 | 0 | $CH_3$ | $NH_2$ |
| 16.88 | 0 | $CH_3$ | $NHCH_3$ |
| 16.89 | 0 | $CH_3$ | $NCH_3Ph$ |
| 16.90 | 0 | $CH_3$ | $N(CH_3)_2$ |
| 16.91 | 0 | $CH_3$ | $NPh_2$ |
| 16.92 | 0 | $CH_3$ | CN |
| 16.93 | 0 | $CH_3$ | $NO_2$ |
| 16.94 | 2 | Cl | F |
| 16.95 | 2 | Cl | Cl |
| 16.96 | 2 | Cl | Br |
| 16.97 | 2 | Cl | $CH_3$ |
| 16.98 | 2 | Cl | $C_2H_5$ |
| 16.99 | 2 | Cl | $nC_3H_7$ |
| 16.100 | 2 | Cl | $iC_3H_7$ |
| 16.101 | 2 | Cl | $nC_4H_9$ |
| 16.102 | 2 | Cl | $tC_4H_9$ |
| 16.103 | 2 | Cl | Ph |
| 16.104 | 2 | Cl | OH |
| 16.105 | 2 | Cl | $OCH_3$ |
| 16.106 | 2 | Cl | $OC_2H_5$ |
| 16.107 | 2 | Cl | $O(nC_3H_7)$ |
| 16.108 | 2 | Cl | $O(iC_3H_7)$ |
| 16.109 | 2 | Cl | $O(nC_4H_9)$ |
| 16.110 | 2 | Cl | $O(tC_4H_9)$ |
| 16.111 | 2 | Cl | OPh |
| 16.112 | 2 | Cl | SH |
| 16.113 | 2 | Cl | $SCH_3$ |
| 16.114 | 2 | Cl | $SC_2H_5$ |
| 16.115 | 2 | Cl | $S(nC_3H_7)$ |
| 16.116 | 2 | Cl | $S(iC_3H_7)$ |
| 16.117 | 2 | Cl | $S(nC_4H_9)$ |
| 16.118 | 2 | Cl | $S(tC_4H_9)$ |
| 16.119 | 2 | Cl | SPh |
| 16.120 | 2 | Cl | $CCl_3$ |
| 16.121 | 2 | Cl | $CH_2F$ |
| 16.122 | 2 | Cl | $CHF_2$ |
| 16.123 | 2 | Cl | $CF_3$ |
| 16.124 | 2 | Cl | $CF_2CHF_2$ |
| 16.125 | 2 | Cl | $SO_3H$ |
| 16.126 | 2 | Cl | $SO_2CH_3$ |
| 16.127 | 2 | Cl | $SO_2C_2H_5$ |
| 16.128 | 2 | Cl | $SO_2(nC_3H_7)$ |
| 16.129 | 2 | Cl | $SO_2(iC_3H_7)$ |
| 16.130 | 2 | Cl | $SO_2(nC_4H_9)$ |
| 16.131 | 2 | Cl | $SO_2(tC_4H_9)$ |
| 16.132 | 2 | Cl | $SO_2Ph$ |
| 16.133 | 2 | Cl | $NH_2$ |
| 16.134 | 2 | Cl | $NHCH_3$ |
| 16.135 | 2 | Cl | $NCH_3Ph$ |
| 16.136 | 2 | Cl | $N(CH_3)_2$ |
| 16.137 | 2 | Cl | $NPh_2$ |
| 16.138 | 2 | Cl | CN |
| 16.139 | 2 | Cl | $NO_2$ |
| 16.140 | 2 | $CH_3$ | F |

TABLE 5-continued

[Structure: chromane-thione with R⁴, (O)ₙ on S, carbonyl linked to isothiazole bearing cyclopropyl; ring has H₃C, CH₃ geminal and R⁵]

| No. | n | R⁴ | R⁵ |
|---|---|---|---|
| 16.141 | 2 | CH₃ | Cl |
| 16.142 | 2 | CH₃ | Br |
| 16.143 | 2 | CH₃ | CH₃ |
| 16.144 | 2 | CH₃ | C₂H₅ |
| 16.145 | 2 | CH₃ | nC₃H₇ |
| 16.146 | 2 | CH₃ | iC₃H₇ |
| 16.147 | 2 | CH₃ | nC₄H₉ |
| 16.148 | 2 | CH₃ | tC₄H₉ |
| 16.149 | 2 | CH₃ | Ph |
| 16.150 | 2 | CH₃ | OH |
| 16.151 | 2 | CH₃ | OCH₃ |
| 16.152 | 2 | CH₃ | OC₂H₅ |
| 16.153 | 2 | CH₃ | O(nC₃H₇) |
| 16.154 | 2 | CH₃ | O(iC₃H₇) |
| 16.155 | 2 | CH₃ | O(nC₄H₉) |
| 16.156 | 2 | CH₃ | O(tC₄H₉) |
| 16.157 | 2 | CH₃ | OPh |
| 16.158 | 2 | CH₃ | SH |
| 16.159 | 2 | CH₃ | SCH₃ |
| 16.160 | 2 | CH₃ | SC₂H₅ |
| 16.161 | 2 | CH₃ | S(nC₃H₇) |
| 16.162 | 2 | CH₃ | S(iC₃H₇) |
| 16.163 | 2 | CH₃ | S(nC₄H₉) |
| 16.164 | 2 | CH₃ | S(tC₄H₉) |
| 16.165 | 2 | CH₃ | SPh |
| 16.166 | 2 | CH₃ | CCl₃ |
| 16.167 | 2 | CH₃ | CH₂F |
| 16.168 | 2 | CH₃ | CHF₂ |
| 16.169 | 2 | CH₃ | CF₃ |
| 16.170 | 2 | CH₃ | CF₂CHF₂ |
| 16.171 | 2 | CH₃ | SO₃H |
| 16.172 | 2 | CH₃ | SO₂CH₃ |
| 16.173 | 2 | CH₃ | SO₂C₂H₅ |
| 16.174 | 2 | CH₃ | SO₂(nC₃H₇) |
| 16.175 | 2 | CH₃ | SO₂(iC₃H₇) |
| 16.176 | 2 | CH₃ | SO₂(nC₄H₉) |
| 16.177 | 2 | CH₃ | SO₂(tC₄H₉) |
| 16.178 | 2 | CH₃ | SO₂Ph |
| 16.179 | 2 | CH₃ | NH₂ |
| 16.180 | 2 | CH₃ | NHCH₃ |
| 16.181 | 2 | CH₃ | NCH₃Ph |
| 16.182 | 2 | CH₃ | N(CH₃)₂ |
| 16.183 | 2 | CH₃ | NPh₂ |
| 16.184 | 2 | CH₃ | CN |
| 16.185 | 2 | CH₃ | NO₂ |

TABLE 6

[Structure: chromane with OCH₃ substituent, S with (O)ₙ, R⁴ and R⁵ on aromatic, carbonyl to isothiazole with cyclopropyl]

| No. | n | R⁴ | R⁵ |
|---|---|---|---|
| 17.1 | 0 | H | H |
| 17.2 | 0 | Cl | F |
| 17.3 | 0 | Cl | Cl |
| 17.4 | 0 | Cl | Br |
| 17.5 | 0 | Cl | CH₃ |
| 17.6 | 0 | Cl | C₂H₅ |
| 17.7 | 0 | Cl | nC₃H₇ |
| 17.8 | 0 | Cl | iC₃H₇ |
| 17.9 | 0 | Cl | nC₄H₉ |
| 17.10 | 0 | Cl | tC₄H₉ |
| 17.11 | 0 | Cl | Ph |
| 17.12 | 0 | Cl | OH |
| 17.13 | 0 | Cl | OCH₃ |
| 17.14 | 0 | Cl | OC₂H₅ |
| 17.15 | 0 | Cl | O(nC₃H₇) |
| 17.16 | 0 | Cl | O(iC₃H₇) |
| 17.17 | 0 | Cl | O(nC₄H₉) |
| 17.18 | 0 | Cl | O(tC₄H₉) |
| 17.19 | 0 | Cl | OPh |
| 17.20 | 0 | Cl | SH |
| 17.21 | 0 | Cl | SCH₃ |
| 17.22 | 0 | Cl | SC₂H₅ |
| 17.23 | 0 | Cl | S(nC₃H₇) |
| 17.24 | 0 | Cl | S(iC₃H₇) |
| 17.25 | 0 | Cl | S(nC₄H₉) |
| 17.26 | 0 | Cl | S(tC₄H₉) |
| 17.27 | 0 | Cl | SPh |
| 17.28 | 0 | Cl | CCl₃ |
| 17.29 | 0 | Cl | CH₂F |
| 17.30 | 0 | Cl | CHF₂ |
| 17.31 | 0 | Cl | CF₃ |
| 17.32 | 0 | Cl | CF₂CHF₂ |
| 17.33 | 0 | Cl | SO₃H |
| 17.34 | 0 | Cl | SO₂CH₃ |
| 17.35 | 0 | Cl | SO₂C₂H₅ |
| 17.36 | 0 | Cl | SO₂(nC₃H₇) |
| 17.37 | 0 | Cl | SO₂(iC₃H₇) |
| 17.38 | 0 | Cl | SO₂(nC₄H₉) |
| 17.39 | 0 | Cl | SO₂(tC₄H₉) |
| 17.40 | 0 | Cl | SO₂Ph |
| 14.41 | 0 | Cl | NH₂ |
| 17.42 | 0 | Cl | NHCH₃ |
| 17.43 | 0 | Cl | NCH₃Ph |
| 17.44 | 0 | Cl | N(CH₃)₂ |
| 17.45 | 0 | Cl | NPh₂ |
| 17.46 | 0 | Cl | CN |
| 17.47 | 0 | Cl | NO₂ |
| 17.48 | 0 | CH₃ | F |
| 17.49 | 0 | CH₃ | Cl |
| 17.50 | 0 | CH₃ | Br |
| 17.51 | 0 | CH₃ | CH₃ |
| 17.52 | 0 | CH₃ | C₂H₅ |
| 17.53 | 0 | CH₃ | nC₃H₇ |
| 17.54 | 0 | CH₃ | iC₃H₇ |
| 17.55 | 0 | CH₃ | nC₄H₉ |
| 17.56 | 0 | CH₃ | tC₄H₉ |
| 17.57 | 0 | CH₃ | Ph |
| 17.58 | 0 | CH₃ | OH |
| 17.59 | 0 | CH₃ | OCH₃ |
| 17.60 | 0 | CH₃ | OC₂H₅ |
| 17.61 | 0 | CH₃ | O(nC₃H₇) |
| 17.62 | 0 | CH₃ | O(iC₃H₇) |
| 17.63 | 0 | CH₃ | O(nC₄H₉) |

TABLE 6-continued

| No. | n | R⁴ | R⁵ |
|---|---|---|---|
| 17.64 | 0 | CH₃ | O(tC₄H₉) |
| 17.65 | 0 | CH₃ | OPh |
| 17.66 | 0 | CH₃ | SH |
| 17.67 | 0 | CH₃ | SCH₃ |
| 17.68 | 0 | CH₃ | SC₂H₅ |
| 17.69 | 0 | CH₃ | S(nC₃H₇) |
| 17.70 | 0 | CH₃ | S(iC₃H₇) |
| 17.71 | 0 | CH₃ | S(nC₄H₉) |
| 17.72 | 0 | CH₃ | S(tC₄H₉) |
| 17.73 | 0 | CH₃ | SPh |
| 17.74 | 0 | CH₃ | CCl₃ |
| 17.75 | 0 | CH₃ | CH₂F |
| 17.76 | 0 | CH₃ | CHF₂ |
| 17.77 | 0 | CH₃ | CF₃ |
| 17.78 | 0 | CH₃ | CF₂CHF₂ |
| 17.79 | 0 | CH₃ | SO₃H |
| 17.80 | 0 | CH₃ | SO₂CH₃ |
| 17.81 | 0 | CH₃ | SO₂C₂H₅ |
| 17.82 | 0 | CH₃ | SO₂(nC₃H₇) |
| 17.83 | 0 | CH₃ | SO₂(iC₃H₇) |
| 17.84 | 0 | CH₃ | SO₂(nC₄H₉) |
| 17.85 | 0 | CH₃ | SO₂(tC₄H₉) |
| 17.86 | 0 | CH₃ | SO₂Ph |
| 17.87 | 0 | CH₃ | NH₂ |
| 17.88 | 0 | CH₃ | NHCH₃ |
| 17.89 | 0 | CH₃ | NCH₃Ph |
| 17.90 | 0 | CH₃ | N(CH₃)₂ |
| 17.91 | 0 | CH₃ | NPh₂ |
| 17.92 | 0 | CH₃ | CN |
| 17.93 | 0 | CH₃ | NO₂ |
| 17.94 | 2 | Cl | F |
| 17.95 | 2 | Cl | Cl |
| 17.96 | 2 | Cl | Br |
| 17.97 | 2 | Cl | CH₃ |
| 17.98 | 2 | Cl | C₂H₅ |
| 17.99 | 2 | Cl | nC₃H₇ |
| 17.100 | 2 | Cl | iC₃H₇ |
| 17.101 | 2 | Cl | nC₄H₉ |
| 17.102 | 2 | Cl | tC₄H₉ |
| 17.103 | 2 | Cl | Ph |
| 17.104 | 2 | Cl | OH |
| 17.105 | 2 | Cl | OCH₃ |
| 17.106 | 2 | Cl | OC₂H₅ |
| 17.107 | 2 | Cl | O(nC₃H₇) |
| 17.108 | 2 | Cl | O(iC₃H₇) |
| 17.109 | 2 | Cl | O(nC₄H₉) |
| 17.110 | 2 | Cl | O(tC₄H₉) |
| 17.111 | 2 | Cl | OPh |
| 17.112 | 2 | Cl | SH |
| 17.113 | 2 | Cl | SCH₃ |
| 17.114 | 2 | Cl | SC₂H₅ |
| 17.115 | 2 | Cl | S(nC₃H₇) |
| 17.116 | 2 | Cl | S(iC₃H₇) |
| 17.117 | 2 | Cl | S(nC₄H₉) |
| 17.118 | 2 | Cl | S(tC₄H₉) |
| 17.119 | 2 | Cl | SPh |
| 17.120 | 2 | Cl | CCl₃ |
| 17.121 | 2 | Cl | CH₂F |
| 17.122 | 2 | Cl | CHF₂ |
| 17.123 | 2 | Cl | CF₃ |
| 17.124 | 2 | Cl | CF₂CHF₂ |
| 17.125 | 2 | Cl | SO₃H |
| 17.126 | 2 | Cl | SO₂CH₃ |
| 17.127 | 2 | Cl | SO₂C₂H₅ |
| 17.128 | 2 | Cl | SO₂(nC₃H₇) |
| 17.129 | 2 | Cl | SO₂(iC₃H₇) |
| 17.130 | 2 | Cl | SO₂(nC₄H₉) |
| 17.131 | 2 | Cl | SO₂(tC₄H₉) |
| 17.132 | 2 | Cl | SO₂Ph |
| 17.133 | 2 | Cl | NH₂ |
| 17.134 | 2 | Cl | NHCH₃ |
| 17.135 | 2 | Cl | NCH₃Ph |
| 17.136 | 2 | Cl | N(CH₃)₂ |
| 17.137 | 2 | Cl | NPh₂ |
| 17.138 | 2 | Cl | CN |
| 17.139 | 2 | Cl | NO₂ |
| 17.140 | 2 | CH₃ | F |
| 17.141 | 2 | CH₃ | Cl |
| 17.142 | 2 | CH₃ | Br |
| 17.143 | 2 | CH₃ | CH₃ |
| 17.144 | 2 | CH₃ | C₂H₅ |
| 17.145 | 2 | CH₃ | nC₃H₇ |
| 17.146 | 2 | CH₃ | iC₃H₇ |
| 17.147 | 2 | CH₃ | nC₄H₉ |
| 17.148 | 2 | CH₃ | tC₄H₉ |
| 17.149 | 2 | CH₃ | Ph |
| 17.150 | 2 | CH₃ | OH |
| 17.151 | 2 | CH₃ | OCH₃ |
| 17.152 | 2 | CH₃ | OC₂H₅ |
| 17.153 | 2 | CH₃ | O(nC₃H₇) |
| 17.154 | 2 | CH₃ | O(iC₃H₇) |
| 17.155 | 2 | CH₃ | O(nC₄H₉) |
| 17.156 | 2 | CH₃ | O(tC₄H₉) |
| 17.157 | 2 | CH₃ | OPh |
| 17.158 | 2 | CH₃ | SH |
| 17.159 | 2 | CH₃ | SCH₃ |
| 17.160 | 2 | CH₃ | SC₂H₅ |
| 17.161 | 2 | CH₃ | S(nC₃H₇) |
| 17.162 | 2 | CH₃ | S(iC₃H₇) |
| 17.163 | 2 | CH₃ | S(nC₄H₉) |
| 17.164 | 2 | CH₃ | S(tC₄H₉) |
| 17.165 | 2 | CH₃ | SPh |
| 17.166 | 2 | CH₃ | CCl₃ |
| 17.167 | 2 | CH₃ | CH₂F |
| 17.168 | 2 | CH₃ | CHF₂ |
| 17.169 | 2 | CH₃ | CF₃ |
| 17.170 | 2 | CH₃ | CF₂CHF₂ |
| 17.171 | 2 | CH₃ | SO₃H |
| 17.172 | 2 | CH₃ | SO₂CH₃ |
| 17.173 | 2 | CH₃ | SO₂C₂H₅ |
| 17.174 | 2 | CH₃ | SO₂(nC₃H₇) |
| 17.175 | 2 | CH₃ | SO₂(iC₃H₇) |
| 17.176 | 2 | CH₃ | SO₂(nC₄H₉) |
| 17.177 | 2 | CH₃ | SO₂(tC₄H₉) |
| 17.178 | 2 | CH₃ | SO₂Ph |
| 17.179 | 2 | CH₃ | NH₂ |
| 17.180 | 2 | CH₃ | NHCH₃ |
| 17.181 | 2 | CH₃ | NCH₃Ph |
| 17.182 | 2 | CH₃ | N(CH₃)₂ |
| 17.183 | 2 | CH₃ | NPh₂ |
| 17.184 | 2 | CH₃ | CN |
| 17.185 | 2 | CH₃ | NO₂ |

TABLE 7

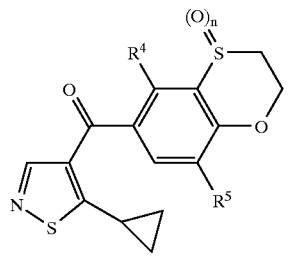
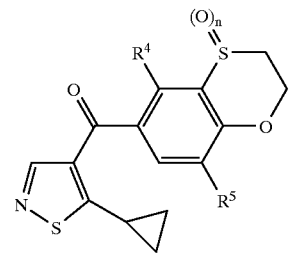

| No. | n | R⁴ | R⁵ |
|---|---|---|---|
| 18.1 | 0 | H | H |
| 18.2 | 0 | Cl | F |
| 18.3 | 0 | Cl | Cl |
| 18.4 | 0 | Cl | Br |
| 18.5 | 0 | Cl | $CH_3$ |
| 18.6 | 0 | Cl | $C_2H_5$ |
| 18.7 | 0 | Cl | $nC_3H_7$ |
| 18.8 | 0 | Cl | $iC_3H_7$ |
| 18.9 | 0 | Cl | $nC_4H_9$ |
| 18.10 | 0 | Cl | $tC_4H_9$ |
| 18.11 | 0 | Cl | Ph |
| 18.12 | 0 | Cl | OH |
| 18.13 | 0 | Cl | $OCH_3$ |
| 18.14 | 0 | Cl | $OC_2H_5$ |
| 18.15 | 0 | Cl | $O(nC_3H_7)$ |
| 18.16 | 0 | Cl | $O(iC_3H_7)$ |
| 18.17 | 0 | Cl | $O(nC_4H_9)$ |
| 18.18 | 0 | Cl | $O(tC_4H_9)$ |
| 18.19 | 0 | Cl | OPh |
| 18.20 | 0 | Cl | SH |
| 18.21 | 0 | Cl | $SCH_3$ |
| 18.22 | 0 | Cl | $SC_2H_5$ |
| 18.23 | 0 | Cl | $S(nC_3H_7)$ |
| 18.24 | 0 | Cl | $S(iC_3H_7)$ |
| 18.25 | 0 | Cl | $S(nC_4H_9)$ |
| 18.26 | 0 | Cl | $S(tC_4H_9)$ |
| 18.27 | 0 | Cl | SPh |
| 18.28 | 0 | Cl | $CCl_3$ |
| 18.29 | 0 | Cl | $CH_2F$ |
| 18.30 | 0 | Cl | $CHF_2$ |
| 18.31 | 0 | Cl | $CF_3$ |
| 18.32 | 0 | Cl | $CF_2CHF_2$ |
| 18.33 | 0 | Cl | $SO_3H$ |
| 18.34 | 0 | Cl | $SO_2CH_3$ |
| 18.35 | 0 | Cl | $SO_2C_2H_5$ |
| 18.36 | 0 | Cl | $SO_2(nC_3H_7)$ |
| 18.37 | 0 | Cl | $SO_2(iC_3H_7)$ |
| 18.38 | 0 | Cl | $SO_2(nC_4H_9)$ |
| 18.39 | 0 | Cl | $SO_2(tC_4H_9)$ |
| 18.40 | 0 | Cl | $SO_2Ph$ |
| 18.41 | 0 | Cl | $NH_2$ |
| 18.42 | 0 | Cl | $NHCH_3$ |
| 18.43 | 0 | Cl | $NCH_3Ph$ |
| 18.44 | 0 | Cl | $N(CH_3)_2$ |
| 18.45 | 0 | Cl | $NPh_2$ |
| 18.46 | 0 | Cl | CN |
| 18.47 | 0 | Cl | $NO_2$ |
| 18.48 | 0 | $CH_3$ | F |
| 18.49 | 0 | $CH_3$ | Cl |
| 18.50 | 0 | $CH_3$ | Br |
| 18.51 | 0 | $CH_3$ | $CH_3$ |
| 18.52 | 0 | $CH_3$ | $C_2H_5$ |
| 18.53 | 0 | $CH_3$ | $nC_3H_7$ |
| 18.54 | 0 | $CH_3$ | $iC_3H_7$ |
| 18.55 | 0 | $CH_3$ | $nC_4H_9$ |
| 18.56 | 0 | $CH_3$ | $tC_4H_9$ |
| 18.57 | 0 | $CH_3$ | Ph |
| 18.58 | 0 | $CH_3$ | OH |
| 18.59 | 0 | $CH_3$ | $OCH_3$ |
| 18.60 | 0 | $CH_3$ | $OC_2H_5$ |
| 18.61 | 0 | $CH_3$ | $O(nC_3H_7)$ |
| 18.62 | 0 | $CH_3$ | $O(iC_3H_7)$ |
| 18.63 | 0 | $CH_3$ | $O(nC_4H_9)$ |
| 18.64 | 0 | $CH_3$ | $O(tC_4H_9)$ |
| 18.65 | 0 | $CH_3$ | OPh |
| 18.66 | 0 | $CH_3$ | SH |
| 18.67 | 0 | $CH_3$ | $SCH_3$ |
| 18.68 | 0 | $CH_3$ | $SC_2H_5$ |
| 18.69 | 0 | $CH_3$ | $S(nC_3H_7)$ |
| 18.70 | 0 | $CH_3$ | $S(iC_3H_7)$ |
| 18.71 | 0 | $CH_3$ | $S(nC_4H_9)$ |
| 18.72 | 0 | $CH_3$ | $S(tC_4H_9)$ |
| 18.73 | 0 | $CH_3$ | SPh |
| 18.74 | 0 | $CH_3$ | $CCl_3$ |
| 18.75 | 0 | $CH_3$ | $CH_2F$ |
| 18.76 | 0 | $CH_3$ | $CHF_2$ |
| 18.77 | 0 | $CH_3$ | $CF_3$ |
| 18.78 | 0 | $CH_3$ | $CF_2CHF_2$ |
| 18.79 | 0 | $CH_3$ | $SO_3H$ |
| 18.80 | 0 | $CH_3$ | $SO_2CH_3$ |
| 18.81 | 0 | $CH_3$ | $SO_2C_2H_5$ |
| 18.82 | 0 | $CH_3$ | $SO_2(nC_3H_7)$ |
| 18.83 | 0 | $CH_3$ | $SO_2(iC_3H_7)$ |
| 18.84 | 0 | $CH_3$ | $SO_2(nC_4H_9)$ |
| 18.85 | 0 | $CH_3$ | $SO_2(tC_4H_9)$ |
| 18.86 | 0 | $CH_3$ | $SO_2Ph$ |
| 18.87 | 0 | $CH_3$ | $NH_2$ |
| 18.88 | 0 | $CH_3$ | $NHCH_3$ |
| 18.89 | 0 | $CH_3$ | $NCH_3Ph$ |
| 18.90 | 0 | $CH_3$ | $N(CH_3)_2$ |
| 18.91 | 0 | $CH_3$ | $NPh_2$ |
| 18.92 | 0 | $CH_3$ | CN |
| 18.93 | 0 | $CH_3$ | $NO_2$ |
| 18.94 | 2 | Cl | F |
| 18.95 | 2 | Cl | Cl |
| 18.96 | 2 | Cl | Br |
| 18.97 | 2 | Cl | $CH_3$ |
| 18.98 | 2 | Cl | $C_2H_5$ |
| 18.99 | 2 | Cl | $nC_3H_7$ |
| 18.100 | 2 | Cl | $iC_3H_7$ |
| 18.101 | 2 | Cl | $nC_4H_9$ |
| 18.102 | 2 | Cl | $tC_4H_9$ |
| 18.103 | 2 | Cl | Ph |
| 18.104 | 2 | Cl | OH |
| 18.105 | 2 | Cl | $OCH_3$ |
| 18.106 | 2 | Cl | $OC_2H_5$ |
| 18.107 | 2 | Cl | $O(nC_3H_7)$ |
| 18.108 | 2 | Cl | $O(iC_3H_7)$ |
| 18.109 | 2 | Cl | $O(nC_4H_9)$ |
| 18.110 | 2 | Cl | $O(tC_4H_9)$ |
| 18.111 | 2 | Cl | OPh |
| 18.112 | 2 | Cl | SH |
| 18.113 | 2 | Cl | $SCH_3$ |
| 18.114 | 2 | Cl | $SC_2H_5$ |
| 18.115 | 2 | Cl | $S(nC_3H_7)$ |
| 18.116 | 2 | Cl | $S(iC_3H_7)$ |
| 18.117 | 2 | Cl | $S(nC_4H_9)$ |
| 18.118 | 2 | Cl | $S(tC_4H_9)$ |
| 18.119 | 2 | Cl | SPh |
| 18.120 | 2 | Cl | $CCl_3$ |
| 18.121 | 2 | Cl | $CH_2F$ |
| 18.122 | 2 | Cl | $CHF_2$ |
| 18.123 | 2 | Cl | $CF_3$ |
| 18.124 | 2 | Cl | $CF_2CHF_2$ |
| 18.125 | 2 | Cl | $SO_3H$ |
| 18.126 | 2 | Cl | $SO_2CH_3$ |

TABLE 7-continued

| No. | n | R⁴ | R⁵ |
|---|---|---|---|
| 18.127 | 2 | Cl | SO$_2$C$_2$H$_5$ |
| 18.128 | 2 | Cl | SO$_2$(nC$_3$H$_7$) |
| 18.129 | 2 | Cl | SO$_2$(iC$_3$H$_7$) |
| 18.130 | 2 | Cl | SO$_2$(nC$_4$H$_9$) |
| 18.131 | 2 | Cl | SO$_2$(tC$_4$H$_9$) |
| 18.132 | 2 | Cl | SO$_2$Ph |
| 18.133 | 2 | Cl | NH$_2$ |
| 18.134 | 2 | Cl | NHCH$_3$ |
| 18.135 | 2 | Cl | NCH$_3$Ph |
| 18.136 | 2 | Cl | N(CH$_3$)$_2$ |
| 18.137 | 2 | Cl | NPh$_2$ |
| 18.138 | 2 | Cl | CN |
| 18.139 | 2 | Cl | NO$_2$ |
| 18.140 | 2 | CH$_3$ | F |
| 18.141 | 2 | CH$_3$ | Cl |
| 18.142 | 2 | CH$_3$ | Br |
| 18.143 | 2 | CH$_3$ | CH$_3$ |
| 18.144 | 2 | CH$_3$ | C$_2$H$_5$ |
| 18.145 | 2 | CH$_3$ | nC$_3$H$_7$ |
| 18.146 | 2 | CH$_3$ | iC$_3$H$_7$ |
| 18.147 | 2 | CH$_3$ | nC$_4$H$_9$ |
| 18.148 | 2 | CH$_3$ | tC$_4$H$_9$ |
| 18.149 | 2 | CH$_3$ | Ph |
| 18.150 | 2 | CH$_3$ | OH |
| 18.151 | 2 | CH$_3$ | OCH$_3$ |
| 18.152 | 2 | CH$_3$ | OC$_2$H$_5$ |
| 18.153 | 2 | CH$_3$ | O(nC$_3$H$_7$) |
| 18.154 | 2 | CH$_3$ | O(iC$_3$H$_7$) |
| 18.155 | 2 | CH$_3$ | O(nC$_4$H$_9$) |
| 18.156 | 2 | CH$_3$ | O(tC$_4$H$_9$) |
| 18.157 | 2 | CH$_3$ | OPh |
| 18.158 | 2 | CH$_3$ | SH |
| 18.159 | 2 | CH$_3$ | SCH$_3$ |
| 18.160 | 2 | CH$_3$ | SC$_2$H$_5$ |
| 18.161 | 2 | CH$_3$ | S(nC$_3$H$_7$) |
| 18.162 | 2 | CH$_3$ | S(iC$_3$H$_7$) |
| 18.163 | 2 | CH$_3$ | S(nC$_4$H$_9$) |
| 18.164 | 2 | CH$_3$ | S(tC$_4$H$_9$) |
| 18.165 | 2 | CH$_3$ | SPh |
| 18.166 | 2 | CH$_3$ | CCl$_3$ |
| 18.167 | 2 | CH$_3$ | CH$_2$F |
| 18.168 | 2 | CH$_3$ | CHF$_2$ |
| 18.169 | 2 | CH$_3$ | CF$_3$ |
| 18.170 | 2 | CH$_3$ | CF$_2$CHF$_2$ |
| 18.171 | 2 | CH$_3$ | SO$_3$H |
| 18.172 | 2 | CH$_3$ | SO$_2$CH$_3$ |
| 18.173 | 2 | CH$_3$ | SO$_2$C$_2$H$_5$ |
| 18.174 | 2 | CH$_3$ | SO$_2$(nC$_3$H$_7$) |
| 18.175 | 2 | CH$_3$ | SO$_2$(iC$_3$H$_7$) |
| 18.176 | 2 | CH$_3$ | SO$_2$(nC$_4$H$_9$) |
| 18.177 | 2 | CH$_3$ | SO$_2$(tC$_4$H$_9$) |
| 18.178 | 2 | CH$_3$ | SO$_2$Ph |
| 18.179 | 2 | CH$_3$ | NH$_2$ |
| 18.180 | 2 | CH$_3$ | NHCH$_3$ |
| 18.181 | 2 | CH$_3$ | NCH$_3$Ph |
| 18.182 | 2 | CH$_3$ | N(CH$_3$)$_2$ |
| 18.183 | 2 | CH$_3$ | NPh$_2$ |
| 18.184 | 2 | CH$_3$ | CN |
| 18.185 | 2 | CH$_3$ | NO$_2$ |

TABLE 8

| No. | R⁴ | R⁵ |
|---|---|---|
| 19.1 | H | H |
| 19.2 | Cl | F |
| 19.3 | Cl | Cl |
| 19.4 | Cl | Br |
| 19.5 | Cl | CH$_3$ |
| 19.6 | Cl | C$_2$H$_5$ |
| 19.7 | Cl | nC$_3$H$_7$ |
| 19.8 | Cl | iC$_3$H$_7$ |
| 19.9 | Cl | nC$_4$H$_9$ |
| 19.10 | Cl | tC$_4$H$_9$ |
| 19.11 | Cl | Ph |
| 19.12 | Cl | OH |
| 19.13 | Cl | OCH$_3$ |
| 19.14 | Cl | OC$_2$H$_5$ |
| 19.15 | Cl | O(nC$_3$H$_7$) |
| 19.16 | Cl | O(iC$_3$H$_7$) |
| 19.17 | Cl | O(nC$_4$H$_9$) |
| 19.18 | Cl | O(tC$_4$H$_9$) |
| 19.19 | Cl | OPh |
| 19.20 | Cl | SH |
| 19.21 | Cl | SCH$_3$ |
| 19.22 | Cl | SC$_2$H$_5$ |
| 19.23 | Cl | S(nC$_3$H$_7$) |
| 19.24 | Cl | S(iC$_3$H$_7$) |
| 19.25 | Cl | S(nC$_4$H$_9$) |
| 19.26 | Cl | S(tC$_4$H$_9$) |
| 19.27 | Cl | SPh |
| 19.28 | Cl | CCl$_3$ |
| 19.29 | Cl | CH$_2$F |
| 19.30 | Cl | CHF$_2$ |
| 19.31 | Cl | CF$_3$ |
| 19.32 | Cl | CF$_2$CHF$_2$ |
| 19.33 | Cl | SO$_3$H |
| 19.34 | Cl | SO$_2$CH$_3$ |
| 19.35 | Cl | SO$_2$C$_2$H$_5$ |
| 19.36 | Cl | SO$_2$(nC$_3$H$_7$) |
| 19.37 | Cl | SO$_2$(iC$_3$H$_7$) |
| 19.38 | Cl | SO$_2$(nC$_4$H$_9$) |
| 19.39 | Cl | SO$_2$(tC$_4$H$_9$) |
| 19.40 | Cl | SO$_2$Ph |
| 19.41 | Cl | NH$_2$ |
| 19.42 | Cl | NHCH$_3$ |
| 19.43 | Cl | NCH$_3$Ph |
| 19.44 | Cl | N(CH$_3$)$_2$ |
| 19.45 | Cl | NPh$_2$ |
| 19.46 | Cl | CN |
| 19.47 | Cl | NO$_2$ |
| 19.48 | CH$_3$ | F |
| 19.49 | CH$_3$ | Cl |
| 19.50 | CH$_3$ | Br |
| 19.51 | CH$_3$ | CH$_3$ |
| 19.52 | CH$_3$ | C$_2$H$_5$ |
| 19.53 | CH$_3$ | nC$_3$H$_7$ |
| 19.54 | CH$_3$ | iC$_3$H$_7$ |
| 19.55 | CH$_3$ | nC$_4$H$_9$ |
| 19.56 | CH$_3$ | tC$_4$H$_9$ |
| 19.57 | CH$_3$ | Ph |
| 19.58 | CH$_3$ | OH |
| 19.59 | CH$_3$ | OCH$_3$ |
| 19.60 | CH$_3$ | OC$_2$H$_5$ |
| 19.61 | CH$_3$ | O(nC$_3$H$_7$) |
| 19.62 | CH$_3$ | O(iC$_3$H$_7$) |
| 19.63 | CH$_3$ | O(nC$_4$H$_9$) |
| 19.64 | CH$_3$ | O(tC$_4$H$_9$) |
| 19.65 | CH$_3$ | OPh |

TABLE 8-continued

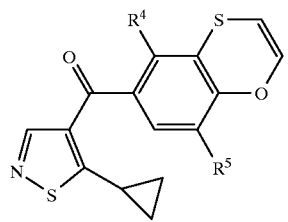

| No. | R⁴ | R⁵ |
| --- | --- | --- |
| 19.66 | CH₃ | SH |
| 19.67 | CH₃ | SCH₃ |
| 19.68 | CH₃ | SC₂H₅ |
| 19.69 | CH₃ | S(nC₃H₇) |
| 19.70 | CH₃ | S(iC₃H₇) |
| 19.71 | CH₃ | S(nC₄H₉) |
| 19.72 | CH₃ | S(tC₄H₉) |
| 19.73 | CH₃ | SPh |
| 19.74 | CH₃ | CCl₃ |
| 19.75 | CH₃ | CH₂F |
| 19.76 | CH₃ | CHF₂ |
| 19.77 | CH₃ | CF₃ |
| 19.78 | CH₃ | CF₂CHF₂ |
| 19.79 | CH₃ | SO₃H |
| 19.80 | CH₃ | SO₂CH₃ |
| 19.81 | CH₃ | SO₂C₂H₅ |
| 19.82 | CH₃ | SO₂(nC₃H₇) |
| 19.83 | CH₃ | SO₂(iC₃H₇) |
| 19.84 | CH₃ | SO₂(nC₄H₉) |
| 19.85 | CH₃ | SO₂(tC₄H₉) |
| 19.86 | CH₃ | SO₂Ph |
| 19.87 | CH₃ | NH₂ |
| 19.88 | CH₃ | NHCH₃ |
| 19.89 | CH₃ | NCH₃Ph |
| 19.90 | CH₃ | N(CH₃)₂ |
| 19.91 | CH₃ | NPh₂ |
| 19.92 | CH₃ | CN |
| 19.93 | CH₃ | NO₂ |

TABLE 9

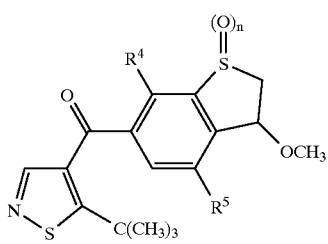

| No. | n | R⁴ | R⁵ |
| --- | --- | --- | --- |
| 20.1 | 0 | H | H |
| 20.2 | 0 | Cl | F |
| 20.3 | 0 | Cl | Cl |
| 20.4 | 0 | Cl | Br |
| 20.5 | 0 | Cl | CH₃ |
| 20.6 | 0 | Cl | C₂H₅ |
| 20.7 | 0 | Cl | nC₃H₇ |
| 20.8 | 0 | Cl | iC₃H₇ |
| 20.9 | 0 | Cl | nC₄H₉ |
| 20.10 | 0 | Cl | tC₄H₉ |
| 20.11 | 0 | Cl | Ph |
| 20.12 | 0 | Cl | OH |
| 20.13 | 0 | Cl | OCH₃ |
| 20.14 | 0 | Cl | OC₂H₅ |
| 20.15 | 0 | Cl | O(nC₃H₇) |
| 20.16 | 0 | Cl | O(iC₃H₇) |
| 20.17 | 0 | Cl | O(nC₄H₉) |

TABLE 9-continued

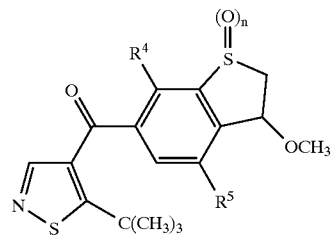

| No. | n | R⁴ | R⁵ |
| --- | --- | --- | --- |
| 20.18 | 0 | Cl | O(tC₄H₉) |
| 20.19 | 0 | Cl | OPh |
| 20.20 | 0 | Cl | SH |
| 20.21 | 0 | Cl | SCH₃ |
| 20.22 | 0 | Cl | SC₂H₅ |
| 20.23 | 0 | Cl | S(nC₃H₇) |
| 20.24 | 0 | Cl | S(iC₃H₇) |
| 20.25 | 0 | Cl | S(nC₄H₉) |
| 20.26 | 0 | Cl | S(tC₄H₉) |
| 20.27 | 0 | Cl | SPh |
| 20.28 | 0 | Cl | CCl₃ |
| 20.29 | 0 | Cl | CH₂F |
| 20.30 | 0 | Cl | CHF₂ |
| 20.31 | 0 | Cl | CF₃ |
| 20.32 | 0 | Cl | CF₂CHF₂ |
| 20.33 | 0 | Cl | SO₃H |
| 20.34 | 0 | Cl | SO₂CH₃ |
| 20.35 | 0 | Cl | SO₂C₂H₅ |
| 20.36 | 0 | Cl | SO₂(nC₃H₇) |
| 20.37 | 0 | Cl | SO₂(iC₃H₇) |
| 20.38 | 0 | Cl | SO₂(nC₄H₉) |
| 20.39 | 0 | Cl | SO₂(tC₄H₉) |
| 20.40 | 0 | Cl | SO₂Ph |
| 20.41 | 0 | Cl | NH₂ |
| 20.42 | 0 | Cl | NHCH₃ |
| 20.43 | 0 | Cl | NCH₃Ph |
| 20.44 | 0 | Cl | N(CH₃)₂ |
| 20.45 | 0 | Cl | NPh₂ |
| 20.46 | 0 | Cl | CN |
| 20.47 | 0 | Cl | NO₂ |
| 20.48 | 0 | CH₃ | F |
| 20.49 | 0 | CH₃ | Cl |
| 20.50 | 0 | CH₃ | Br |
| 20.51 | 0 | CH₃ | CH₃ |
| 20.52 | 0 | CH₃ | C₂H₅ |
| 20.53 | 0 | CH₃ | nC₃H₇ |
| 20.54 | 0 | CH₃ | iC₃H₇ |
| 20.55 | 0 | CH₃ | nC₄H₉ |
| 20.56 | 0 | CH₃ | tC₄H₉ |
| 20.57 | 0 | CH₃ | Ph |
| 20.58 | 0 | CH₃ | OH |
| 20.59 | 0 | CH₃ | OCH₃ |
| 20.60 | 0 | CH₃ | OC₂H₅ |
| 20.61 | 0 | CH₃ | O(nC₃H₇) |
| 20.62 | 0 | CH₃ | O(iC₃H₇) |
| 20.63 | 0 | CH₃ | O(nC₄H₉) |
| 20.64 | 0 | CH₃ | O(tC₄H₉) |
| 20.65 | 0 | CH₃ | OPh |
| 20.66 | 0 | CH₃ | SH |
| 20.67 | 0 | CH₃ | SCH₃ |
| 20.68 | 0 | CH₃ | SC₂H₅ |
| 20.69 | 0 | CH₃ | S(nC₃H₇) |
| 20.70 | 0 | CH₃ | S(iC₃H₇) |
| 20.71 | 0 | CH₃ | S(nC₄H₉) |
| 20.72 | 0 | CH₃ | S(tC₄H₉) |
| 20.73 | 0 | CH₃ | SPh |
| 20.74 | 0 | CH₃ | CCl₃ |
| 20.75 | 0 | CH₃ | CH₂F |
| 20.76 | 0 | CH₃ | CHF₂ |
| 20.77 | 0 | CH₃ | CF₃ |
| 20.78 | 0 | CH₃ | CF₂CHF₂ |
| 20.79 | 0 | CH₃ | SO₃H |
| 20.80 | 0 | CH₃ | SO₂CH₃ |
| 20.81 | 0 | CH₃ | SO₂C₂H₅ |

TABLE 9-continued

| No. | n | R⁴ | R⁵ |
|---|---|---|---|
| 20.82 | 0 | CH₃ | SO₂(nC₃H₇) |
| 20.83 | 0 | CH₃ | SO₂(iC₃H₇) |
| 20.84 | 0 | CH₃ | SO₂(nC₄H₉) |
| 20.85 | 0 | CH₃ | SO₂(tC₄H₉) |
| 20.86 | 0 | CH₃ | SO₂Ph |
| 20.87 | 0 | CH₃ | NH₂ |
| 20.88 | 0 | CH₃ | NHCH₃ |
| 20.89 | 0 | CH₃ | NCH₃Ph |
| 20.90 | 0 | CH₃ | N(CH₃)₂ |
| 20.91 | 0 | CH₃ | NPh₂ |
| 20.92 | 0 | CH₃ | CN |
| 20.93 | 0 | CH₃ | NO₂ |
| 20.94 | 2 | Cl | F |
| 20.95 | 2 | Cl | Cl |
| 20.96 | 2 | Cl | Br |
| 20.97 | 2 | Cl | CH₃ |
| 20.98 | 2 | Cl | C₂H₅ |
| 20.99 | 2 | Cl | nC₃H₇ |
| 20.100 | 2 | Cl | iC₃H₇ |
| 20.101 | 2 | Cl | nC₄H₉ |
| 20.102 | 2 | Cl | tC₄H₉ |
| 20.103 | 2 | Cl | Ph |
| 20.104 | 2 | Cl | OH |
| 20.105 | 2 | Cl | OCH₃ |
| 20.106 | 2 | Cl | OC₂H₅ |
| 20.107 | 2 | Cl | O(nC₃H₇) |
| 20.108 | 2 | Cl | O(iC₃H₇) |
| 20.109 | 2 | Cl | O(nC₄H₉) |
| 20.110 | 2 | Cl | O(tC₄H₉) |
| 20.111 | 2 | Cl | OPh |
| 20.112 | 2 | Cl | SH |
| 20.113 | 2 | Cl | SCH₃ |
| 20.114 | 2 | Cl | SC₂H₅ |
| 20.115 | 2 | Cl | S(nC₃H₇) |
| 20.116 | 2 | Cl | S(iC₃H₇) |
| 20.117 | 2 | Cl | S(nC₄H₉) |
| 20.118 | 2 | Cl | S(tC₄H₉) |
| 20.119 | 2 | Cl | SPh |
| 20.120 | 2 | Cl | CCl₃ |
| 20.121 | 2 | Cl | CH₂F |
| 20.122 | 2 | Cl | CHF₂ |
| 20.123 | 2 | Cl | CF₃ |
| 20.124 | 2 | Cl | CF₂CHF₂ |
| 20.125 | 2 | Cl | SO₃H |
| 20.126 | 2 | Cl | SO₂CH₃ |
| 20.127 | 2 | Cl | SO₂C₂H₅ |
| 20.128 | 2 | Cl | SO₂(nC₃H₇) |
| 20.129 | 2 | Cl | SO₂(iC₃H₇) |
| 20.130 | 2 | Cl | SO₂(nC₄H₉) |
| 20.131 | 2 | Cl | SO₂(tC₄H₉) |
| 20.132 | 2 | Cl | SO₂Ph |
| 20.133 | 2 | Cl | NH₂ |
| 20.134 | 2 | Cl | NHCH₃ |
| 20.135 | 2 | Cl | NCH₃Ph |
| 20.136 | 2 | Cl | N(CH₃)₂ |
| 20.137 | 2 | Cl | NPh₂ |
| 20.138 | 2 | Cl | CN |
| 20.139 | 2 | Cl | NO₂ |
| 20.140 | 2 | CH₃ | F |
| 20.141 | 2 | CH₃ | Cl |
| 20.142 | 2 | CH₃ | Br |
| 20.143 | 2 | CH₃ | CH₃ |
| 20.144 | 2 | CH₃ | C₂H₅ |
| 20.145 | 2 | CH₃ | nC₃H₇ |
| 20.146 | 2 | CH₃ | iC₃H₇ |
| 20.147 | 2 | CH₃ | nC₄H₉ |
| 20.148 | 2 | CH₃ | tC₄H₉ |
| 20.149 | 2 | CH₃ | Ph |
| 20.150 | 2 | CH₃ | OH |
| 20.151 | 2 | CH₃ | OCH₃ |
| 20.152 | 2 | CH₃ | OC₂H₅ |
| 20.153 | 2 | CH₃ | O(nC₃H₇) |
| 20.154 | 2 | CH₃ | O(iC₃H₇) |
| 20.155 | 2 | CH₃ | O(nC₄H₉) |
| 20.156 | 2 | CH₃ | O(tC₄H₉) |
| 20.157 | 2 | CH₃ | OPh |
| 20.158 | 2 | CH₃ | SH |
| 20.159 | 2 | CH₃ | SCH₃ |
| 20.160 | 2 | CH₃ | SC₂H₅ |
| 20.161 | 2 | CH₃ | S(nC₃H₇) |
| 20.162 | 2 | CH₃ | S(iC₃H₇) |
| 20.163 | 2 | CH₃ | S(nC₄H₉) |
| 20.164 | 2 | CH₃ | S(tC₄H₉) |
| 20.165 | 2 | CH₃ | SPh |
| 20.166 | 2 | CH₃ | CCl₃ |
| 20.167 | 2 | CH₃ | CH₂F |
| 20.168 | 2 | CH₃ | CHF₂ |
| 20.169 | 2 | CH₃ | CF₃ |
| 20.170 | 2 | CH₃ | CF₂CHF₂ |
| 20.171 | 2 | CH₃ | SO₃H |
| 20.172 | 2 | CH₃ | SO₂CH₃ |
| 20.173 | 2 | CH₃ | SO₂C₂H₅ |
| 20.174 | 2 | CH₃ | SO₂(nC₃H₇) |
| 20.175 | 2 | CH₃ | SO₂(iC₃H₇) |
| 20.176 | 2 | CH₃ | SO₂(nC₄H₉) |
| 20.177 | 2 | CH₃ | SO₂(tC₄H₉) |
| 20.178 | 2 | CH₃ | SO₂Ph |
| 20.179 | 2 | CH₃ | NH₂ |
| 20.180 | 2 | CH₃ | NHCH₃ |
| 20.181 | 2 | CH₃ | NCH₃Ph |
| 20.182 | 2 | CH₃ | N(CH₃)₂ |
| 20.183 | 2 | CH₃ | NPh₂ |
| 20.184 | 2 | CH₃ | CN |
| 20.185 | 2 | CH₃ | NO₂ |

TABLE 10

| No. | R⁴ | R⁵ |
|---|---|---|
| 21.1 | H | H |
| 21.2 | Cl | F |
| 21.3 | Cl | Cl |

TABLE 10-continued

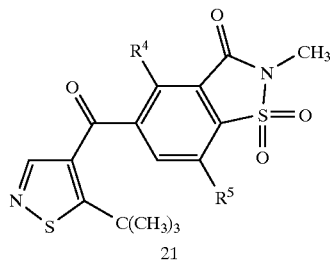

21

| No. | R⁴ | R⁵ |
|---|---|---|
| 21.4 | Cl | Br |
| 21.5 | Cl | $CH_3$ |
| 21.6 | Cl | $C_2H_5$ |
| 21.7 | Cl | $nC_3H_7$ |
| 21.8 | Cl | $iC_3H_7$ |
| 21.9 | Cl | $nC_4H_9$ |
| 21.10 | Cl | $tC_4H_9$ |
| 21.11 | Cl | Ph |
| 21.12 | Cl | OH |
| 21.13 | Cl | $OCH_3$ |
| 21.14 | Cl | $OC_2H_5$ |
| 21.15 | Cl | $O(nC_3H_7)$ |
| 21.16 | Cl | $O(iC_3H_7)$ |
| 21.17 | Cl | $O(nC_4H_9)$ |
| 21.18 | Cl | $O(tC_4H_9)$ |
| 21.19 | Cl | OPh |
| 21.20 | Cl | SH |
| 21.21 | Cl | $SCH_3$ |
| 21.22 | Cl | $SC_2H_5$ |
| 21.23 | Cl | $S(nC_3H_7)$ |
| 21.24 | Cl | $S(iC_3H_7)$ |
| 21.25 | Cl | $S(nC_4H_9)$ |
| 21.26 | Cl | $S(tC_4H_9)$ |
| 21.27 | Cl | SPh |
| 21.28 | Cl | $CCl_3$ |
| 21.29 | Cl | $CH_2F$ |
| 21.30 | Cl | $CHF_2$ |
| 21.31 | Cl | $CF_3$ |
| 21.32 | Cl | $CF_2CHF_2$ |
| 21.33 | Cl | $SO_3H$ |
| 21.34 | Cl | $SO_2CH_3$ |
| 21.35 | Cl | $SO_2C_2H_5$ |
| 21.36 | Cl | $SO_2(nC_3H_7)$ |
| 21.37 | Cl | $SO_2(iC_3H_7)$ |
| 21.38 | Cl | $SO_2(nC_4H_9)$ |
| 21.39 | Cl | $SO_2(tC_4H_9)$ |
| 21.40 | Cl | $SO_2Ph$ |
| 21.41 | Cl | $NH_2$ |
| 21.42 | Cl | $NHCH_3$ |
| 21.43 | Cl | $NCH_3Ph$ |
| 21.44 | Cl | $N(CH_3)_2$ |
| 21.45 | Cl | $NPh_2$ |
| 21.46 | Cl | CN |
| 21.47 | Cl | $NO_2$ |
| 21.48 | $CH_3$ | F |
| 21.49 | $CH_3$ | Cl |
| 21.50 | $CH_3$ | Br |
| 21.51 | $CH_3$ | $CH_3$ |
| 21.52 | $CH_3$ | $C_2H_5$ |
| 21.53 | $CH_3$ | $nC_3H_7$ |
| 21.54 | $CH_3$ | $iC_3H_7$ |
| 21.55 | $CH_3$ | $nC_4H_9$ |
| 21.56 | $CH_3$ | $tC_4H_9$ |
| 21.57 | $CH_3$ | Ph |
| 21.58 | $CH_3$ | OH |
| 21.59 | $CH_3$ | $OCH_3$ |
| 21.60 | $CH_3$ | $OC_2H_5$ |
| 21.61 | $CH_3$ | $O(nC_3H_7)$ |
| 21.62 | $CH_3$ | $O(iC_3H_7)$ |
| 21.63 | $CH_3$ | $O(nC_4H_9)$ |
| 21.64 | $CH_3$ | $O(tC_4H_9)$ |
| 21.65 | $CH_3$ | OPh |
| 21.66 | $CH_3$ | SH |

TABLE 10-continued

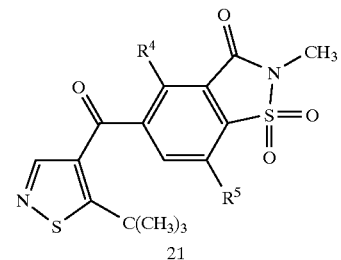

21

| No. | R⁴ | R⁵ |
|---|---|---|
| 21.67 | $CH_3$ | $SCH_3$ |
| 21.68 | $CH_3$ | $SC_2H_5$ |
| 21.69 | $CH_3$ | $S(nC_3H_7)$ |
| 21.70 | $CH_3$ | $S(iC_3H_7)$ |
| 21.71 | $CH_3$ | $S(nC_4H_9)$ |
| 21.72 | $CH_3$ | $S(tC_4H_9)$ |
| 21.73 | $CH_3$ | SPh |
| 21.74 | $CH_3$ | $CCl_3$ |
| 21.75 | $CH_3$ | $CH_2F$ |
| 21.76 | $CH_3$ | $CHF_2$ |
| 21.77 | $CH_3$ | $CF_3$ |
| 21.78 | $CH_3$ | $CF_2CHF_2$ |
| 21.79 | $CH_3$ | $SO_3H$ |
| 21.80 | $CH_3$ | $SO_2CH_3$ |
| 21.81 | $CH_3$ | $SO_2C_2H_5$ |
| 21.82 | $CH_3$ | $SO_2(nC_3H_7)$ |
| 21.83 | $CH_3$ | $SO_2(iC_3H_7)$ |
| 21.84 | $CH_3$ | $SO_2(nC_4H_9)$ |
| 21.85 | $CH_3$ | $SO_2(tC_4H_9)$ |
| 21.86 | $CH_3$ | $SO_2Ph$ |
| 21.87 | $CH_3$ | $NH_2$ |
| 21.88 | $CH_3$ | $NHCH_3$ |
| 21.89 | $CH_3$ | $NCH_3Ph$ |
| 21.90 | $CH_3$ | $N(CH_3)_2$ |
| 21.91 | $CH_3$ | $NPh_2$ |
| 21.92 | $CH_3$ | CN |
| 21.93 | $CH_3$ | $NO_2$ |

TABLE 11

22

| No. | n | R⁴ | R⁵ |
|---|---|---|---|
| 22.1 | 0 | H | H |
| 22.2 | 0 | Cl | F |
| 22.3 | 0 | Cl | Cl |
| 22.4 | 0 | Cl | Br |
| 22.5 | 0 | Cl | $CH_3$ |
| 22.6 | 0 | Cl | $C_2H_5$ |
| 22.7 | 0 | Cl | $nC_3H_7$ |
| 22.8 | 0 | Cl | $iC_3H_7$ |
| 22.9 | 0 | Cl | $nC_4H_9$ |
| 22.10 | 0 | Cl | $tC_4H_9$ |
| 22.11 | 0 | Cl | Ph |
| 22.12 | 0 | Cl | OH |
| 22.13 | 0 | Cl | $OCH_3$ |
| 22.14 | 0 | Cl | $OC_2H_5$ |
| 22.15 | 0 | Cl | $O(nC_3H_7)$ |

TABLE 11-continued

![Structure 22: isothiazole with C(CH₃)₃ substituent connected via carbonyl to thiochromanone with R⁴, R⁵, and (O)ₙ on sulfur]

22

| No. | n | R⁴ | R⁵ |
|---|---|---|---|
| 22.16 | 0 | Cl | O(iC₃H₇) |
| 22.17 | 0 | Cl | O(nC₄H₉) |
| 22.18 | 0 | Cl | O(tC₄H₉) |
| 22.19 | 0 | Cl | OPh |
| 22.20 | 0 | Cl | SH |
| 22.21 | 0 | Cl | SCH₃ |
| 22.22 | 0 | Cl | SC₂H₅ |
| 22.23 | 0 | Cl | S(nC₃H₇) |
| 22.24 | 0 | Cl | S(iC₃H₇) |
| 22.25 | 0 | Cl | S(nC₄H₉) |
| 22.26 | 0 | Cl | S(tC₄H₉) |
| 22.27 | 0 | Cl | SPh |
| 22.28 | 0 | Cl | CCl₃ |
| 22.29 | 0 | Cl | CH₂F |
| 22.30 | 0 | Cl | CHF₂ |
| 22.31 | 0 | Cl | CF₃ |
| 22.32 | 0 | Cl | CF₂CHF₂ |
| 22.33 | 0 | Cl | SO₃H |
| 22.34 | 0 | Cl | SO₂CH₃ |
| 22.35 | 0 | Cl | SO₂C₂H₅ |
| 22.36 | 0 | Cl | SO₂(nC₃H₇) |
| 22.37 | 0 | Cl | SO₂(iC₃H₇) |
| 22.38 | 0 | Cl | SO₂(nC₄H₉) |
| 22.39 | 0 | Cl | SO₂(tC₄H₉) |
| 22.40 | 0 | Cl | SO₂Ph |
| 22.41 | 0 | Cl | NH₂ |
| 22.42 | 0 | Cl | NHCH₃ |
| 22.43 | 0 | Cl | NCH₃Ph |
| 22.44 | 0 | Cl | N(CH₃)₂ |
| 22.45 | 0 | Cl | NPh₂ |
| 22.46 | 0 | Cl | CN |
| 22.47 | 0 | Cl | NO₂ |
| 22.48 | 0 | CH₃ | F |
| 22.49 | 0 | CH₃ | Cl |
| 22.50 | 0 | CH₃ | Br |
| 22.51 | 0 | CH₃ | CH₃ |
| 22.52 | 0 | CH₃ | C₂H₅ |
| 22.53 | 0 | CH₃ | nC₃H₇ |
| 22.54 | 0 | CH₃ | iC₃H₇ |
| 22.55 | 0 | CH₃ | nC₄H₉ |
| 22.56 | 0 | CH₃ | tC₄H₉ |
| 22.57 | 0 | CH₃ | Ph |
| 22.58 | 0 | CH₃ | OH |
| 22.59 | 0 | CH₃ | OCH₃ |
| 22.60 | 0 | CH₃ | OC₂H₅ |
| 22.61 | 0 | CH₃ | O(nC₃H₇) |
| 22.62 | 0 | CH₃ | O(iC₃H₇) |
| 22.63 | 0 | CH₃ | O(nC₄H₉) |
| 22.64 | 0 | CH₃ | O(tC₄H₉) |
| 22.65 | 0 | CH₃ | OPh |
| 22.66 | 0 | CH₃ | SH |
| 22.67 | 0 | CH₃ | SCH₃ |
| 22.68 | 0 | CH₃ | SC₂H₅ |
| 22.69 | 0 | CH₃ | S(nC₃H₇) |
| 22.70 | 0 | CH₃ | S(iC₃H₇) |
| 22.71 | 0 | CH₃ | S(nC₄H₉) |
| 22.72 | 0 | CH₃ | S(tC₄H₉) |
| 22.73 | 0 | CH₃ | SPh |
| 22.74 | 0 | CH₃ | CCl₃ |
| 22.75 | 0 | CH₃ | CH₂F |
| 22.76 | 0 | CH₃ | CHF₂ |
| 22.77 | 0 | CH₃ | CF₃ |
| 22.78 | 0 | CH₃ | CF₂CHF₂ |
| 22.79 | 0 | CH₃ | SO₃H |
| 22.80 | 0 | CH₃ | SO₂CH₃ |
| 22.81 | 0 | CH₃ | SO₂C₂H₅ |
| 22.82 | 0 | CH₃ | SO₂(nC₃H₇) |
| 22.83 | 0 | CH₃ | SO₂(iC₃H₇) |
| 22.84 | 0 | CH₃ | SO₂(nC₄H₉) |
| 22.85 | 0 | CH₃ | SO₂(tC₄H₉) |
| 22.86 | 0 | CH₃ | SO₂Ph |
| 22.87 | 0 | CH₃ | NH₂ |
| 22.88 | 0 | CH₃ | NHCH₃ |
| 22.89 | 0 | CH₃ | NCH₃Ph |
| 22.90 | 0 | CH₃ | N(CH₃)₂ |
| 22.91 | 0 | CH₃ | NPh₂ |
| 22.92 | 0 | CH₃ | CN |
| 22.93 | 0 | CH₃ | NO₂ |
| 22.94 | 2 | Cl | F |
| 22.95 | 2 | Cl | Cl |
| 22.96 | 2 | Cl | Br |
| 22.97 | 2 | Cl | CH₃ |
| 22.98 | 2 | Cl | C₂H₅ |
| 22.99 | 2 | Cl | nC₃H₇ |
| 22.100 | 2 | Cl | iC₃H₇ |
| 22.101 | 2 | Cl | nC₄H₉ |
| 22.102 | 2 | Cl | tC₄H₉ |
| 22.103 | 2 | Cl | Ph |
| 22.104 | 2 | Cl | OH |
| 22.105 | 2 | Cl | OCH₃ |
| 22.106 | 2 | Cl | OC₂H₅ |
| 22.107 | 2 | Cl | O(nC₃H₇) |
| 22.108 | 2 | Cl | O(iC₃H₇) |
| 22.109 | 2 | Cl | O(nC₄H₉) |
| 22.110 | 2 | Cl | O(tC₄H₉) |
| 22.111 | 2 | Cl | OPh |
| 22.112 | 2 | Cl | SH |
| 22.113 | 2 | Cl | SCH₃ |
| 22.114 | 2 | Cl | SC₂H₅ |
| 22.115 | 2 | Cl | S(nC₃H₇) |
| 22.116 | 2 | Cl | S(iC₃H₇) |
| 22.117 | 2 | Cl | S(nC₄H₉) |
| 22.118 | 2 | Cl | S(tC₄H₉) |
| 22.119 | 2 | Cl | SPh |
| 22.120 | 2 | Cl | CCl₃ |
| 22.121 | 2 | Cl | CH₂F |
| 22.122 | 2 | Cl | CHF₂ |
| 22.123 | 2 | Cl | CF₃ |
| 22.124 | 2 | Cl | CF₂CHF₂ |
| 22.125 | 2 | Cl | SO₃H |
| 22.126 | 2 | Cl | SO₂CH₃ |
| 22.127 | 2 | Cl | SO₂C₂H₅ |
| 22.128 | 2 | Cl | SO₂(nC₃H₇) |
| 22.129 | 2 | Cl | SO₂(iC₃H₇) |
| 22.130 | 2 | Cl | SO₂(nC₄H₉) |
| 22.131 | 2 | Cl | SO₂(tC₄H₉) |
| 22.132 | 2 | Cl | SO₂Ph |
| 22.133 | 2 | Cl | NH₂ |
| 22.134 | 2 | Cl | NHCH₃ |
| 22.135 | 2 | Cl | NCH₃Ph |
| 22.136 | 2 | Cl | N(CH₃)₂ |
| 22.137 | 2 | Cl | NPh₂ |
| 22.138 | 2 | Cl | CN |
| 22.139 | 2 | Cl | NO₂ |
| 22.140 | 2 | CH₃ | F |
| 22.141 | 2 | CH₃ | Cl |

TABLE 11-continued

Structure 22: thiochromanone with S(O)n, R4, R5 substituents, linked to isothiazole-C(CH3)3 via carbonyl.

| No. | n | R⁴ | R⁵ |
|---|---|---|---|
| 22.142 | 2 | CH₃ | Br |
| 22.143 | 2 | CH₃ | CH₃ |
| 22.144 | 2 | CH₃ | C₂H₅ |
| 22.145 | 2 | CH₃ | nC₃H₇ |
| 22.146 | 2 | CH₃ | iC₃H₇ |
| 22.147 | 2 | CH₃ | nC₄H₉ |
| 22.148 | 2 | CH₃ | tC₄H₉ |
| 22.149 | 2 | CH₃ | Ph |
| 22.150 | 2 | CH₃ | OH |
| 22.151 | 2 | CH₃ | OCH₃ |
| 22.152 | 2 | CH₃ | OC₂H₅ |
| 22.153 | 2 | CH₃ | O(nC₃H₇) |
| 22.154 | 2 | CH₃ | O(iC₃H₇) |
| 22.155 | 2 | CH₃ | O(nC₄H₉) |
| 22.156 | 2 | CH₃ | O(tC₄H₉) |
| 22.157 | 2 | CH₃ | OPh |
| 22.158 | 2 | CH₃ | SH |
| 22.159 | 2 | CH₃ | SCH₃ |
| 22.160 | 2 | CH₃ | SC₂H₅ |
| 22.161 | 2 | CH₃ | S(nC₃H₇) |
| 22.162 | 2 | CH₃ | S(iC₃H₇) |
| 22.163 | 2 | CH₃ | S(nC₄H₉) |
| 22.164 | 2 | CH₃ | S(tC₄H₉) |
| 22.165 | 2 | CH₃ | SPh |
| 22.166 | 2 | CH₃ | CCl₃ |
| 22.167 | 2 | CH₃ | CH₂F |
| 22.168 | 2 | CH₃ | CHF₂ |
| 22.169 | 2 | CH₃ | CF₃ |
| 22.170 | 2 | CH₃ | CF₂CHF₂ |
| 22.171 | 2 | CH₃ | SO₃H |
| 22.172 | 2 | CH₃ | SO₂CH₃ |
| 22.173 | 2 | CH₃ | SO₂C₂H₅ |
| 22.174 | 2 | CH₃ | SO₂(nC₃H₇) |
| 22.175 | 2 | CH₃ | SO₂(iC₃H₇) |
| 22.176 | 2 | CH₃ | SO₂(nC₄H₉) |
| 22.177 | 2 | CH₃ | SO₂(tC₄H₉) |
| 22.178 | 2 | CH₃ | SO₂Ph |
| 22.179 | 2 | CH₃ | NH₂ |
| 22.180 | 2 | CH₃ | NHCH₃ |
| 22.181 | 2 | CH₃ | NCH₃Ph |
| 22.182 | 2 | CH₃ | N(CH₃)₂ |
| 22.183 | 2 | CH₃ | NPh₂ |
| 22.184 | 2 | CH₃ | CN |
| 22.185 | 2 | CH₃ | NO₂ |

TABLE 12

Structure 23: thiochromone with R4, R5 substituents, linked to isothiazole-C(CH3)3 via carbonyl.

| No. | R⁴ | R⁵ |
|---|---|---|
| 23.1 | H | H |
| 23.2 | Cl | F |
| 23.3 | Cl | Cl |
| 23.4 | Cl | Br |
| 23.5 | Cl | CH₃ |
| 23.6 | Cl | C₂H₅ |
| 23.7 | Cl | nC₃H₇ |
| 23.8 | Cl | iC₃H₇ |
| 23.9 | Cl | nC₄H₉ |
| 23.10 | Cl | tC₄H₉ |
| 23.11 | Cl | Ph |
| 23.12 | Cl | OH |
| 23.13 | Cl | OCH₃ |
| 23.14 | Cl | OC₂H₅ |
| 23.15 | Cl | O(nC₃H₇) |
| 23.16 | Cl | O(iC₃H₇) |
| 23.17 | Cl | O(nC₄H₉) |
| 23.18 | Cl | O(tC₄H₉) |
| 23.19 | Cl | OPh |
| 23.20 | Cl | SH |
| 23.21 | Cl | SCH₃ |
| 23.22 | Cl | SC₂H₅ |
| 23.23 | Cl | S(nC₃H₇) |
| 23.24 | Cl | S(iC₃H₇) |
| 23.25 | Cl | S(nC₄H₉) |
| 23.26 | Cl | S(tC₄H₉) |
| 23.27 | Cl | SPh |
| 23.28 | Cl | CCl₃ |
| 23.29 | Cl | CH₂F |
| 23.30 | Cl | CHF₂ |
| 23.31 | Cl | CF₃ |
| 23.32 | Cl | CF₂CHF₂ |
| 23.33 | Cl | SO₃H |
| 23.34 | Cl | SO₂CH₃ |
| 23.35 | Cl | SO₂C₂H₅ |
| 23.36 | Cl | SO₂(nC₃H₇) |
| 23.37 | Cl | SO₂(iC₃H₇) |
| 23.38 | Cl | SO₂(nC₄H₉) |
| 23.39 | Cl | SO₂(tC₄H₉) |
| 23.40 | Cl | SO₂Ph |
| 23.41 | Cl | NH₂ |
| 23.42 | Cl | NHCH₃ |
| 23.43 | Cl | NCH₃Ph |
| 23.44 | Cl | N(CH₃)₂ |
| 23.45 | Cl | NPh₂ |
| 23.46 | Cl | CN |
| 23.47 | Cl | NO₂ |
| 23.48 | CH₃ | F |
| 23.49 | CH₃ | Cl |
| 23.50 | CH₃ | Br |
| 23.51 | CH₃ | CH₃ |
| 23.52 | CH₃ | C₂H₅ |
| 23.53 | CH₃ | nC₃H₇ |
| 23.54 | CH₃ | iC₃H₇ |
| 23.55 | CH₃ | nC₄H₉ |
| 23.56 | CH₃ | tC₄H₉ |
| 23.57 | CH₃ | Ph |
| 23.58 | CH₃ | OH |
| 23.59 | CH₃ | OCH₃ |
| 23.60 | CH₃ | OC₂H₅ |
| 23.61 | CH₃ | O(nC₃H₇) |
| 23.62 | CH₃ | O(iC₃H₇) |
| 23.63 | CH₃ | O(nC₄H₉) |
| 23.64 | CH₃ | O(tC₄H₉) |

TABLE 12-continued

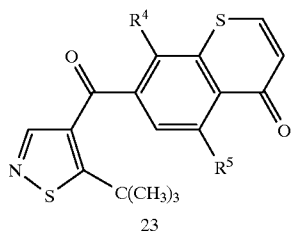

| No. | R⁴ | R⁵ |
|---|---|---|
| 23.65 | CH₃ | OPh |
| 23.66 | CH₃ | SH |
| 23.67 | CH₃ | SCH₃ |
| 23.68 | CH₃ | SC₂H₅ |
| 23.69 | CH₃ | S(nC₃H₇) |
| 23.70 | CH₃ | S(iC₃H₇) |
| 23.71 | CH₃ | S(nC₄H₉) |
| 23.72 | CH₃ | S(tC₄H₉) |
| 23.73 | CH₃ | SPh |
| 23.74 | CH₃ | CCl₃ |
| 23.75 | CH₃ | CH₂F |
| 23.76 | CH₃ | CHF₂ |
| 23.77 | CH₃ | CF₃ |
| 23.78 | CH₃ | CF₂CHF₂ |
| 23.79 | CH₃ | SO₃H |
| 23.80 | CH₃ | SO₂CH₃ |
| 23.81 | CH₃ | SO₂C₂H₅ |
| 23.82 | CH₃ | SO₂(nC₃H₇) |
| 23.83 | CH₃ | SO₂(iC₃H₇) |
| 23.84 | CH₃ | SO₂(nC₄H₉) |
| 23.85 | CH₃ | SO₂(tC₄H₉) |
| 23.86 | CH₃ | SO₂Ph |
| 23.87 | CH₃ | NH₂ |
| 23.88 | CH₃ | NHCH₃ |
| 23.89 | CH₃ | NCH₃Ph |
| 23.90 | CH₃ | N(CH₃)₂ |
| 23.91 | CH₃ | NPh₂ |
| 23.92 | CH₃ | CN |
| 23.93 | CH₃ | NO₂ |

TABLE 13

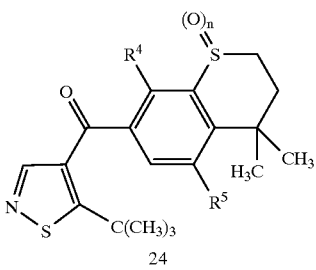

| No. | n | R⁴ | R⁵ |
|---|---|---|---|
| 24.1 | 0 | H | H |
| 24.2 | 0 | Cl | F |
| 24.3 | 0 | Cl | Cl |
| 24.4 | 0 | Cl | Br |
| 24.5 | 0 | Cl | CH₃ |
| 24.6 | 0 | Cl | C₂H₅ |
| 24.7 | 0 | Cl | nC₃H₇ |
| 24.8 | 0 | Cl | iC₃H₇ |
| 24.9 | 0 | Cl | nC₄H₉ |
| 24.10 | 0 | Cl | tC₄H₉ |
| 24.11 | 0 | Cl | Ph |
| 24.12 | 0 | Cl | OH |
| 24.13 | 0 | Cl | OCH₃ |
| 24.14 | 0 | Cl | OC₂H₅ |

TABLE 13-continued

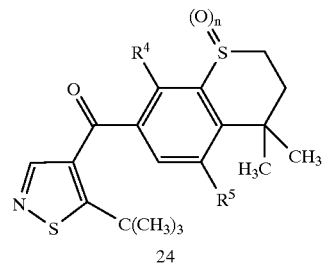

| No. | n | R⁴ | R⁵ |
|---|---|---|---|
| 24.15 | 0 | Cl | O(nC₃H₇) |
| 24.16 | 0 | Cl | O(iC₃H₇) |
| 24.17 | 0 | Cl | O(nC₄H₉) |
| 24.18 | 0 | Cl | O(tC₄H₉) |
| 24.19 | 0 | Cl | OPh |
| 24.20 | 0 | Cl | SH |
| 24.21 | 0 | Cl | SCH₃ |
| 24.22 | 0 | Cl | SC₂H₅ |
| 24.23 | 0 | Cl | S(nC₃H₇) |
| 24.24 | 0 | Cl | S(iC₃H₇) |
| 24.25 | 0 | Cl | S(nC₄H₉) |
| 24.26 | 0 | Cl | S(tC₄H₉) |
| 24.27 | 0 | Cl | SPh |
| 24.28 | 0 | Cl | CCl₃ |
| 24.29 | 0 | Cl | CH₂F |
| 24.30 | 0 | Cl | CHF₂ |
| 24.31 | 0 | Cl | CF₃ |
| 24.32 | 0 | Cl | CF₂CHF₂ |
| 24.33 | 0 | Cl | SO₃H |
| 24.34 | 0 | Cl | SO₂CH₃ |
| 24.35 | 0 | Cl | SO₂C₂H₅ |
| 24.36 | 0 | Cl | SO₂(nC₃H₇) |
| 24.37 | 0 | Cl | SO₂(iC₃H₇) |
| 24.38 | 0 | Cl | SO₂(nC₄H₉) |
| 24.39 | 0 | Cl | SO₂(tC₄H₉) |
| 24.40 | 0 | Cl | SO₂Ph |
| 24.41 | 0 | Cl | NH₂ |
| 24.42 | 0 | Cl | NHCH₃ |
| 24.43 | 0 | Cl | NCH₃Ph |
| 24.44 | 0 | Cl | N(CH₃)₂ |
| 24.45 | 0 | Cl | NPh₂ |
| 24.46 | 0 | Cl | CN |
| 24.47 | 0 | Cl | NO₂ |
| 24.47 | 0 | Cl | NO₂ |
| 24.48 | 0 | CH₃ | F |
| 24.49 | 0 | CH₃ | Cl |
| 24.50 | 0 | CH₃ | Br |
| 24.51 | 0 | CH₃ | CH₃ |
| 24.52 | 0 | CH₃ | C₂H₅ |
| 24.53 | 0 | CH₃ | nC₃H₇ |
| 24.54 | 0 | CH₃ | iC₃H₇ |
| 24.55 | 0 | CH₃ | nC₄H₉ |
| 24.56 | 0 | CH₃ | tC₄H₉ |
| 24.57 | 0 | CH₃ | Ph |
| 24.58 | 0 | CH₃ | OH |
| 24.59 | 0 | CH₃ | OCH₃ |
| 24.60 | 0 | CH₃ | OC₂H₅ |
| 24.61 | 0 | CH₃ | O(nC₃H₇) |
| 24.62 | 0 | CH₃ | O(iC₃H₇) |
| 24.63 | 0 | CH₃ | O(nC₄H₉) |
| 24.64 | 0 | CH₃ | O(tC₄H₉) |
| 24.65 | 0 | CH₃ | OPh |
| 24.66 | 0 | CH₃ | SH |
| 24.67 | 0 | CH₃ | SCH₃ |
| 24.68 | 0 | CH₃ | SC₂H₅ |
| 24.69 | 0 | CH₃ | S(nC₃H₇) |
| 24.70 | 0 | CH₃ | S(iC₃H₇) |
| 24.71 | 0 | CH₃ | S(nC₄H₉) |
| 24.72 | 0 | CH₃ | S(tC₄H₉) |
| 24.73 | 0 | CH₃ | SPh |
| 24.74 | 0 | CH₃ | CCl₃ |
| 24.75 | 0 | CH₃ | CH₂F |
| 24.76 | 0 | CH₃ | CHF₂ |

TABLE 13-continued

| No. | n | R⁴ | R⁵ |
|---|---|---|---|
| 24.77 | 0 | CH₃ | CF₃ |
| 24.78 | 0 | CH₃ | CF₂CHF₂ |
| 24.79 | 0 | CH₃ | SO₃H |
| 24.80 | 0 | CH₃ | SO₂CH₃ |
| 24.81 | 0 | CH₃ | SO₂C₂H₅ |
| 24.82 | 0 | CH₃ | SO₂(nC₃H₇) |
| 24.83 | 0 | CH₃ | SO₂(iC₃H₇) |
| 24.84 | 0 | CH₃ | SO₂(nC₄H₉) |
| 24.85 | 0 | CH₃ | SO₂(tC₄H₉) |
| 24.86 | 0 | CH₃ | SO₂Ph |
| 24.87 | 0 | CH₃ | NH₂ |
| 24.88 | 0 | CH₃ | NHCH₃ |
| 24.89 | 0 | CH₃ | NCH₃Ph |
| 24.90 | 0 | CH₃ | N(CH₃)₂ |
| 24.91 | 0 | CH₃ | NPh₂ |
| 24.92 | 0 | CH₃ | CN |
| 24.93 | 0 | CH₃ | NO₂ |
| 24.94 | 2 | Cl | F |
| 24.95 | 2 | Cl | Cl |
| 24.96 | 2 | Cl | Br |
| 24.97 | 2 | Cl | CH₃ |
| 24.98 | 2 | Cl | C₂H₅ |
| 24.99 | 2 | Cl | nC₃H₇ |
| 24.100 | 2 | Cl | iC₃H₇ |
| 24.101 | 2 | Cl | nC₄H₉ |
| 24.102 | 2 | Cl | tC₄H₉ |
| 24.103 | 2 | Cl | Ph |
| 24.104 | 2 | Cl | OH |
| 24.105 | 2 | Cl | OCH₃ |
| 24.106 | 2 | Cl | OC₂H₅ |
| 24.107 | 2 | Cl | O(nC₃H₇) |
| 24.108 | 2 | Cl | O(iC₃H₇) |
| 24.109 | 2 | Cl | O(nC₄H₉) |
| 24.110 | 2 | Cl | O(tC₄H₉) |
| 24.111 | 2 | Cl | OPh |
| 24.112 | 2 | Cl | SH |
| 24.113 | 2 | Cl | SCH₃ |
| 24.114 | 2 | Cl | SC₂H₅ |
| 24.115 | 2 | Cl | S(nC₃H₇) |
| 24.116 | 2 | Cl | S(iC₃H₇) |
| 24.117 | 2 | Cl | S(nC₄H₉) |
| 24.118 | 2 | Cl | S(tC₄H₉) |
| 24.119 | 2 | Cl | SPh |
| 24.120 | 2 | Cl | CCl₃ |
| 24.121 | 2 | Cl | CH₂F |
| 24.122 | 2 | Cl | CHF₂ |
| 24.123 | 2 | Cl | CF₃ |
| 24.124 | 2 | Cl | CF₂CHF₂ |
| 24.125 | 2 | Cl | SO₃H |
| 24.126 | 2 | Cl | SO₂CH₃ |
| 24.127 | 2 | Cl | SO₂C₂H₅ |
| 24.128 | 2 | Cl | SO₂(nC₃H₇) |
| 24.129 | 2 | Cl | SO₂(iC₃H₇) |
| 24.130 | 2 | Cl | SO₂(nC₄H₉) |
| 24.131 | 2 | Cl | SO₂(tC₄H₉) |
| 24.132 | 2 | Cl | SO₂Ph |
| 24.133 | 2 | Cl | NH₂ |
| 24.134 | 2 | Cl | NHCH₃ |
| 24.135 | 2 | Cl | NCH₃Ph |
| 24.136 | 2 | Cl | N(CH₃)₂ |
| 24.137 | 2 | Cl | NPh₂ |
| 24.138 | 2 | Cl | CN |
| 24.139 | 2 | Cl | NO₂ |
| 24.140 | 2 | CH₃ | F |
| 24.141 | 2 | CH₃ | Cl |
| 24.142 | 2 | CH₃ | Br |
| 24.143 | 2 | CH₃ | CH₃ |
| 24.144 | 2 | CH₃ | C₂H₅ |
| 24.145 | 2 | CH₃ | nC₃H₇ |
| 24.146 | 2 | CH₃ | iC₃H₇ |
| 24.147 | 2 | CH₃ | nC₄H₉ |
| 24.148 | 2 | CH₃ | tC₄H₉ |
| 24.149 | 2 | CH₃ | Ph |
| 24.150 | 2 | CH₃ | OH |
| 24.151 | 2 | CH₃ | OCH₃ |
| 24.152 | 2 | CH₃ | OC₂H₅ |
| 24.153 | 2 | CH₃ | O(nC₃H₇) |
| 24.154 | 2 | CH₃ | O(iC₃H₇) |
| 24.155 | 2 | CH₃ | O(nC₄H₉) |
| 24.156 | 2 | CH₃ | O(tC₄H₉) |
| 24.157 | 2 | CH₃ | OPh |
| 24.158 | 2 | CH₃ | SH |
| 24.159 | 2 | CH₃ | SCH₃ |
| 24.160 | 2 | CH₃ | SC₂H₅ |
| 24.161 | 2 | CH₃ | S(nC₃H₇) |
| 24.162 | 2 | CH₃ | S(iC₃H₇) |
| 24.163 | 2 | CH₃ | S(nC₄H₉) |
| 24.164 | 2 | CH₃ | S(tC₄H₉) |
| 24.165 | 2 | CH₃ | SPh |
| 24.166 | 2 | CH₃ | CCl₃ |
| 24.167 | 2 | CH₃ | CH₂F |
| 24.168 | 2 | CH₃ | CHF₂ |
| 24.169 | 2 | CH₃ | CF₃ |
| 24.170 | 2 | CH₃ | CF₂CHF₂ |
| 24.171 | 2 | CH₃ | SO₃H |
| 24.172 | 2 | CH₃ | SO₂CH₃ |
| 24.173 | 2 | CH₃ | SO₂C₂H₅ |
| 24.174 | 2 | CH₃ | SO₂(nC₃H₇) |
| 24.175 | 2 | CH₃ | SO₂(iC₃H₇) |
| 24.176 | 2 | CH₃ | SO₂(nC₄H₉) |
| 24.177 | 2 | CH₃ | SO₂(tC₄H₉) |
| 24.178 | 2 | CH₃ | SO₂Ph |
| 24.179 | 2 | CH₃ | NH₂ |
| 24.180 | 2 | CH₃ | NHCH₃ |
| 24.181 | 2 | CH₃ | NCH₃Ph |
| 24.182 | 2 | CH₃ | N(CH₃)₂ |
| 24.183 | 2 | CH₃ | NPh₂ |
| 24.184 | 2 | CH₃ | CN |
| 24.185 | 2 | CH₃ | NO₂ |

TABLE 14

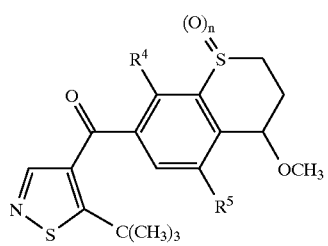

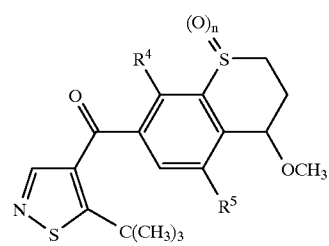

| No. | n | R⁴ | R⁵ |
|---|---|---|---|
| 25.1 | 0 | H | H |
| 25.2 | 0 | Cl | F |
| 25.3 | 0 | Cl | Cl |
| 25.4 | 0 | Cl | Br |
| 25.5 | 0 | Cl | CH₃ |
| 25.6 | 0 | Cl | C₂H₅ |
| 25.7 | 0 | Cl | nC₃H₇ |
| 25.8 | 0 | Cl | iC₃H₇ |
| 25.9 | 0 | Cl | nC₄H₉ |
| 25.10 | 0 | Cl | tC₄H₉ |
| 25.11 | 0 | Cl | Ph |
| 25.12 | 0 | Cl | OH |
| 25.13 | 0 | Cl | OCH₃ |
| 25.14 | 0 | Cl | OC₂H₅ |
| 25.15 | 0 | Cl | O(nC₃H₇) |
| 25.16 | 0 | Cl | O(iC₃H₇) |
| 25.17 | 0 | Cl | O(nC₄H₉) |
| 25.18 | 0 | Cl | O(tC₄H₉) |
| 25.19 | 0 | Cl | OPh |
| 25.20 | 0 | Cl | SH |
| 25.21 | 0 | Cl | SCH₃ |
| 25.22 | 0 | Cl | SC₂H₅ |
| 25.23 | 0 | Cl | S(nC₃H₇) |
| 25.24 | 0 | Cl | S(iC₃H₇) |
| 25.25 | 0 | Cl | S(nC₄H₉) |
| 25.26 | 0 | Cl | S(tC₄H₉) |
| 25.27 | 0 | Cl | SPh |
| 25.28 | 0 | Cl | CCl₃ |
| 25.29 | 0 | Cl | CH₂F |
| 25.30 | 0 | Cl | CHF₂ |
| 25.31 | 0 | Cl | CF₃ |
| 25.32 | 0 | Cl | CF₂CHF₂ |
| 25.33 | 0 | Cl | SO₃H |
| 25.34 | 0 | Cl | SO₂CH₃ |
| 25.35 | 0 | Cl | SO₂C₂H₅ |
| 25.36 | 0 | Cl | SO₂(nC₃H₇) |
| 25.37 | 0 | Cl | SO₂(iC₃H₇) |
| 25.38 | 0 | Cl | SO₂(nC₄H₉) |
| 25.39 | 0 | Cl | SO₂(tC₄H₉) |
| 25.40 | 0 | Cl | SO₂Ph |
| 25.41 | 0 | Cl | NH₂ |
| 25.42 | 0 | Cl | NHCH₃ |
| 25.43 | 0 | Cl | NCH₃Ph |
| 25.44 | 0 | Cl | N(CH₃)₂ |
| 25.45 | 0 | Cl | NPh₂ |
| 25.46 | 0 | Cl | CN |
| 25.47 | 0 | Cl | NO₂ |
| 25.48 | 0 | CH₃ | F |
| 25.49 | 0 | CH₃ | Cl |
| 25.50 | 0 | CH₃ | Br |
| 25.51 | 0 | CH₃ | CH₃ |
| 25.52 | 0 | CH₃ | C₂H₅ |
| 25.53 | 0 | CH₃ | nC₃H₇ |
| 25.54 | 0 | CH₃ | iC₃H₇ |
| 25.55 | 0 | CH₃ | nC₄H₉ |
| 25.56 | 0 | CH₃ | tC₄H₉ |
| 25.57 | 0 | CH₃ | Ph |
| 25.58 | 0 | CH₃ | OH |
| 25.59 | 0 | CH₃ | OCH₃ |
| 25.60 | 0 | CH₃ | OC₂H₅ |
| 25.61 | 0 | CH₃ | O(nC₃H₇) |
| 25.62 | 0 | CH₃ | O(iC₃H₇) |
| 25.63 | 0 | CH₃ | O(nC₄H₉) |
| 25.64 | 0 | CH₃ | O(tC₄H₉) |
| 25.65 | 0 | CH₃ | OPh |
| 25.66 | 0 | CH₃ | SH |
| 25.67 | 0 | CH₃ | SCH₃ |
| 25.68 | 0 | CH₃ | SC₂H₅ |
| 25.69 | 0 | CH₃ | S(nC₃H₇) |
| 25.70 | 0 | CH₃ | S(iC₃H₇) |
| 25.71 | 0 | CH₃ | S(nC₄H₉) |
| 25.72 | 0 | CH₃ | S(tC₄H₉) |
| 25.73 | 0 | CH₃ | SPh |
| 25.74 | 0 | CH₃ | CCl₃ |
| 25.75 | 0 | CH₃ | CH₂F |
| 25.76 | 0 | CH₃ | CHF₂ |
| 25.77 | 0 | CH₃ | CF₃ |
| 25.78 | 0 | CH₃ | CF₂CHF₂ |
| 25.79 | 0 | CH₃ | SO₃H |
| 25.80 | 0 | CH₃ | SO₂CH₃ |
| 25.81 | 0 | CH₃ | SO₂C₂H₅ |
| 25.82 | 0 | CH₃ | SO₂(nC₃H₇) |
| 25.83 | 0 | CH₃ | SO₂(iC₃H₇) |
| 25.84 | 0 | CH₃ | SO₂(nC₄H₉) |
| 25.85 | 0 | CH₃ | SO₂(tC₄H₉) |
| 25.86 | 0 | CH₃ | SO₂Ph |
| 25.87 | 0 | CH₃ | NH₂ |
| 25.88 | 0 | CH₃ | NHCH₃ |
| 25.89 | 0 | CH₃ | NCH₃Ph |
| 25.90 | 0 | CH₃ | N(CH₃)₂ |
| 25.91 | 0 | CH₃ | NPh₂ |
| 25.92 | 0 | CH₃ | CN |
| 25.93 | 0 | CH₃ | NO₂ |
| 25.94 | 2 | Cl | F |
| 25.95 | 2 | Cl | Cl |
| 25.96 | 2 | Cl | Br |
| 25.97 | 2 | Cl | CH₃ |
| 25.98 | 2 | Cl | C₂H₅ |
| 25.99 | 2 | Cl | nC₃H₇ |
| 25.100 | 2 | Cl | iC₃H₇ |
| 25.101 | 2 | Cl | nC₄H₉ |
| 25.102 | 2 | Cl | tC₄H₉ |
| 25.103 | 2 | Cl | Ph |
| 25.104 | 2 | Cl | OH |
| 25.105 | 2 | Cl | OCH₃ |
| 25.106 | 2 | Cl | OC₂H₅ |
| 25.107 | 2 | Cl | O(nC₃H₇) |
| 25.108 | 2 | Cl | O(iC₃H₇) |
| 25.109 | 2 | Cl | O(nC₄H₉) |
| 25.110 | 2 | Cl | O(tC₄H₉) |
| 25.111 | 2 | Cl | OPh |
| 25.112 | 2 | Cl | SH |
| 25.113 | 2 | Cl | SCH₃ |
| 25.114 | 2 | Cl | SC₂H₅ |
| 25.115 | 2 | Cl | S(nC₃H₇) |
| 25.116 | 2 | Cl | S(iC₃H₇) |
| 25.117 | 2 | Cl | S(nC₄H₉) |
| 25.118 | 2 | Cl | S(tC₄H₉) |
| 25.119 | 2 | Cl | SPh |
| 25.120 | 2 | Cl | CCl₃ |
| 25.121 | 2 | Cl | CH₂F |
| 25.122 | 2 | Cl | CHF₂ |
| 25.123 | 2 | Cl | CF₃ |
| 25.124 | 2 | Cl | CF₂CHF₂ |
| 25.125 | 2 | Cl | SO₃H |
| 25.126 | 2 | Cl | SO₂CH₃ |

TABLE 14-continued

25

[Structure: bicyclic thiopyran with (O)ₙ on sulfur, R⁴ at position 8, carbonyl linked to isothiazole bearing C(CH₃)₃, OCH₃ group on saturated ring, R⁵ at position 5]

| No. | n | R⁴ | R⁵ |
|---|---|---|---|
| 25.127 | 2 | Cl | SO₂C₂H₅ |
| 25.128 | 2 | Cl | SO₂(nC₃H₇) |
| 25.129 | 2 | Cl | SO₂(iC₃H₇) |
| 25.130 | 2 | Cl | SO₂(nC₄H₉) |
| 25.131 | 2 | Cl | SO₂(tC₄H₉) |
| 25.132 | 2 | Cl | SO₂Ph |
| 25.133 | 2 | Cl | NH₂ |
| 25.134 | 2 | Cl | NHCH₃ |
| 25.135 | 2 | Cl | NCH₃Ph |
| 25.136 | 2 | Cl | N(CH₃)₂ |
| 25.137 | 2 | Cl | NPh₂ |
| 25.138 | 2 | Cl | CN |
| 25.139 | 2 | Cl | NO₂ |
| 25.140 | 2 | CH₃ | F |
| 25.141 | 2 | CH₃ | Cl |
| 25.142 | 2 | CH₃ | Br |
| 25.143 | 2 | CH₃ | CH₃ |
| 25.144 | 2 | CH₃ | C₂H₅ |
| 25.145 | 2 | CH₃ | nC₃H₇ |
| 25.146 | 2 | CH₃ | iC₃H₇ |
| 25.147 | 2 | CH₃ | nC₄H₉ |
| 25.148 | 2 | CH₃ | tC₄H₉ |
| 25.149 | 2 | CH₃ | Ph |
| 25.150 | 2 | CH₃ | OH |
| 25.151 | 2 | CH₃ | OCH₃ |
| 25.152 | 2 | CH₃ | OC₂H₅ |
| 25.153 | 2 | CH₃ | O(nC₃H₇) |
| 25.154 | 2 | CH₃ | O(iC₃H₇) |
| 25.155 | 2 | CH₃ | O(nC₄H₉) |
| 25.156 | 2 | CH₃ | O(tC₄H₉) |
| 25.157 | 2 | CH₃ | OPh |
| 25.158 | 2 | CH₃ | SH |
| 25.159 | 2 | CH₃ | SCH₃ |
| 25.160 | 2 | CH₃ | SC₂H₅ |
| 25.161 | 2 | CH₃ | S(nC₃H₇) |
| 25.162 | 2 | CH₃ | S(iC₃H₇) |
| 25.163 | 2 | CH₃ | S(nC₄H₉) |
| 25.164 | 2 | CH₃ | S(tC₄H₉) |
| 25.165 | 2 | CH₃ | SPh |
| 25.166 | 2 | CH₃ | CCl₃ |
| 25.167 | 2 | CH₃ | CH₂F |
| 25.168 | 2 | CH₃ | CHF₂ |
| 25.169 | 2 | CH₃ | CF₃ |
| 25.170 | 2 | CH₃ | CF₂CHF₂ |
| 25.171 | 2 | CH₃ | SO₃H |
| 25.172 | 2 | CH₃ | SO₂CH₃ |
| 25.173 | 2 | CH₃ | SO₂C₂H₅ |
| 25.174 | 2 | CH₃ | SO₂(nC₃H₇) |
| 25.175 | 2 | CH₃ | SO₂(iC₃H₇) |
| 25.176 | 2 | CH₃ | SO₂(nC₄H₉) |
| 25.177 | 2 | CH₃ | SO₂(tC₄H₉) |
| 25.178 | 2 | CH₃ | SO₂Ph |
| 25.179 | 2 | CH₃ | NH₂ |
| 25.180 | 2 | CH₃ | NHCH₃ |
| 25.181 | 2 | CH₃ | NCH₃Ph |
| 25.182 | 2 | CH₃ | N(CH₃)₂ |
| 25.183 | 2 | CH₃ | NPh₂ |
| 25.184 | 2 | CH₃ | CN |
| 25.185 | 2 | CH₃ | NO₂ |

TABLE 15

26

[Structure: benzo-fused 1,4-oxathiine with (O)ₙ on sulfur, R⁴, carbonyl linked to isothiazole bearing C(CH₃)₃, R⁵]

| No. | n | R⁴ | R⁵ |
|---|---|---|---|
| 26.1 | 0 | H | H |
| 26.2 | 0 | Cl | F |
| 26.3 | 0 | Cl | Cl |
| 26.4 | 0 | Cl | Br |
| 26.5 | 0 | Cl | CH₃ |
| 26.6 | 0 | Cl | C₂H₅ |
| 26.7 | 0 | Cl | nC₃H₇ |
| 26.8 | 0 | Cl | iC₃H₇ |
| 26.9 | 0 | Cl | nC₄H₉ |
| 26.10 | 0 | Cl | tC₄H₉ |
| 26.11 | 0 | Cl | Ph |
| 26.12 | 0 | Cl | OH |
| 26.13 | 0 | Cl | OCH₃ |
| 26.14 | 0 | Cl | OC₂H₅ |
| 26.15 | 0 | Cl | O(nC₃H₇) |
| 26.16 | 0 | Cl | O(iC₃H₇) |
| 26.17 | 0 | Cl | O(nC₄H₉) |
| 26.18 | 0 | Cl | O(tC₄H₉) |
| 26.19 | 0 | Cl | OPh |
| 26.20 | 0 | Cl | SH |
| 26.21 | 0 | Cl | SCH₃ |
| 26.22 | 0 | Cl | SC₂H₅ |
| 26.23 | 0 | Cl | S(nC₃H₇) |
| 26.24 | 0 | Cl | S(iC₃H₇) |
| 26.25 | 0 | Cl | S(nC₄H₉) |
| 26.26 | 0 | Cl | S(tC₄H₉) |
| 26.27 | 0 | Cl | SPh |
| 26.28 | 0 | Cl | CCl₃ |
| 26.29 | 0 | Cl | CH₂F |
| 26.30 | 0 | Cl | CHF₂ |
| 26.31 | 0 | Cl | CF₃ |
| 26.32 | 0 | Cl | CF₂CHF₂ |
| 26.33 | 0 | Cl | SO₃H |
| 26.34 | 0 | Cl | SO₂CH₃ |
| 26.35 | 0 | Cl | SO₂C₂H₅ |
| 26.36 | 0 | Cl | SO₂(nC₃H₇) |
| 26.37 | 0 | Cl | SO₂(iC₃H₇) |
| 26.38 | 0 | Cl | SO₂(nC₄H₉) |
| 26.39 | 0 | Cl | SO₂(tC₄H₉) |
| 26.40 | 0 | Cl | SO₂Ph |
| 26.41 | 0 | Cl | NH₂ |
| 26.42 | 0 | Cl | NHCH₃ |
| 26.43 | 0 | Cl | NCH₃Ph |
| 26.44 | 0 | Cl | N(CH₃)₂ |
| 26.45 | 0 | Cl | NPh₂ |
| 26.46 | 0 | Cl | CN |
| 26.47 | 0 | Cl | NO₂ |
| 26.48 | 0 | CH₃ | F |
| 26.49 | 0 | CH₃ | Cl |
| 26.50 | 0 | CH₃ | Br |
| 26.51 | 0 | CH₃ | CH₃ |
| 26.52 | 0 | CH₃ | C₂H₅ |
| 26.53 | 0 | CH₃ | nC₃H₇ |
| 26.54 | 0 | CH₃ | iC₃H₇ |
| 26.55 | 0 | CH₃ | nC₄H₉ |
| 26.56 | 0 | CH₃ | tC₄H₉ |
| 26.57 | 0 | CH₃ | Ph |
| 26.58 | 0 | CH₃ | OH |
| 26.59 | 0 | CH₃ | OCH₃ |
| 26.60 | 0 | CH₃ | OC₂H₅ |
| 26.61 | 0 | CH₃ | O(nC₃H₇) |
| 26.62 | 0 | CH₃ | O(iC₃H₇) |
| 26.63 | 0 | CH₃ | O(nC₄H₉) |

TABLE 15-continued

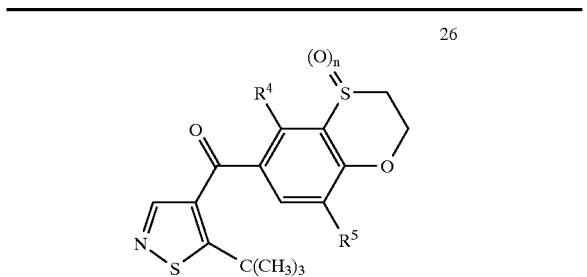

| No. | n | R⁴ | R⁵ |
|---|---|---|---|
| 26.64 | 0 | CH₃ | O(tC₄H₉) |
| 26.65 | 0 | CH₃ | OPh |
| 26.66 | 0 | CH₃ | SH |
| 26.67 | 0 | CH₃ | SCH₃ |
| 26.68 | 0 | CH₃ | SC₂H₅ |
| 26.69 | 0 | CH₃ | S(nC₃H₇) |
| 26.70 | 0 | CH₃ | S(iC₃H₇) |
| 26.71 | 0 | CH₃ | S(nC₄H₉) |
| 26.72 | 0 | CH₃ | S(tC₄H₉) |
| 26.73 | 0 | CH₃ | SPh |
| 26.74 | 0 | CH₃ | CCl₃ |
| 26.75 | 0 | CH₃ | CH₂F |
| 26.76 | 0 | CH₃ | CHF₂ |
| 26.77 | 0 | CH₃ | CF₃ |
| 26.78 | 0 | CH₃ | CF₂CHF₂ |
| 26.79 | 0 | CH₃ | SO₃H |
| 26.80 | 0 | CH₃ | SO₂CH₃ |
| 26.81 | 0 | CH₃ | SO₂C₂H₅ |
| 26.82 | 0 | CH₃ | SO₂(nC₃H₇) |
| 26.83 | 0 | CH₃ | SO₂(iC₃H₇) |
| 26.84 | 0 | CH₃ | SO₂(nC₄H₉) |
| 26.85 | 0 | CH₃ | SO₂(tC₄H₉) |
| 26.86 | 0 | CH₃ | SO₂Ph |
| 26.87 | 0 | CH₃ | NH₂ |
| 26.88 | 0 | CH₃ | NHCH₃ |
| 26.89 | 0 | CH₃ | NCH₃Ph |
| 26.90 | 0 | CH₃ | N(CH₃)₂ |
| 26.91 | 0 | CH₃ | NPh₂ |
| 26.92 | 0 | CH₃ | CN |
| 26.93 | 0 | CH₃ | NO₂ |
| 26.94 | 2 | Cl | F |
| 26.95 | 2 | Cl | Cl |
| 26.96 | 2 | Cl | Br |
| 26.97 | 2 | Cl | CH₃ |
| 26.98 | 2 | Cl | C₂H₅ |
| 26.99 | 2 | Cl | nC₃H₇ |
| 26.100 | 2 | Cl | iC₃H₇ |
| 26.101 | 2 | Cl | nC₄H₉ |
| 26.102 | 2 | Cl | tC₄H₉ |
| 26.103 | 2 | Cl | Ph |
| 26.104 | 2 | Cl | OH |
| 26.105 | 2 | Cl | OCH₃ |
| 26.106 | 2 | Cl | OC₂H₅ |
| 26.107 | 2 | Cl | O(nC₃H₇) |
| 26.108 | 2 | Cl | O(iC₃H₇) |
| 26.109 | 2 | Cl | O(nC₄H₉) |
| 26.110 | 2 | Cl | O(tC₄H₉) |
| 26.111 | 2 | Cl | OPh |
| 26.112 | 2 | Cl | SH |
| 26.113 | 2 | Cl | SCH₃ |
| 26.114 | 2 | Cl | SC₂H₅ |
| 26.115 | 2 | Cl | S(nC₃H₇) |
| 26.116 | 2 | Cl | S(iC₃H₇) |
| 26.117 | 2 | Cl | S(nC₄H₉) |
| 26.118 | 2 | Cl | S(tC₄H₉) |
| 26.119 | 2 | Cl | SPh |
| 26.120 | 2 | Cl | CCl₃ |
| 26.121 | 2 | Cl | CH₂F |
| 26.122 | 2 | Cl | CHF₂ |
| 26.123 | 2 | Cl | CF₃ |
| 26.124 | 2 | Cl | CF₂CHF₂ |
| 26.125 | 2 | Cl | SO₃H |
| 26.126 | 2 | Cl | SO₂CH₃ |
| 26.127 | 2 | Cl | SO₂C₂H₅ |
| 26.128 | 2 | Cl | SO₂(nC₃H₇) |
| 26.129 | 2 | Cl | SO₂(iC₃H₇) |
| 26.130 | 2 | Cl | SO₂(nC₄H₉) |
| 26.131 | 2 | Cl | SO₂(tC₄H₉) |
| 26.132 | 2 | Cl | SO₂Ph |
| 26.133 | 2 | Cl | NH₂ |
| 26.134 | 2 | Cl | NHCH₃ |
| 26.135 | 2 | Cl | NCH₃Ph |
| 26.136 | 2 | Cl | N(CH₃)₂ |
| 26.137 | 2 | Cl | NPh₂ |
| 26.138 | 2 | Cl | CN |
| 26.139 | 2 | Cl | NO₂ |
| 26.140 | 2 | CH₃ | F |
| 26.141 | 2 | CH₃ | Cl |
| 26.142 | 2 | CH₃ | Br |
| 26.143 | 2 | CH₃ | CH₃ |
| 26.144 | 2 | CH₃ | C₂H₅ |
| 26.145 | 2 | CH₃ | nC₃H₇ |
| 26.146 | 2 | CH₃ | iC₃H₇ |
| 26.147 | 2 | CH₃ | nC₄H₉ |
| 26.148 | 2 | CH₃ | tC₄H₉ |
| 26.149 | 2 | CH₃ | Ph |
| 26.150 | 2 | CH₃ | OH |
| 26.151 | 2 | CH₃ | OCH₃ |
| 26.152 | 2 | CH₃ | OC₂H₅ |
| 26.153 | 2 | CH₃ | O(nC₃H₇) |
| 26.154 | 2 | CH₃ | O(iC₃H₇) |
| 26.155 | 2 | CH₃ | O(nC₄H₉) |
| 26.156 | 2 | CH₃ | O(tC₄H₉) |
| 26.157 | 2 | CH₃ | OPh |
| 26.158 | 2 | CH₃ | SH |
| 26.159 | 2 | CH₃ | SCH₃ |
| 26.160 | 2 | CH₃ | SC₂H₅ |
| 26.161 | 2 | CH₃ | S(nC₃H₇) |
| 26.162 | 2 | CH₃ | S(iC₃H₇) |
| 26.163 | 2 | CH₃ | S(nC₄H₉) |
| 26.164 | 2 | CH₃ | S(tC₄H₉) |
| 26.165 | 2 | CH₃ | SPh |
| 26.166 | 2 | CH₃ | CCl₃ |
| 26.167 | 2 | CH₃ | CH₂F |
| 26.168 | 2 | CH₃ | CHF₂ |
| 26.169 | 2 | CH₃ | CF₃ |
| 26.170 | 2 | CH₃ | CF₂CHF₂ |
| 26.171 | 2 | CH₃ | SO₃H |
| 26.172 | 2 | CH₃ | SO₂CH₃ |
| 26.173 | 2 | CH₃ | SO₂C₂H₅ |
| 26.174 | 2 | CH₃ | SO₂(nC₃H₇) |
| 26.175 | 2 | CH₃ | SO₂(iC₃H₇) |
| 26.176 | 2 | CH₃ | SO₂(nC₄H₉) |
| 26.177 | 2 | CH₃ | SO₂(tC₄H₉) |
| 26.178 | 2 | CH₃ | SO₂Ph |
| 26.179 | 2 | CH₃ | NH₂ |
| 26.180 | 2 | CH₃ | NHCH₃ |
| 26.181 | 2 | CH₃ | NCH₃Ph |
| 26.182 | 2 | CH₃ | N(CH₃)₂ |
| 26.183 | 2 | CH₃ | NPh₂ |
| 26.184 | 2 | CH₃ | CN |
| 26.185 | 2 | CH₃ | NO₂ |

TABLE 16

Structure 27: R⁴ and R⁵ substituted benzo-dioxine with isothiazole-C(CH₃)₃ ketone

| No. | R⁴ | R⁵ |
|---|---|---|
| 27.1 | H | H |
| 27.2 | Cl | F |
| 27.3 | Cl | Cl |
| 27.4 | Cl | Br |
| 27.5 | Cl | $CH_3$ |
| 27.6 | Cl | $C_2H_5$ |
| 27.7 | Cl | $nC_3H_7$ |
| 27.8 | Cl | $iC_3H_7$ |
| 27.9 | Cl | $nC_4H_9$ |
| 27.10 | Cl | $tC_4H_9$ |
| 27.11 | Cl | Ph |
| 27.12 | Cl | OH |
| 27.13 | Cl | $OCH_3$ |
| 27.14 | Cl | $OC_2H_5$ |
| 27.15 | Cl | $O(nC_3H_7)$ |
| 27.16 | Cl | $O(iC_3H_7)$ |
| 27.17 | Cl | $O(nC_4H_9)$ |
| 27.18 | Cl | $O(tC_4H_9)$ |
| 27.19 | Cl | OPh |
| 27.20 | Cl | SH |
| 27.21 | Cl | $SCH_3$ |
| 27.22 | Cl | $SC_2H_5$ |
| 27.23 | Cl | $S(nC_3H_7)$ |
| 27.24 | Cl | $S(iC_3H_7)$ |
| 27.25 | Cl | $S(nC_4H_9)$ |
| 27.26 | Cl | $S(tC_4H_9)$ |
| 27.27 | Cl | SPh |
| 27.28 | Cl | $CCl_3$ |
| 27.29 | Cl | $CH_2F$ |
| 27.30 | Cl | $CHF_2$ |
| 27.31 | Cl | $CF_3$ |
| 27.32 | Cl | $CF_2CHF_2$ |
| 27.33 | Cl | $SO_3H$ |
| 27.34 | Cl | $SO_2CH_3$ |
| 27.35 | Cl | $SO_2C_2H_5$ |
| 27.36 | Cl | $SO_2(nC_3H_7)$ |
| 27.37 | Cl | $SO_2(iC_3H_7)$ |
| 27.38 | Cl | $SO_2(nC_4H_9)$ |
| 27.39 | Cl | $SO_2(tC_4H_9)$ |
| 27.40 | Cl | $SO_2Ph$ |
| 27.41 | Cl | $NH_2$ |
| 27.42 | Cl | $NHCH_3$ |
| 27.43 | Cl | $NCH_3Ph$ |
| 27.44 | Cl | $N(CH_3)_2$ |
| 27.45 | Cl | $NPh_2$ |
| 27.46 | Cl | CN |
| 27.47 | Cl | $NO_2$ |
| 27.48 | $CH_3$ | F |
| 27.49 | $CH_3$ | Cl |
| 27.50 | $CH_3$ | Br |
| 27.51 | $CH_3$ | $CH_3$ |
| 27.52 | $CH_3$ | $C_2H_5$ |
| 27.53 | $CH_3$ | $nC_3H_7$ |
| 27.54 | $CH_3$ | $iC_3H_7$ |
| 27.55 | $CH_3$ | $nC_4H_9$ |
| 27.56 | $CH_3$ | $tC_4H_9$ |
| 27.57 | $CH_3$ | Ph |
| 27.58 | $CH_3$ | OH |
| 27.59 | $CH_3$ | $OCH_3$ |
| 27.60 | $CH_3$ | $OC_2H_5$ |
| 27.61 | $CH_3$ | $O(nC_3H_7)$ |
| 27.62 | $CH_3$ | $O(iC_3H_7)$ |
| 27.63 | $CH_3$ | $O(nC_4H_9)$ |
| 27.64 | $CH_3$ | $O(tC_4H_9)$ |
| 27.65 | $CH_3$ | OPh |
| 27.66 | $CH_3$ | SH |
| 27.67 | $CH_3$ | $SCH_3$ |
| 27.68 | $CH_3$ | $SC_2H_5$ |
| 27.69 | $CH_3$ | $S(nC_3H_7)$ |
| 27.70 | $CH_3$ | $S(iC_3H_7)$ |
| 27.71 | $CH_3$ | $S(nC_4H_9)$ |
| 27.72 | $CH_3$ | $S(tC_4H_9)$ |
| 27.73 | $CH_3$ | SPh |
| 27.74 | $CH_3$ | $CCl_3$ |
| 27.75 | $CH_3$ | $CH_2F$ |
| 27.76 | $CH_3$ | $CHF_2$ |
| 27.77 | $CH_3$ | $CF_3$ |
| 27.78 | $CH_3$ | $CF_2CHF_2$ |
| 27.79 | $CH_3$ | $SO_3H$ |
| 27.80 | $CH_3$ | $SO_2CH_3$ |
| 27.81 | $CH_3$ | $SO_2C_2H_5$ |
| 27.82 | $CH_3$ | $SO_2(nC_3H_7)$ |
| 27.83 | $CH_3$ | $SO_2(iC_3H_7)$ |
| 27.84 | $CH_3$ | $SO_2(nC_4H_9)$ |
| 27.85 | $CH_3$ | $SO_2(tC_4H_9)$ |
| 27.86 | $CH_3$ | $SO_2Ph$ |
| 27.87 | $CH_3$ | $NH_2$ |
| 27.88 | $CH_3$ | $NHCH_3$ |
| 27.89 | $CH_3$ | $NCH_3Ph$ |
| 27.90 | $CH_3$ | $N(CH_3)_2$ |
| 27.91 | $CH_3$ | $NPh_2$ |
| 27.92 | $CH_3$ | CN |
| 27.93 | $CH_3$ | $NO_2$ |

The compounds I and their agriculturally useful salts are suitable herbicides, both in the form of isomer mixtures and in the form of the pure isomers. The herbicidal compositions comprising I effect very good control of vegetation on non-crop areas, especially at high rates of application. In crops such as wheat, rice, maize (corn), soybeans and cotton, they act against broad-leaved weeds and grass weeds without damaging the crop plants to a significant extent. This effect is observed mainly at low rates of application.

Depending on the particular method of application, the compounds I, or compositions comprising them, can also be employed in a further number of crop plants for eliminating undesirable plants. The following are examples of suitable crops:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica,*

*Pyrus communis, Ribes sylestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

Moreover, the compounds I can also be used in crops which tolerate the activity of herbicides as a result of breeding, including genetic engineering methods.

The herbicidal compositions, or the active ingredients, can be applied pre- or post-emergence. If the active ingredients are less well tolerated by certain crop plants, application techniques may be used in which the herbicidal compositions are sprayed, with the aid of the spraying apparatus, in such a way that the leaves of the sensitive crop plants come into as little contact as possible, if any, with the active ingredients while the latter reach the leaves of undesirable plants growing underneath, or the bare soil (post-directed, lay-by).

The compounds I, or the herbicidal compositions comprising them, can be used for example in the form of ready-to-spray aqueous solutions, powders, suspensions, also highly concentrated aqueous oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

Suitable inert auxiliaries are essentially: mineral oil fractions of medium to high boiling point such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes or their derivatives, alkylated benzenes or their derivatives, alcohols such as methanol, ethanol, propanol, butanol, cyclohexanol, ketones such as cyclohexanone, or strongly polar solvents, eg. amines such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of wetting agent, tackifier, dispersant or emulsifier. Alternatively, it is possible to prepare concentrates comprising active ingredient, wetting agent, tackifier, dispersant or emulsifier and, if desired, solvent or oil which are suitable for dilution with water.

Suitable surfactants (adjuvants) are the alkali metal salts, alkaline earth metal salts and ammonium salts of aromatic sulfonic acids, eg. lignin-, phenol-, naphthalene- and dibutylnaphthalenesulfonic acid and of fatty acids, of alkyl- and alkylarylsulfonates, of alkyl, lauryl ether and fatty alcohol sulfates, and salts of sulfated hexa-, hepta- and octadecanols and of fatty alcohol glycol ether, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenyl and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin such as cereal meal, tree bark meal, wood flour, nutshell meal, cellulose powders, or other solid carriers.

The concentrations of the active ingredients I in the ready-to-use preparations can be varied within wide ranges. In general, the formulations comprise 0.001 to 98% by weight, preferably 0.01 to 95% by weight, of active ingredient. The active ingredients are employed in a purity of from 90% to 100%, preferably 95% to 100% (according to NMR spectrum).

For example, compound 28 according to the invention can be formulated as follows:

I. 20 parts by weight of compound 28 are dissolved in a mixture composed of 80 parts by weight of alkylateed benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution and finely distributing it in 100,000 parts by weight of water give an aqueous dispersion which comprises 0.02% by weight of the active ingredient.

II. 20 parts by weight of compound 28 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution and finely distributing it in 100,000 parts by weight of water give an aqueous dispersion which comprises 0.02% by weight of the active ingredient.

III. 20 parts by weight of active ingredient 28 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution and finely distributing it in 100,000 parts by weight of water give an aqueous dispersion which comprises 0.02% by weight of the active ingredient.

IV. 20 parts by weight of active ingredient 28 are mixed thoroughly with 3 parts by weight of sodium diisobutylnaphthalenesulfonate, 17 parts by weight of the sodium salt of a ligninsulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient 28 are mixed with 97 parts by weight of finely divided kaolin. This gives a dust which comprises 3% by weight of the active ingredient.

VI. 20 parts by weight of active ingredient 28 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of compound 28 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of compound 28 is dissolved in a mixture composed of 80 parts by weight of cyclohexanone and 20 parts by weight of Emulphor EL (ethoxylated castor oil). This gives a stable emulsion concentrate.

To widen the spectrum of action and to achieve synergistic effects, the heterocycle-fused benzoylisothiazole I can be mixed, and applied jointly, with a large number of representatives of other groups of herbicidal or growth-regulating ingredients. Suitable examples of components in mixtures are 1,2,4-thiadiazoles, 1,3,4-thiadiazoles, amides, aminophosphoric acid and its derivatives, aminotriazoles, anilides, (het)aryloxyalkanoic acid and its derivatives, benozic acid and its derivatives, benzothiadiazinones, 2-aroyl-1,3-cyclohexandiones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenbenzofurans, dihydrofuran-2-ones, dinitroanilines, dinitrophenols, diphenyl ethers, bipyridyls, halocarboxylic acids and their derivatives, ureas, 3-phenyluracils, imidazoles, imidazolinones, N-phenyl-3,4,5,6-tetrahydrophthalimides oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

for treating nutritional and trace element deficiencies. Non-phytotoxic oils and oil concentrates may also be added.

Depending on the intended purpose, the season, the target plants and the growth stage, the application rates of active ingredient are from 0.001 to 3.0, preferably 0.01 to 1.0, kg/ha of active substance (a.s.)

SYNTHESIS EXAMPLE

Synthesis of 4-(2',4'-dimethyl-5'-saccharinoyl)-5-cyclopropylisothiazole 28

The following operations are carried out with the exclusion of moisture. To 60 ml of a 1.4 M solution (0.08 mol) of methylmagnesium bromide in toluene/tetrahydrofuran 3:1 (v/v) there are added, with ice-cooling, 9.0 g (0.04 mol) of 4-iodo-5-cyclopropylisothiazole in 200 ml of tetrahydrofuran in such a way that the reaction temperature does not climb to above 5° C. The reaction mixture is treated with a solution of 21.9 g (0.08 mol) of 2,4-dimethylsaccharin-5-carbonyl chloride in 300 ml of tetrahydrofuran. After the exothermal reaction has subsided, remains of organometallic compounds are hydrolyzed with 100 ml of 10% strength hydrochloric acid. The reaction mixture is taken up in diethyl ether, worked up under aqueous conditions, dried with sodium sulfate, filtered and freed from solvent in vacuo. The crude product is purified on 250 g of silica gel using mixtures of cyclohexane/ethyl acetate 10:1 to 4:1 (v/v).

Yield: 5.2 g (36%) of colorless solid, 270 MHz $^1$H-NMR (CDCl$_3$), δ [ppm]: 1.0 (m, 2H), 1.4 (m, 2H), 2.8 (s, 3H), 3.0 (m, 1H), 3.3 (s, 3H), 7.8 (d, 1H), 7.9 (d, 1H), 8.3 (s, 1H).

TABLE 2

| No. | Formula | Physical Data m.p. [° C.]: 139–145 |
|---|---|---|
| 12 | | 1H-NMR (270 MHz; CDCl$_3$; in ppm): 0.9(m, 2H); 1.3(m, 2H); 1.4(t, 3H); 2.88(s, 3H); 2.95(m11H); 3.9(q, 2H); 7.9(s, 1H); 8.2(s, 1H) |
| 12 | | 1H-NMR (270 MHz; CDCl$_3$; in ppm): 0.9(m, 2H); 1.3(m, 5H); 2.9(m, 1H); 3.5(q, 2H); 7.5(d, 1H); 8.2(d, 1H), 8.25(s, 1H) |

Moreover, it may be advantageous to apply the compounds I, alone or in combination with other herbicides, together with even more crop protection products, for example with pesticides or compositions for controlling phytopathogenic fungi or bacteria. Also of interest is the miscibility with mineral salt solutions, which are employed

USE EXAMPLE

The herbicidal action of the heterocycle-fused benzoylisothiazoles of the formula I was demonstrated by greenouse experiments:

The culture containers used were plastic flower pots containing loamy sand with approximately 3.0% of humus as the substrate. The seeds of the test plant were sown separately for each species.

In the case of pre-emergence treatment, the active ingredients, which were suspended or emulsified in water, were applied directly after sowing, by means of finely distributing nozzles. The containers were irrigated gently to promote germination and growth and subequently covered with translucent plastic hoods until the plants had rooted. This cover results in uniform germination of the test plants unless germination was adversely affected by the active ingredients.

For post-emergence treatment, the test plants were first grown to a plant height of 3 to 15 cm, depending on the plant habit, and only then treated with the active ingredients which were suspended or emulsified in water. The test plants were either sown directly and grown in the same containers or grown separately as seedlings and transplanted to the test containers only a few days prior to treatment.

The rate of application for the post-emergence treatment was 0.5, or 0.25, kg/ha of a.s.

Depending on the species, the plants were kept at from 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belong to the following species:

| Scientific name | Common name |
|---|---|
| *Chenopodium album* | lambsquarters (goosefoot) |
| *Echinochloa crus-galli* | barnyardgrass |
| *Sinapis album* | white mustard |
| *Solanum nigrum* | black nightshade |

TABLE 17

Herbicidal activity in the greenhouse, post-emergence treatment

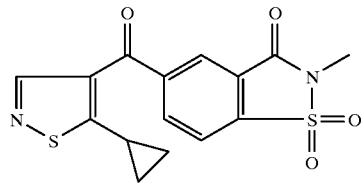

28

| Rate of application (kg/ha of a.s.) | 0.5 | 0.25 |
|---|---|---|
| Test plants | Damage in % | |
| CHEAL | 98 | 98 |
| ECHCG | 85 | 80 |
| SINAL | 90 | 90 |
| SOLNI | 80 | 80 |

We claim:
1. A 4-benzoylisothiazole of the general formula 1

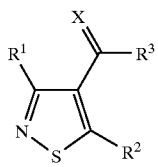

where the substituents have the following meanings:

X is oxygen or sulfur;

$R^1$ is hydrogen, alkyl, alkenyl, alkynyl; unsubstituted or substituted alkoxycarbonyl;

unsubstituted or substituted aryl, unsubstituted or substituted heterocyclyl or unsubstituted or substituted hetaryl;

$R^2$ is hydrogen, alkyl, alkenyl, alkynyl, cycloalkyl or cycloalkenyl, it being possible for these radicals to have attached to them one or more of the following groups: halogen, alkyl, alkenyl or alkynyl;

aryl, it being possible for this radical to have attached to it one or more of the following groups:

alkyl, alkenyl, alkynyl, alkoxy, alkenyloxy, alkynyloxy, alkylthio or alkenylthio, it being possible for these radicals to be partially or fully halogenated or to have attached to them one or more of the following groups:

alkoxy, alkenyloxy, aryloxy, alkylsulfonyl, alkenylsulfonyl or arylsulfonyl;

alkylsulfonyl or alkoxycarbonyl;

unsubstituted or substituted aryloxy or unsubstituted or substituted arylthio;

unsubstituted or substituted mono- or dialkylamino, unsubstituted or substituted mono- or diarylamino or unsubstituted or substituted N-alkyl-N-arylamino, it being possible for alkyl and aryl to be identical or different;

halogen, cyano or nitro;

hetaryl or heterocyclyl, it being possible for these radicals to be partially or fully halogenated or to have attached to them one or more of the following groups:

alkyl, alkoxy or aryl, and it being possible, in the case of heterocyclyl, for at least one of the nitrogens to have attached to it one of the following groups:

alkyl, alkenyl, alkynyl, cycloalkyl, haloalkyl, alkoxy, alkenyloxy, alkynyloxy, cycloalkyloxy, haloalkoxy, unsubstituted or substituted aryl or unsubstituted or substituted aryloxy;

$R^3$ is a radical of the general formula 2a–d

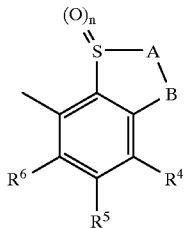

-continued

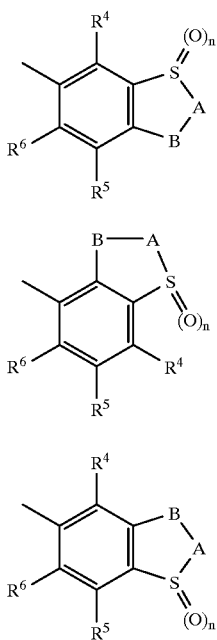

2b

2c

2d where n, A, B and the substituents $R^4$, $R^5$ and $R^6$ have the following meanings:
n is zero, one or two,
A is a chain (—$CR^7R^8$—), (—$CR^7R^8$—$CR^9R^{10}$—), (—$CR^7$=$CR^8$—), (—$CR^7R^8$—$CR^7$=$CR^8$—) or a nitrogen atom which, in turn, can be substituted by a substituent selected from the group consisting of hydrogen, alkyl, alkenyl, unsubstituted or substituted aryl or arylalkyl, alkoxy, halogen, haloalkyl or haloalkoxy;
B is a group consisting of C=O, C=$NR^{11}$, $CR^{12}$—$NR^{13}R^{14}$, $CR^{12}$—$OR^{15}$, $CR^{16}R^{17}$, $CR^{12}$—$SR^{15}$, or 1,3-dioxanyl or 1,3-dioxolanyl, each of which is substituted by hydrogen or alkyl, or a hetero atom selected from the group consisting of oxygen, sulfur or nitrogen, it being possible for the nitrogen, in turn, to be substituted by a substituent selected from the group consisting of hydrogen, alkyl, alkenyl, unsubstituted or substituted aryl or arylalkyl, alkoxy, halogen, haloalkyl or haloalkoxy,
the bond between A and B can be saturated or unsaturated, $R^4$–$R^6$ can be identical or different and independently of one another are hydrogen, alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, alkynylamino, cycloalkylamino, cycloalkenylamino, sulfonyl, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, aminosulfonyl, unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different, alkoxyaminocarbonyl, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfoxyl, haloalkenylsulfoxyl, haloalkynylsulfoxyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; cyano or nitro; or one of the following groups:

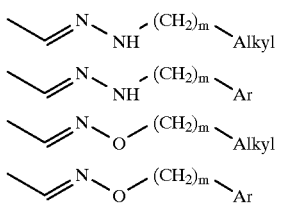

-continued

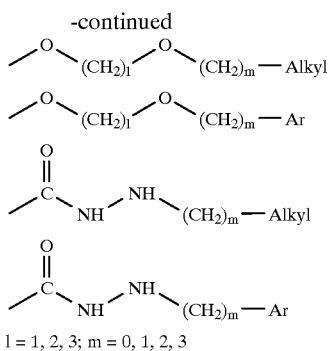

l = 1, 2, 3; m = 0, 1, 2, 3

$R^7$, $R^8$ independently of one another are hydrogen, alkyl, haloalkyl, alkoxy, haloalkoxy; unsubstituted or substituted phenyl, it being possible for the substituents to consist of alkyl, alkoxy, haloalkoxy, haloalkyl, halogen, cyano, nitro;

$R^9$ is hydrogen, alkyl, haloalkyl, alkoxy, $C_1$-$C_6$-haloalkoxy; unsubstituted or substituted phenyl, it being possible for the substituents to consist of alkyl, alkoxy, haloalkoxy, haloalkyl, halogen, cyano, nitro;

$R^{10}$ is hydrogen, alkyl, haloalkyl, alkoxy, haloalkoxy; unsubstituted or substituted phenyl, it being possible for the substituents to consist of alkyl, alkoxy, haloalkoxy, haloalkyl, halogen, cyano, nitro;

$R^{11}$ is hydrogen, amino, unsubstituted or substituted mono- or dialkylamino or N-alkyl-N-arylamino, it being possible for alkyl and aryl to be identical or different, alkyl, haloalkyl, alkoxy, haloalkoxy, alkenyl, haloalkenyl, alkynyl;
    unsubstituted or substituted phenyl, it being possible for the substituents to consist of alkyl, alkoxy, haloalkoxy, haloalkyl, halogen, cyano, nitro;
    unsubstituted or substituted benzyl, it being possible for the substituents to consist of alkyl, alkoxy, haloalkoxy, haloalkyl, halogen, cyano, nitro;
    unsubstituted or substituted benzyloxy, it being possible for the substituents to consist of alkyl, alkoxy, haloalkoxy, haloalkyl, halogen, cyano, nitro;

$R^{12}$ is hydrogen, alkyl, alkoxy, haloalkyl, haloalkoxy;
    unsubstituted or substituted phenyl, it being possible for the substituents to consist of one to three halogens, alkyl, alkoxy, haloalkoxy, nitro; $R^{12}$ and $R^9$ or $R^{12}$ and $R^7$ can form a bond;

$R^{13}$, $R^{14}$ independently of one another are hydrogen, alkyl, alkenyl, haloalkyl, haloalkenyl, alkoxy, haloalkoxy;
    unsubstituted or substituted phenyl, it being possible for the substituents to consist of alkyl, alkoxy, haloalkoxy, haloalkyl, halogen, cyano, nitro;
    unsubstituted or substituted benzyl, it being possible for the substituents to consist of alkyl, alkoxy, haloalkoxy, haloalkyl, halogen, cyano, nitro;

$R^{15}$ is hydrogen, alkyl, haloalkyl, unsubstituted or substituted phenyl, it being possible for the substituents to consist of alkyl, alkoxy, haloalkoxy, haloalkyl, halogen, cyano, nitro;
    unsubstituted or substituted benzyl, it being possible for the substituents to consist of alkyl, alkoxy, haloalkoxy, haloalkyl, halogen, cyano, nitro;

$R^{16}$, $R^{17}$ independently of one another are hydrogen, alkyl;
    unsubstituted or substituted phenyl, it being possible for the substituents to consist of one to three halogens, alkyl, alkoxy, haloalkoxy, nitro; $R^{16}$ and $R^7$ or $R^{16}$ and $R^9$ can form a bond;

or a salt of a 4-benzoylisothiazole of the general formula 1 which is conventionally used in agriculture.

2. A 4-benzoylisothiazole of the general formula 1 as claimed in claim 1 where X is oxygen.

3. A 4-benzoylisothiazole of the general formula 1 as claimed in claim 1, where $R^1$ is hydrogen or unsubstituted or substituted alkoxycarbonyl.

4. A 4-benzoylisothiazole of the general formula 1 as claimed in claim 1 where $R^2$ is alkyl, cycloalkyl, aryl which can be mono- or polysubstituted by halogen or haloalkyl, or hetaryl which can be mono- or polysubstituted by halogen.

5. A 4-benzoylisothiazole of the general formula 1 as claimed in claim 1 where $R^2$ is methyl, ethyl, isopropyl, tert-butyl, cyclopropyl, 1-methylcyclopropyl, 3-trifluoromethylaryl, 2,4-difluoroaryl, 1,3-benzodioxolyl, 2,2-difluoro-1,3-benzodioxolyl, 1,3-benzoxathiolyl, 3,3-dioxo-1,3-benzoxathiolyl, benzoxazolyl, pyrazolyl or thienyl.

6. A 4-benzoylisothiazole of the general formula 1 as claimed in claim 1 where $R^3$ is a radical of the general formula 2b or 2d

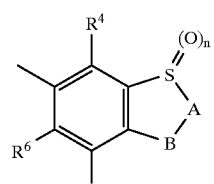

2b

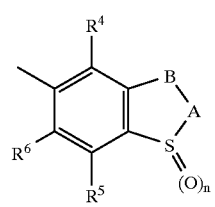

2d

7. A 4-benzoylisothiazole of the general formula 1 as claimed in claim 1 where $R^3$ is a radical of the general formula 2b or 2d

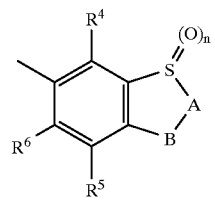

2b

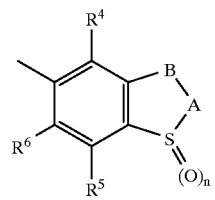

2d where the substituents $R^4$–$R^6$ have the following meanings: $R^4$–$R^6$ can be identical or different and independently of one another are hydrogen, alkyl, cycloalkyl, aryl, hydroxyl, alkoxy, cylcoalkoxy, aryloxy, thio, alkylthio, cycloalkylthio, arylthio, amino, unsubstituted or substituted mono- or dialkylamino or mono- or diarylamino or N-alkyl-N-arylamino, it being possible for alkyl and aryl to be identical or different, cycloalkylamino, sulfonyl, alkylsulfonyl, cycloalkylsulfonyl, arylsulfonyl, sulfoxyl, alkylsulfoxyl, cycloalkylsulfoxyl, arylsulfoxyl, alkylcarbonyl, cycloalkylcarbonyl, arylcarbonyl, carboxyl, alkoxycarbonyl, cycloalkoxycarbonyl, aryloxycarbonyl, aminocarbonyl, unsubstituted or substituted mono- or dialkylaminocarbonyl or mono- or diarylaminocarbonyl or N-alkyl-N-arylaminocarbonyl, it being possible for alkyl and aryl to be identical or different, alkoxyaminocarbonyl, cycloalkoxycarbonylamino, aryloxycarbonylamino, halogen, haloalkyl, haloalkoxy, haloalkylthio, haloalkylamino, haloalkylsulfonyl, haloalkylsulfoxyl, haloalkylcarbonyl, haloalkoxycarbonyl, haloalkylaminocarbonyl, haloalkoxycarbonylamino, cyano or nitro.

8. A 4-benzoylisothiazole of the general formula 1 as claimed in claim 1 where $R^3$ is a radical of the general formula 2b or 2d

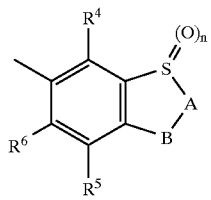

2b

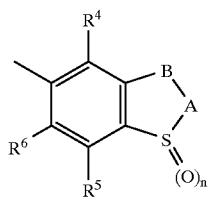

2d where $R^4$, $R^5$ and $R^6$ have the following meanings:
$R^4$–$R^6$ can be identical or different and independently of one another are a low-molecular-weight radical selected from the group consisting of hydrogen, alkyl, hydroxyl, alkoxy, sulfonyl, sulfonylalkyl, halogen, haloalkyl, cyano or nitro.

9. A 4-benzoylisothiazole of the general formula 1 as claimed in claim 1 where $R^3$ is a radical of the general formula 2e

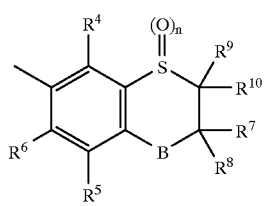

2e where $R^5$ and $R^6$ are hydrogen, alkyl, alkenyl, alkynyl, alkoxy, haloalkyl, haloalkoxy, halogen, nitro or cyano and $R^4$ is hydrogen, alkyl, alkenyl, alkynyl, alkoxy, haloalkyl, $C_1$–$C_4$-haloalkoxy, halogen, nitro or cyano and n, B, $R^7$, $R^8$, $R^9$ and $R^{10}$ have the meanings given in claim 1.

10. A 4-benzoylisothiazole of the general formula 1 as claimed in claim 1 where $R^3$ is a radical of the general formula 2f

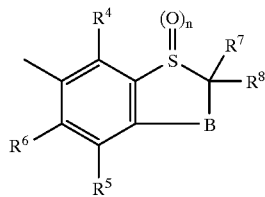

2f where $R^5$ and $R^6$ are hydrogen, alkyl, alkenyl, alkynyl, alkoxy, haloalkyl, haloalkoxy, halogen, nitro or cyano and $R^4$ is hydrogen, alkyl, alkenyl, alkynyl, alkoxy, haloalkyl, haloalkoxy, halogen, nitro or cyano and n, B, $R^7$ and $R^8$ have the meanings given in claim 1.

11. A 4-benzoylisothiazole of the general formula 1 as claimed in claim 1 where $R^3$ is a radial of the general formula 2g

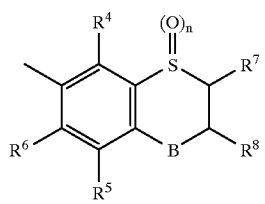

2g where $R^4$ and $R^5$ are hydrogen, alkyl, alkenyl, alkynyl, alkoxy, haloalkyl, haloalkoxy, halogen, nitro or cyano and $R^4$ is hydrogen, alkyl, alkenyl, alkynyl, alkoxy, haloalkyl, haloalkoxy, halogen, nitro or cyano and n, B, $R^7$ and $R^8$ have the meanings given in claim 1.

12. A 4-benzoylisothiazole of the general formula 1 as claimed in claim 1 where $R^3$ is a radical of the general formula 2a–d

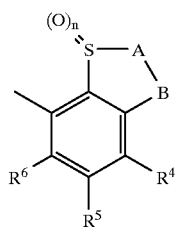

2a

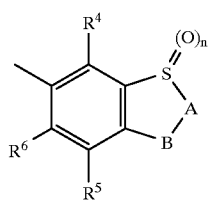

2b

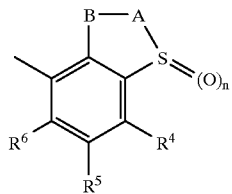

2c

-continued

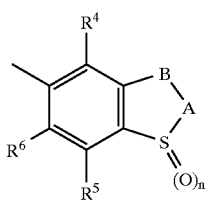
2d where n is one or two and B is $CR^{12}$–$OR^{15}$, $R^{12}$ and $R^{15}$ having the meanings given in claim 1.

13. A 4-benzoylisothiazole of the general formula 1 as claimed in claim 1 where $R^3$ is a radical of the general formula 2b or 2d

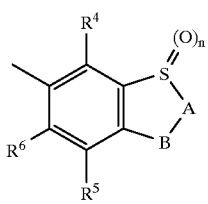
2b

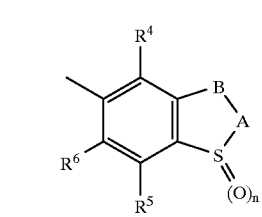
2d where n, B, $R^4$, $R^5$ and $R^6$ have the meanings given in claim 1 and A is a nitrogen atom which, in turn, can be substituted by hydrogen, alkyl, alkenyl, unsubstituted or substituted by aryl or arylalkyl, alkoxy, halogen, haloalkyl or haloalkoxy.

14. A 4-benzoylisothiazole of the general formula 1 as claimed in claim 1 where $R^3$ is a radical of the general formula 2b

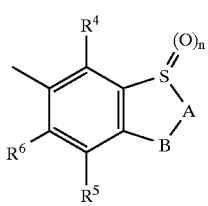
2b

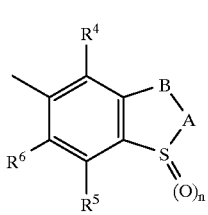
2d where n, $R^4$, $R^5$ and $R^6$ have the meanings given in claim 1 and A is a nitrogen atom which, in turn, can be substituted by hydrogen, alkyl, alkenyl, unsubstituted or substituted aryl or arylalkyl, alkoxy, halogen, haloalkyl or haloalkoxy and B is C=O.

15. A process for the preparation of a 4-benzoylisothiazole of the general formula 1 as claimed in claim 1, which comprises reacting a haloisothiazole compound of the general formula 3

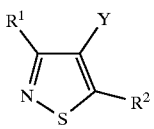
3 where Y is halogen with elemental magnesium, an organomagnesium or an organolithium compound and with a carboxylic acid derivative of the general formula 4

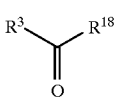
4 where $R^{18}$ is halogen, N-alkoxy-N-alkylamino or cyano in a temperature range of from −78° C. to 111° C. in the presence of an inert solvent.

16. A process for the preparation of a 4-benzoylisothiazole of the general formula 1 as claimed in claim 1, which comprises reacting a halobenzene of the general formula 5

5

$R^3$—Y where Y is halogen with elemental magnesium, an organomagnesium or an organolithium compound and with an isothiazolecarboxylic acid derivative of the general formula 6a or 6b,

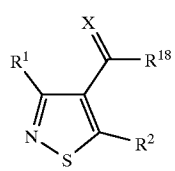
6a

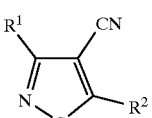
6b where $R^{18}$ is halogen or N-alkoxy-N-alkylamino in a temperature range of from −78° C. to 111° C. in the presence of an inert solvent.

17. A herbicidal composition comprising a 4-benzoylisothiazole of the general formula 1 as claimed in claim 1 and inert additives.

18. A method of controlling undesirable vegetation, which comprises treating the undesirable plants and/or their environment with a herbicidally active amount of a 4-benzoylisothiazole of the general formula 1 as claimed in claim 1.

* * * * *

UNITED STATES PATENT AND TRADEMARK OFFICE
CERTIFICATE OF CORRECTION

PATENT NO.: 5,945,381

DATED: August 31, 1999

INVENTOR(S): ENGEL et al.

It is certified that error appears in the above-identified patent and that said Letters Patent is hereby corrected as shown below:

Col. 85, claim 12, line 12, "$CR^{12}\text{-}OR^15$," should be --$CR^{12}\text{-}OR^{15}$,--.

Col. 85, claim 14, line 42, after "2b" insert --or 2d--.

Signed and Sealed this

Eighth Day of February, 2000

Attest:

Attesting Officer

Q. TODD DICKINSON

Commissioner of Patents and Trademarks